(12) United States Patent
Voziyanov

(10) Patent No.: US 11,473,066 B2
(45) Date of Patent: Oct. 18, 2022

(54) FLP-TAL RECOMBINASES

(71) Applicant: Louisiana Tech Research Corporation, Ruston, LA (US)

(72) Inventor: Yuri Voziyanov, Ruston, LA (US)

( * ) Notice: Subject to any disclaimer, the term of this patent is extended or adjusted under 35 U.S.C. 154(b) by 466 days.

(21) Appl. No.: 16/679,201

(22) Filed: Nov. 9, 2019

(65) Prior Publication Data

US 2020/0385694 A1     Dec. 10, 2020

Related U.S. Application Data

(60) Provisional application No. 62/758,512, filed on Nov. 9, 2018.

(51) Int. Cl.
    *C12N 9/12*      (2006.01)
    *C12N 15/90*      (2006.01)

(52) U.S. Cl.
    CPC ......... *C12N 9/1241* (2013.01); *C12N 15/907* (2013.01); *C07K 2319/09* (2013.01); *C07K 2319/80* (2013.01)

(58) Field of Classification Search
None
See application file for complete search history.

(56) References Cited

PUBLICATIONS

Chen et al. (Crystal Structure of a Flp Recombinase-Holliday Junction Complex: Assembly of an Active Oligomer by Helix Swapping, Molecular Cell, vol. 6, 885-897, Oct. 2000) (Year: 2000).*

* cited by examiner

*Primary Examiner* — Suzanne M Noakes
*Assistant Examiner* — Jae W Lee
(74) *Attorney, Agent, or Firm* — Elliot C. Mendelson; Mendelson IP

(57) ABSTRACT

The present invention provides chimeric Flp-TAL recombinases, as well as nucleic acids, and methods for the use of the chimeric Flp-TAL recombinases for site-specific alteration of a target sequence in cells.

18 Claims, 14 Drawing Sheets
Specification includes a Sequence Listing.

FRT_TAL-FL61 (outer FRT; the EM-7 promoter is located before the recombination site)

CMV promoter
ATCGGCATAGTATATCGGCATAGTATAATACGACAAGGTGACGAACTAAACC
CAATCGAATTATCATACCAGCTC GAAGTTCCTATAC TgataAtA
GAAatGGcAtTgt ACTTCGATTAATGCAATAAAGCTTAGT
CTTC cctttgaaaaacacgatgataatatggccacaacc
vector FRT_TAL-FL63 (outer FRT; the EM-7 promoter is located before the recombination site)

CMV promoter
ATCGGCATAGTATATCGGCATAGTATAATACGACAAGGTGACGAACTAAACC
CAATCGAATTATCATACCAGCTC GAAGTTCCTATAC TGCACTTA GAATAATCCTTTT
TGTGTGCACATGCTATCGAAGACC
CTTC cctttgaaaaacacgatgataatatggccacaacc
vector FRT_TAL-FL71 (outer FRT site; the lacIQ promoter is located before the recombination site)

EF1a promoter
gactcactatagggagacccaagctggctagg
tggtgcaaaacctttcgcggtatggcatgatagcgcccggaagagagtcaattcagg
GACATACATTAAGTAACTTAAAAAAAACTTACAACTTC cctagTaCatTAC TaTtTgGA
GTATAGGAACTTC TATTGAATTAAATGCCTACTGTTC
vector

FIG. 8

```
MVDLRTLGYSQQQQEKIKIKVRSIVAQHEALVGHGFIHAHIVALSQHPAALGTVAVTYQHIIALPEAT
HEDLVGVGKQWSGARALEALTPDAGETRGSPIQLDTGQLVKLAHRGGVTAMEAVHASRNAITGAPLNLTP
DQVVAIASNNGGKQALETVQRLLPVLCQDHGLTPDQVVAIASHDGGKQALETVQRLLPVLCQDHGLTPDQ
VVAIASNIGGKQALETVQRLLPVLCQDHGLTPDQVVAIASHDGGKQALETVQRLLPVLCQDHGLTPDQVV
AIASNIGGKQALETVQRLLPVLCQDHGLTPDQVVAIASHDGGKQALETVQRLLPVLCQDHGLTPDQVVAI
ASNGGGKQALETVQRLLPVLCQDHGLTPDQVVAIASHDGGKQALETVQRLLPVLCQDHGLTPDQVVAIAS
NIGGKQALETVQRLLPVLCQDHGLTPDQVVAIASHDGGKQALETVQRLLPVLCQDHGLTPDQVVAIASNI
GGKQALETVQRLLPVLCQDHGLTPDQVVAIASNIGGKQALETVQRLLPVLCQDHGLTPDQVVAIASNGGG
KQALETVQRLLPVLCQDHGLTPDQVVAIASHDGGKQALETVQRLLPVLCQDHGLTPDQVVAIASNGGGKQ
ALETVQRLLPVLCQDHGLTPDQVVAIASHDGGKQALETVQRLLPVLCQDHGLTPDQVVAIASHDGGKQAL
ETVQRLLPVLCQDHGLTPDQVVAIASHDGGKQALESIVAQLSRPDPALAALTNDHLVALACGGRPAMDA
VKKGLPHAPELIREVNRRIGERTSHRVADYAQVVEVLEEPQCHSHPAYAEDEAMTQEGNC
```

FIG. 9

>71-18_TAL

MSQFDILCKTPPEVLVRQFVEPFERPSGEKIASCTAELIYLCRVVTHDGAAIKRSTFVNYNSIIGN
SLSFDIVNKSLQFRYKTQKATILEASLKKLIPAWEFTIIPYNGQKHQPDITDIVSSLQLQFESPEE
ADKONSHSKKMLEALLSEGESIWEITEKILNSFEYTSPCTKTPALYQFLPLATFINCGRFSDIKNV
DKKSFKLVQNKYLGSTIQCLVTETKTSVSRSIYFPSARGRIDPLVYLDEFLRNSEPVLKRVNETGN
SSSNKQEYQLLKDNLVRSYNKALKKSAPYPFFAIKNGPKSHIGRHLMTSFLSMKGLTELTNVVGNW
SDKRASAVARTTYTHQITAIPDHYFALVSRYYEYDPISKEMIALKDETNPIEEWQHIEQLKGSAEG
SIPYPAKNGLISQKVLDYLSSYINRRIGT[L6 linker][delta 152 section]LTPDQVVAIASNNGGKQAL
ETVQRLLPVLCQDHGLTPDQVVAIASHDGGKQALETVQRLLPVLCQDHGLTPDQVVAIASNIGGKQ
ALETVQRLLPVLCQDHGLTPDQVVAIASNGGGKQALETVQRLLPVLCQDHGLTPDQVVAIASNIGG
KQALETVQRLLPVLCQDHGLTPDQVVAIASNGGGKQALETVQRLLPVLCQDHGLTPDQVVAIASNG
GGKQALETVQRLLPVLCQDHGLTPDQVVAIASHDGGKQALETVQRLLPVLCQDHGLTPDQVVAIAS
NIGGKQALETVQRLLPVLCQDHGLTPDQVVAIASNGGGKQALETVQRLLPVLCQDHGLTPDQVVAI
ASNIGGKQALETVQRLLPVLCQDHGLTPDQVVAIASNIGGKQALETVQRLLPVLCQDHGLTPDQVV
AIASNGGGKQALETVQRLLPVLCQDHGLTPDQVVAIASHDGGKQALETVQRLLPVLCQDHGLTPDQ
VVAIASNGGGKQALETVQRLLPVLCQDHGLTPDQVVAIASHDGGKQALETVQRLLPVLCQDHGLTP
DQVVAIASHDGGKQALETVQRLLPVLCQDHGLTPDQVVAIASHDGGKQALE[+95 section]
[SV40 NLS]G[end]

Color coding:
MSQFDILC... - Flp
GT and G - short connectors
[highlighted] - L6 linker
[highlighted] and [highlighted] - delta 152 and +95 sections of the TAL module
LTPDQVVAI... - TAL DBD unit (in this case 18 repeats)
[highlighted] - SV40 NLS

FIG. 10

\>TAL/L24-TAL/R15
GTAACTTAAAAAAAAACTTTACACAGTCTG cctagtacattAC TaTtTgGA
gTATAGcAACTTC TATTTGCATATTCATAATCT \>TAL/L18-TAL/R15
TAAAAAAAACTTTACACAGTCTG cctagtaCaTAC TaTtTgGA gTATAGcAACTTC
TATTTGCATATTCATAATCT \>TAL/L15-TAL/R15
AAAAAACTTTACACAGTCTG cctagtaCaTAC TaTtTgGA gTATAGcAACTTC
TATTTGCATATTCATAATCT Codes:
- TAL binding sequences
- FL-71 binding sequences
- spacer in FL-71

FIG. 11

>loxP
ATAACTTCGTATAA TGTATG CTATACGAAGTTAT

>TAL/L15-TAL/R12_1
AAATAAGAAATTTGTAAA TTCCTTCtgATAA ctagaa ATAgAgGATccagt
TTCTTTTGGTAACCTAAA >TAL/L15-TAL/R15_2
CAATGGAAATAAGAAATTTGTAAA TTCCTTCtgATAA ctagaa ATAgAgGATccagt
TTCTTTTGGTAACCTAAATT >TAL/L15-TAL/R12_2
CAATGGAAATAAGAAATTTGTAAA TTCCTTCtgATAA ctagaa ATAgAgGATccagt
TTCTTTTGGTAACCTAAA Codes:
▨ – TAL binding sequences
▨ – LL-69 binding sequences
▨ – spacer in LL-69

FIG. 12

\>iCreM24/69-TAL
ATGGTGCCCAAGAAGAAGAGGAAAGTCTCCAACCTGCTGACTGTGCACCAAAACCTGCCTGCCCTCCCTGTGG
ATGCCACCTCTGATGAAGTCATGAAGAACCTGATGGACATGTTCAGGGACAGGCAGGCCTTCTCTGAACACAC
CTGGAAGATGCTCCTGTCTGTGTGCAGATCCTGGGCTGCCTGGTGCAAGCTGAACAACAGGAAATGGTTCCCT
GCTGAACCTGAGGATGTGAGGGACTACCTCCTGTACCTGCAAGCCAGAGGCCTGGCTGTGAAGACCATCCAAC
AGCACCTGGGCCAGCTCAACATGCTGCACAGGAGATCTGGCCTGCCTCGCCCTTCTGACTCCAATGCTGTGTC
CCTGGTGATGAGGAGAATCAGAAAGGAGAATGTGGATGCTGGGGAGAGAGCCAAGCAGGCCCTGGCCTTTGAA
CGCACTGACTTTGACCAAGTCAGATCCCTGATGGAGAACTCTGACAGATGCCAGGACATCAGGAACCTGGCCT
TCCTGGGCATTGCCTACAACACCCTGCTGCGCATTGCCGAAATTGCCAGAATCAGAGTGAAGGACATCTCCCG
CACCGATGGTGGGAGAATGCTGATCCACATTGGCAGGACCAAGACCCTGGTGTCCACAGCTGGTGTGGAGAAG
GCCCTGTCCCTGGGGGTTACCAAGCTGGTGGAGAGATGGATCTCTGTGTCTGGTGTGGCTGATGACCCCAACA
ACTACCTGTTCTGCCGGGTCAGAAAGAATGGTGTGGCTGCCCCTTCTGCCACCTCCCAACTGTCCACCCGGGC
CCTGGAAGGGATCTTCGAGGCCACCCACCGCCTGATCTATGGTGCCAAGGATGACTCTGGGCAGAGATACCTG
GCCTGGTCTGGCCACTCTGCCAGAGTGGGTGCTGCCAGGGACATGGCCAGGGCTGGTGTGTCCATCCCTGAAA
TCATGCAGGCTGGTGGCTGGACCAATGTGAACATTGTGATGAACTACATCAGAAACCTGGACTCTGAGACTGG
CCAGCAGAGTGGGATGAGGCGCAATCGGCTCTGCGTGCAGCCGATGACCCGCCACCCACCGTGCGTGTCGCTG
TCACTGCCGCGCGGCCGCCGCGCGCCAAGCCGGCCCCGCGACGGCGTGCTGCGCAACCCTCCGACGCTTCGCC
GGCCGCGCAGGTGGATCTACGCACGCTCGGCTACAGTCAGCAGCAGCAAGAGAAGATCAAACCGAAAGGTGCG
TTCGACAGTGGCGCAGCACCACGAGGCACTGGTGGGCCATGGGTTTACACACGCGCACATCGTTGCGCTCA

Codes:
▓ – end of Cre gene
⋯ – KpnI site
▪ – linker between the Cre and TAL modules
▓ – beginning of the TAL module (delta-117)

FIG. 13

FLP-TAL RECOMBINASES

CROSS-REFERENCE TO RELATED APPLICATION

The application claims the benefit of U.S. Provisional Application No. 62/758,512, filed Nov. 9, 2018, which is incorporated by reference in its entirety.

FEDERALLY SPONSORED RESEARCH OR DEVELOPMENT

This invention was made with government support under Grant No. R01GM085848 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on May 4, 2022 is named Flp-TAL_recombinases_sequence_listing_ST25.txt and is 103 KB in size.

BACKGROUND OF INVENTION

The relative simplicity, with which target specificity of certain site-specific nucleases can be changed, particularly in the CRISPR/Cas9 and TALEN systems, has made these DNA manipulation enzymes some of the more preferred tools in the field of genome engineering in recent years. Miller J C, et al. (2011) A TALE nuclease architecture for efficient genome editing. Nat Biotechnol 29(2):143-148, Cong L, et al. (2013) Multiplex genome engineering using CRISPR/Cas systems. Science 339(6121):819-823. However, several inherent properties of these site-specific nucleases, which includes the necessity to introduce double strand breaks, the reliance on the endogenous cell DNA repair machinery to process these breaks, and the frequency at which they target unintended locations, limits their utility.

Tyrosine recombinases, such as popular genome engineering tools Flp and Cre, are highly specific for their targets, versatile in performing DNA manipulation reactions, and can be easily regulated. These features, however, are only useful for genome engineering if the native targets for these tyrosine recombinases are pre-introduced into a genome locale of interest. This limits the utility of the naturally occurring enzymes in applications that are aimed to manipulate the genome of previously unmodified cells.

Tyrosine recombinase variants can be evolved that are able to recognize target sequences that vary from the native enzyme's recombination target sequence. Buchholz F & Stewart A F (2001) Alteration of Cre recombinase site specificity by substrate-linked protein evolution. Nat Biotechnol 19(11):1047-1052, Sarkar I, et al. (2007) HIV-1 proviral DNA excision using an evolved recombinase. Science 316(5833):1912-1915, Bolusani S, et al. (2006) Evolution of variants of yeast site-specific recombinase Flp that utilize native genomic sequences as recombination target sites. Nucleic Acids Res 34(18):5259-5269, Shultz J L, et al., (2011) A genome-wide analysis of FRT-like sequences in the human genome. PLoS One 6(3):e18077. The total number of such target-like sequences in a genome can be quite substantial: The human genome, for example, has about 600,000 FRT-like sequences. That is, sequences that have a level of homology to FRT, the native recombination target for Flp recombinase. This number corresponds to one FRT-like sequence per ~5 kb. Shah et al. (2011). Such a density allows DNA manipulation in essentially all genome locales, provided the variants that are evolved to recombine these target-like sequences can bind them in their native chromosomal environment, out-competing other DNA binding proteins, primarily histones.

However, tyrosine recombinases appear to lack well-defined DNA binding motifs with clear rules that specify which residues need to be mutated to achieve a particular desired target specificity. Guo F, et al., (1997) Structure of Cre recombinase complexed with DNA in a site-specific recombination synapse. Nature 389(6646):40-46, Chen Y, et al., (2000) Crystal structure of a Flp recombinase-Holliday junction complex: assembly of an active oligomer by helix swapping. Mol Cell 6(4):885-897. Moreover, the entire structure of tyrosine recombinases seems to take part in the functional target recognition. Buchholz F & Stewart A F (2001), Bolusani S, et al. (2006). Such mode of protein-DNA binding restricts the evolution process of the target-specific tyrosine recombinase variants to mainly random target-linked mutagenesis, although the modification of the residues known to participate in the protein-DNA recognition can speed up the evolution process. Buchholz et al. (2001), Sarkar I, et al. (2007), Shultz et al. (2011), Karpinski J, et al. (2016) Directed evolution of a recombinase that excises the provirus of most HIV-1 primary isolates with high specificity. Nat Biotechnol 34(4):401-409, Shah et al., (2015) Target-specific variants of Flp recombinase mediate genome engineering reactions in mammalian cells. The FEBS journal 282(17):3323-3333.

Thus, there remains in the art a need for improved compositions and methods for genomic engineering.

SUMMARY OF THE DISCLOSURE

The invention provides a non-naturally occurring chimeric tyrosine recombinase polypeptide comprising a tyrosine recombinase variant domain and a TAL DNA-binding domain, such as where the tyrosine recombinase variant is selected from a group consisting of Flp, CRE (and Cre-like recombinases such as Dre, SCre, Vcre, Vika, Nigri, and Panto), R, B2, B3, KD, KW, SM, and TD. In certain embodiments of the invention, the chimeric tyrosine recombinase is a chimeric Flp-TAL recombinase and the tyrosine recombinase variant is a Flp recombinase variant. In some embodiments of the invention, the chimeric tyrosine recombinase is a chimeric Cre-TAL recombinase, a chimeric R-TAL recombinase, a chimeric B2-TAL recombinase, a chimeric B3-TAL recombinase, a chimeric KW-TAL recombinase, a chimeric SM-TAL recombinase, and/or a chimeric TD-TAL recombinase.

In certain instances, the presence of a linker peptide may optionally be included in the chimeric tyrosine recombinase of the invention. In such cases, the linker peptide operably connects the tyrosine recombinase variant domain and the TAL DNA-binding domain (TAL DBD). When present, the linker peptide may operably connect the N-terminus of the tyrosine recombinase variant domain to the C-terminus of the TAL DNA-binding domain. Alternatively, the linker peptide may operably connect the C-terminus of the tyrosine recombinase variant domain to the N-terminus of the TAL DNA-binding domain. In certain instances, additional sequences of TAL beyond the core TAL DBD may function as a linker.

In certain embodiments, the chimeric tyrosine recombinase may advantageously include a nuclear localization signal. Certain tyrosine recombinases, such as Flp, contain an endogenous nuclear localization signal. However, a heterologous NLS may still enhance recombinase activity even for those tyrosine recombinases that already contain an endogenous NLS. When utilized, the heterologous nuclear localization signal (NLS) is operably linked to the chimeric tyrosine recombinase.

The recombinase variant domain utilized in the chimeric recombinases of the invention will often have reduced recombinase activity, relative to its respective wild-type tyrosine recombinase. Such activity may be 25, 50, 75, or 90 percent reduced, relative to the wild type level of activity. Activity may be measured, for example, in *E. coli* as described herein.

The chimeric tyrosine recombinases of the invention may have a range of specificities in each of the domains of the chimeric recombinase. For example, the tyrosine recombinase variant domain may be broadly specific, specific, very specific, highly specific, or stringently specific for it target sequence. In the case of Flp, for example, that sequence is denoted FRT. Thus, the for the chimeric Flp-TAL recombinases of the invention, the target sequence for the Flp variant domain will generally be a FRT-like sequence. Similarly, in the case where the chimeric tyrosine recombinase is a chimerice Cre-TAL recombinases, where Cre recognizes a sequence known as Lox (or LoxP), the target sequence will generally be a Lox-like sequence, etc.

Similarly, the TAL DNA-binding domain may also be specific, very specific, highly specific, or stringently specific for its target sequence. Generally, that target sequence of the TAL DNA-binding domain will be upstream or downstream of the target sequence of the recombinase domain. In certain instances, the sequences targeted by the tyrosine recombinase domain and the TAL DNA-binding domains will be separated from one another (upstream and/or downstream) by 3-12 bp.

As noted, the level of specificity for the TAL DNA-binding domain may be specific, very specific, highly specific, or stringently specific for the target nucleic acid sequence. Generally, the length of the target nucleic acid sequence will be in the range of about 9-24 bp, 12-24 bp, or 15-24 bp in length, though in certain instances longer recognition sequences of up to about 35 bp may be used.

In certain embodiments of the invention, the chimeric tyrosine recombinases, including Flp-TAL recombinases of the invention, where the tyrosine recombinase variant domain may a have broad or relaxed target sequence specificity relative to the wild-type recombinase. This may be advantageous in those instances where it is desirable for the target specificity of the chimeric tyrosine recombinase to be driven substantially by the sequence to which the TAL DNA-binding domain has been programmed.

The invention also provides a chimeric tyrosine recombinase, such as a chimeric Flp-TAL recombinase, where the TAL DNA-binding domain stabilizes the binding of the chimeric recombinase on its target sequence and enhances the recombinase activity of the tyrosine recombinase domain.

In certain embodiments, the invention provides a chimeric tyrosine recombinase, such as a Flp-TAL recombinase, wherein the chimeric recombinase is able to recombine a target sequence in a prokaryotic cell. The invention also provides a chimeric tyrosine recombinase, such as a chimeric Flp-TAL, where the chimeric recombinase is able to recombine a genomic target sequence in a eukaryotic cell.

In certain embodiments of the invention, the chimeric tyrosine recombinases are most advantageously utilized in pairs. Thus, the invention also provides a composition where there is a first and a second chimeric tyrosine recombinase, such as a chimeric Flp-TAL recombinase and chimeric Cre-TAL recombinase, where the first chimeric tyrosine recombinase contains a TAL DNA-binding domain that is specific, very specific, highly specific, or stringently specific for a nucleic acid sequence upstream of the recombinase target sequence (such as a FRT-like sequence) and the second chimeric tyrosine recombinase contains a TAL DNA-binding domain that is specific, very specific, highly specific, or stringently specific for a nucleic acid sequence downstream of the recombinase target sequence (such as a FRT-like sequence). Often, the tyrosine recombinase target sequence and the TAL DNA-binding sequence may be separated by 3-12 bp. Pairs of chimeric tyrosine recombinases may have the same tyrosine recombinase module and differ in the TAL DBD module. Alternatively, individual tyrosine recombinases in a pair of chimeric tyrosine recombinases may be contain tyrosine recombinases that differ in the specificity of the recombinase module for its target sequence (as in, a pair of chimeric Flp-TAL recombinases where one is highly specific one FRT-like sequence and the other is highly specific for another FRT-like sequence or broadly specific for many FRT-like sequences). Alternatively, a pair of chimeric tyrosine recombinases may differ in identity of the tyrosine recombinase itself (as in, a chimeric Cre-TAL recombinase and a chimeric R-TAL recombinase).

In those embodiments of the invention, where the chimeric tyrosine recombinase is a chimeric Flp-TAL recombinase, the Flp variant domain may contain at least 2, 3, 4, 5, 6, 7, 8, or 9 amino acid substitutions selected from the group consisting of A35T, I45V, T50A, A55H, A55S, S59G, S59N, S114P, K173R, I295F, A363E. In some embodiments of the invention, the Flp variant domain may contain at least 2, 3, 4, 5, or all 6 amino acid substitutions selected from the group consisting A35T, I45V, T50A, S114P, I295F, and A263E. In some embodiments of the invention, the Flp variant domain may contain at least 2, 3, 4, 5, 6, 7, 8, 9, 10, 11, 12, or all 13 amino acid substitutions selected from the group consisting of A35T, M44V, T50A, A55H, S59G, K75R, S114P, I157V, K173R, S193G, I295F, and A363E. In some embodiments of the invention, the Flp variant domain may contain at least 2, 3, 4, 5, 6, 7, 8, 9, 10, 11, 12, 13, or all 14 amino acid substitutions selected from the group consisting of Q3R, Q18R, A35T, I45V, T50A, A55H, S59G, K85E, S114P, K173R, L285H, I295F, A324I, and A363E. In some embodiments of the invention, the Flp variant domain may contain at least 2, 3, 4, 5, 6, 7, 8, 9, 10, 11, 12, 13, 14, or all 15 amino acid substitutions selected from the group consisting of A35T, I45V, T50A, A55S, M58V, S59N, T62S, S114P, S130P, F171S, T176A, V213E, N290S, I295F, and A363E.

The invention also provides a chimeric Flp-TAL recombinase, where the Flp variant domain is evolved from a library of Flp genes, where genes bearing common as well as unique mutations are used as templates for generating shuffled variant libraries which can be screened to identify the desired target specificity. In some instances, those common mutations may be selected from one or more of A35T, I45V, T50A, S114P, I295F, and A263E. In some embodiments of the invention, the Flp variant domain may also (or alternatively) be evolved from a library of Flp genes that are randomized at codons 55, 58 and 59.

In those embodiments of the invention where the chimeric tyrosine recombinase is a chimeric Flp-TAL recombinase, the Flp variant domain may be a Flp variant identified in a screening system using a reporter construct bearing FRT and FRT-like sequence.

With respect to the TAL DNA-binding domain utilized in the chimeric tyrosine recombinase of the invention (such as with Flp-TAL recombinases) the TAL DNA-binding domain may be a truncation of the N-terminus and/or the C-terminus of the full TAL effector amino acid sequence. In certain embodiments of the invention, the TAL DNA-binding domain is the core TAL DNA-binding domain that begins at position +152 of the N-terminus of the TAL effector and ends at the position +95. In certain embodiments, however, it may be advantageous for the TAL DNA-binding domain to include amino acid sequence from the TAL effector extending from beyond the N-terminus and/or the C-terminus of the core TAL DNA-binding domain. In certain instances, the TAL effector amino acid sequence extending from the N-terminus and/or the C-terminus of the core TAL DNA-binding domain of the TAL effector may function as a linker between the tyrosine recombinase variant domain and the TAL DNA-binding domain.

In some embodiments, the invention provides a chimeric tyrosine recombinase, such as a chimeric Flp-TAL recombinase, where the recombinase variant domain of the chimeric recombinase has broad (relaxed) specificity to more than one recombination target sequence and target specificity is primarily driven by the specificity of the TAL DNA-binding domain. In some embodiments where the chimeric recombinase is a chimeric Flp-TAL recombinase and the Flp recombinase variant domain is broadly specific for a multiplicity of FRT-like target sequences, the TAL DNA-binding domain may be programmed to be specific, very specific, highly specific, or strictly specific for a target sequence. In certain instances, those target sequences may be separated from one another by 3-12 bp.

The invention also provides a chimeric tyrosine recombinase, such as a chimeric Flp-TAL recombinase, where the isolated recombinase variant domain is unable to efficiently recombine a genomic target sequence (such as a FRT-like genomic sequence) in the absence of the TAL DNA-binding domain.

The invention also provides a chimeric tyrosine recombinase, such as a chimeric Flp-TAL recombinase, where both the recombinase variant domain and the TAL-DNA binding domain are evolved or programmed to be specific, very specific, highly specific, or strictly specific for a target sequence. Those target sequences may be separated from one another by 3-12 bp.

The invention also provides a nucleic acid encoding a non-naturally occurring chimeric tyrosine recombinase comprising a regulatory element operable in a target cell, said regulatory element operably linked to a nucleic acid sequence encoding a chimeric tyrosine recombinase having a tyrosine recombinase variant domain and a TAL DNA-binding domain, where the tyrosine recombinase variant is selected from a group consisting of Flp, Cre (and Cre-like recombinases such as Dre, SCre, Vcre, Vika, Nigri, and Panto), R, B2, B3, KD, KW, SM, and TD. In some embodiments of the invention, the encoded chimeric tyrosine recombinase is a chimeric Flp-TAL recombinase and the tyrosine recombinase variant is a Flp recombinase variant. Nucleic acids of the invention may include endogenous or exogenous regulatory elements, such as enhancers, promoters, and polyadenylation sites. Suitable promoters for the nucleic acids of the invention include inducible, constitutive, or tissue specific promoters. Such promotors may be eukaryotic or prokaryotic.

The invention also includes embodiments where the chimeric tyrosine recombinase of the invention that is encoded in the nucleic acid contains an additional nucleic acid sequence encoding a linker peptide. In such cases, the encoded linker peptide operably connects the Flp recombinase domain to the TAL DNA-binding domain of the encoded chimeric polypeptide. When present, the encoded linker peptide may operably connect the N terminus of the recombinase variant domain to the C terminus of the TAL DNA-binding domain. Alternatively, the encoded linker peptide may operably connect the C-terminus of the recombinase variant domain to the N-terminus of the TAL DNA-binding domain.

The invention further provides a nucleic acid that encodes a chimeric tyrosine recombinase, such as a chimeric Flp-TAL recombinase, where the nucleic acid further may further encode a heterologous nuclear localization signal (NLS) operably linked to the chimeric recombinase.

The invention further provides a nucleic acid that encodes a chimeric tyrosine recombinase, such as a chimeric Flp-TAL recombinase, where the encoded tyrosine recombinase variant domain has reduced recombinase activity, relative to wild-type tyrosine recombinase. Such activity may be 25, 50, 75, or 90 percent reduced, relative to the wild type level of activity, as measured in vitro.

The chimeric tyrosine recombinase, such as a chimeric Flp-TAL recombinase, encoded by the nucleic acids of the invention may have a range of specificities in each of the encoded domains of the chimeric recombinase. For example, the tyrosine recombinase variant domain may be broadly specific, specific, very specific, highly specific, or stringently specific for it target sequence. In the case of Flp, for example, that sequence is denoted FRT. Thus, the for the chimeric Flp-TAL recombinases of the invention, the target sequence for the Flp variant domain will generally be a FRT-like sequence.

Similarly, the TAL DNA-binding domain encoded by the nucleic acids of the invention may also be specific, very specific, highly specific, or stringently specific for it's target sequence. Generally, that target sequence will be upstream or downstream of the target sequence of the recombinase domain. In certain instances, the sequences targeted by the tyrosine recombinase domain and the TAL DNA-binding domains will be separated from one another (upstream or downstream) by 3-12 bp. Generally, the length of the target nucleic acid sequence for the encoded TAL DNA-binding domain of the chimeric recombinase will be a nucleic acid sequence about 9-24 bp, 12-24 bp, or 15-24 bp in length, though in certain instances the recognition sequence may be from about 9 bp or up to about 35 bp.

The invention further provides a nucleic acid encoding a chimeric tyrosine recombinase, such as a chimeric Flp-TAL recombinase, where the encoded recombinase variant domain has broad or relaxed target sequence specificity relative to the wild-type recombinase. In such instances the target specificity of the chimeric tyrosine recombinase may be driven substantially by the sequence to which the TAL DNA-binding domain has been programmed.

The invention further provides a nucleic acid encoding a chimeric tyrosine recombinase, such as a chimeric Flp-TAL recombinase, where the encoded TAL DNA-binding domain stabilizes the binding of the encoded chimeric recombinase on its target sequence and enhances the recombinase activity of the encoded tyrosine recombinase domain.

In certain embodiments, the invention further provides a nucleic acid encoding a chimeric tyrosine recombinase, such as a chimeric Flp-TAL recombinase, where the encoded chimeric recombinase is able to recombine a target sequence in a prokaryotic cell. The invention also provides a nucleic acid encoding a chimeric tyrosine recombinase, such as a chimeric Flp-TAL, where the chimeric recombinase is able to recombine a genomic target sequence in a eukaryotic cell.

In those embodiments of the invention, where nucleic acid encodes a chimeric Flp-TAL recombinase, the encoded Flp variant domain may contain at least 2, 3, 4, 5, 6, 7, 8, or 9 amino acid substitutions selected from the group consisting of A35T, I45V, T50A, A55H, A55S, S59G, S59N, S114P, K173R, I295F, A363E. In some embodiments of the invention, the nucleic acid encodes a chimeric Flp-TAL recombinase where the encoded Flp variant domain may contain at least 3, 4, 5, or all 6 amino acid substitutions selected from the group consisting A35T, I45V, T50A, S114P, I295F, and A263E. In some embodiments of the invention, the nucleic acid encodes a chimeric Flp-TAL recombinase where the encoded Flp variant domain may contain at least 2, 3, 4, 5, 6, 7, 8, 9, 10, 11, 12, or all 13 amino acid substitutions selected from the group consisting of A35T, M44V, T50A, A55H, S59G, K75R, S114P, I157V, K173R, S193G, I295F, and A363E. In some embodiments of the invention, the nucleic acid encodes a chimeric Flp-TAL recombinase where the encoded Flp variant domain may contain at least 2, 3, 4, 5, 6, 7, 8, 9, 10, 11, 12, 13, or all 14 amino acid substitutions selected from the group consisting of Q3R, Q18R, A35T, I45V, T50A, A55H, S59G, K85E, S114P, K173R, L285H, I295F, A324I, and A363E. In some embodiments of the invention, the nucleic acid encodes a chimeric Flp-TAL recombinase where the encoded Flp variant domain may contain at least 2, 3, 4, 5, 6, 7, 8, 9, 10, 11, 12, 13, 14, or all 15 amino acid substitutions selected from the group consisting of A35T, I45V, T50A, A55S, M58V, S59N, T62S, S114P, S130P, F171S, T176A, V213E, N290S, I295F, and A363E.

The invention also provides a nucleic acid encoding a chimeric Flp-TAL recombinase, where the encoded Flp variant domain is evolved from a library Flp genes where genes bearing common as well as unique mutations are used as templates for generating shuffled variant libraries which can be screened to identify the desired target specificity. In some embodiments, those common mutations may be selected from one or more of A35T, I45V, T50A, S114P, I295F, and A263E. In certain embodiments of the invention, the nucleic acid may encode a chimeric Flp-TAL recombinase, where the encoded Flp variant domain is also (or alternatively) evolved from a library Flp genes that are randomized at codons 55, 58 and 59.

In those embodiments of the invention where the nucleic acid encodes a chimeric Flp-TAL recombinase, the encoded Flp variant domain may be a domain identified in a screening system using a reporter construct bearing FRT and FRT-like sequences.

The invention also provides a nucleic acid encoding a chimeric tyrosine recombinase, such as a chimeric Flp-TAL recombinase, where the TAL DNA-binding domain encoded by the nucleic acid is a truncation of the N-terminus and/or the C-terminus of the full TAL effector amino acid sequence. In some such embodiments, the encoded TAL DNA-binding domain is the core TAL DNA-binding domain that begins at position +152 of the N-terminus of the TAL effector and ends at the position +95. In some embodiments, however, it may be advantageous for the encoded TAL DNA-binding domain to include amino acid sequences from the TAL effector extending from beyond the N-terminus and/or the C-terminus of the core TAL DNA-binding domain. In some of those instances, the TAL effector amino acid sequence extending from the N-terminus and/or the C-terminus of the core TAL DNA-binding domain of the TAL effector may function as a linker between the tyrosine recombinase variant domain and the TAL DNA-binding domain.

The invention also provides a nucleic acid encoding a chimeric tyrosine recombinase, such as a chimeric Flp-TAL recombinase, where the recombinase variant domain portion of the encoded chimeric recombinase has broad specificity to more than one recombination sequence and target specificity of the chimeric recombinase is primarily driven by the specificity of the TAL DNA-binding domain. In certain of the embodiments where the encoded Flp recombinase variant domain is broadly specific for a multiplicity of FRT-like target sequences, the nucleic acid may encode a chimeric Flp-TAL recombinase where the TAL DNA-binding domain is programmed to be specific, very specific, highly specific, or strictly specific for a target sequence. In certain instances, those target sequences may be separated from one another by 3-12 bp.

The invention also provides a nucleic acid encoding a chimeric tyrosine recombinase, such as a chimeric Flp-TAL recombinase, where the encoded isolated Flp variant domain is unable to efficiently recombine a genomic target sequence (such as a FRT-like genomic target sequence) in the absence of the TAL DNA-binding domain.

The invention also provides a nucleic acid encoding a chimeric tyrosine recombinase, such as a chimeric Flp-TAL recombinase, where both the encoded recombinase variant domain and the encoded TAL-DNA binding domain are evolved or programmed to be specific, very specific, highly specific, or strictly specific for their respective target sequences. In some instances, those target sequences may be separated from one another by 3-12 bp.

The nucleic acids of the invention may be most conveniently utilized when in the form of a nucleic acid vector. Suitable vectors are well known in the art and may be selected according to the particular application. Nucleic acid vectors may include reporter genes, as appropriate.

In some embodiments, the nucleic acids of the invention may include one or more FRT or FRT-like sites (or the corresponding recombination sites when using other tyrosine recombinases). In some instances, it may be advantageous for the nucleic acids to include a pair of FRT and/or FRT-like sites (or their corresponding equivalents). In some such instances, the pair of FRT and/or FRT-like sites may be arranged in a head to head orientation. In other instances, the pair of FRT and/or FRT-like sites may be arranged in a head to tail orientation. In those instances where the vector is an inversion reporter construct, a reporter may be located between a pair of FRT and/or FRT-like sites oriented in a head to head orientation such that a successful inversion recombination event orients the reporter such that it is expressed. In those instances where the vector is an deletion reporter construct, a reporter may be located between a pair of FRT and/or FRT-like sites oriented in a head to tail orientation. In certain embodiments of the invention, any of the nucleic acids and vectors of the invention may also include a selectable marker.

In some embodiments, the invention provides a composition having a pair of vectors where each vector encodes a different chimeric tyrosine recombinase, such as a Flp-TAL recombinase. In such embodiments, typically the first encoded chimeric tyrosine recombinase (such as a chimeric Flp-TAL recombinase) is encoded on a first vector and contains an encoded TAL DNA-binding domain that is specific, very specific, highly specific, or stringently specific for a nucleic acid sequence upstream of a target recombination sequence (such as a FRT-like sequence) and the second encoded chimeric tyrosine recombinase (such as a chimeric Flp-TAL recombinase) is encoded on a second vector and contains an encoded TAL DNA-binding domain that is specific, very specific, highly specific, or stringently specific for a nucleic acid sequence downstream of the recombination target sequence (such as a FRT-like sequence).

The invention also provides a chimeric Flp-TAL recombinase polypeptide system comprising at least two different chimeric Flp-TAL recombinase polypeptides, wherein each of said chimeric Flp-TAL recombinase polypeptides contains a Flp recombinase domain, a linker peptide, and a TAL DNA binding domain, wherein the first of the two different chimeric Flp-TAL recombinase polypeptides binds on a first side of a target nucleic acid sequence in a cell and the second of the two different chimeric Flp-TAL recombinase polypeptides binds on a second side of the target nucleic acid sequence in the cell, forming a nucleic-acid protein complex, whereby the target nucleic acid sequence is altered.

The invention also provides a chimeric Flp-TAL recombinase nucleic acid system comprising at least one nucleic acid vector having a first regulatory element operable in a target cell, where the first regulatory element is operably linked to a nucleotide sequence encoding a first chimeric Flp-TAL recombinase protein, where the first chimeric Flp-TAL recombinase protein contains a first Flp variant recombinase domain, an optional first linker peptide, and a first TAL DNA-binding domain, where the first Flp variant recombinase domain (or the first linker peptide) operably connects the first Flp recombinase domain to the first TAL DNA-binding domain, and a second regulatory element operable in a target cell, where the second regulatory element is operably linked to a nucleic acid encoding a second chimeric Flp-TAL recombinase protein, where the second chimeric Flp-TAL recombinase protein contains a second Flp recombinase domain, an optional second linker peptide, and a second TAL DNA-binding domain, where the second Flp recombinase variant domain (or the second linker peptide) operably connects the second Flp recombinase domain to the second TAL DNA-binding domain, where the first TAL DNA-binding domain of the first of the two different chimeric Flp-TAL recombinase polypeptides binds on a first side of a target nucleic acid sequence in a cell and the second TAL DNA-binding domain of the two different chimeric Flp-TAL recombinase polypeptides binds on a second side of the target nucleic acid sequence in the cell, forming a nucleic acid-protein complex, whereby the target nucleic acid sequence is altered.

The invention also provides a method of altering a target sequence in the genome of a target cell that comprises introducing into the target cell and expressing a chimeric Flp-TAL recombinase nucleic acid system, where the system comprises at least one nucleic acid vector having a first regulatory element operable in the target cell, where the first regulatory element is operably linked to a nucleotide sequence encoding a first chimeric Flp-TAL recombinase protein, and the first chimeric Flp-TAL recombinase protein contains a first Flp recombinase variant domain, an optional first linker peptide, and a first TAL DNA-binding domain, where the first Flp recombinase variant domain (or the optional linker peptide) operably connects the first Flp recombinase domain to the first TAL DNA-binding domain, and a second regulatory element operable in said target cell, where the second regulatory element is operably linked to a nucleotide sequence encoding a second chimeric Flp-TAL recombinase protein, and the second chimeric Flp-TAL recombinase protein contains a second Flp recombinase variant domain, an optional second linker peptide, and a second TAL DNA binding domain, where the second Flp recombinase variant domain (or the optional second linker peptide) operably connects the second Flp recombinase domain to the second TAL DNA-binding domain, where the first TAL DNA-binding domain targets a nucleic acid sequence on a first side of the target sequence and said second TAL DNA-binding domain targets a nucleic acid sequence on a second side of the target sequence forming a nucleic acid-protein complex, whereby the target nucleic acid sequence in the cell is altered. The invention also provides methods where the alteration in the target nucleic sequence is and inversion, a deletion, or dual RMCE.

The invention also provides a method of altering a target sequence in the genome of a target cell that comprises introducing into the target cell a chimeric Flp-TAL recombinase polypeptide system, said system comprising a first chimeric Flp-TAL recombinase protein and a second chimeric Flp-TAL recombinase protein, each of said chimeric Flp-TAL recombinase proteins containing a Flp recombinase variant domain, an optional linker peptide, and a TAL DNA-binding domain, where the Flp recombinase variant domain (or the optional linker peptide) operably connects the Flp recombinase variant domain to the TAL DNA-binding domain, where the TAL DNA-binding domain of the first chimeric Flp-TAL recombinase protein targets a nucleic acid sequence on a first side of the target sequence and the TAL DNA-binding domain of the second chimeric Flp-TAL recombinase protein targets a nucleic acid sequence on a second side of the target sequence and forming a nucleic acid-protein complex, whereby introduction of said first and second chimeric Flp-TAL recombinases in said target cell alters the target sequence of the target cell. The invention also provides methods where the alteration in the target nucleic sequence is an inversion, a deletion, or dual RMCE.

BRIEF DESCRIPTION OF THE DRAWINGS

FIG. 8: Nucleic acid sequences and graphical representations of the recombination targets that are located in the vectors. These recombination targets help the vectors to integrate into the genomic FRT-like sequences FL-61 (SEQ ID NO 34), FL-63 (SEQ ID NO 35), and FL-71 (SEQ ID NO 36), respectively.

FIG. 9: Amino acid sequence and graphical representation of a representative TAL DNA-binding domain (SEQ ID NO 15).

FIG. 10: Amino acid sequence and graphical representation of a representative Flp-TAL recombinase (SEQ ID NO 37).

FIG. 11: Graphical representation of FL-71 Left TAL sequences of different lengths (SEQ ID NO 21), (SEQ ID NO 44), (SEQ ID NO 45).

FIG. 12: Graphical representation of loxP-like sequence 69058 (LL-69), with different TAL sequences (SEQ ID NO 55), (SEQ ID NO 41), (SEQ ID NO 42), (SEQ ID NO 43).

FIG. 13: Graphical representation of partial coding sequence for chimeric iCreM24/69-TAL recombinase (SEQ ID NO 40).

DETAILED DESCRIPTION OF THE INVENTION

Figure 1:
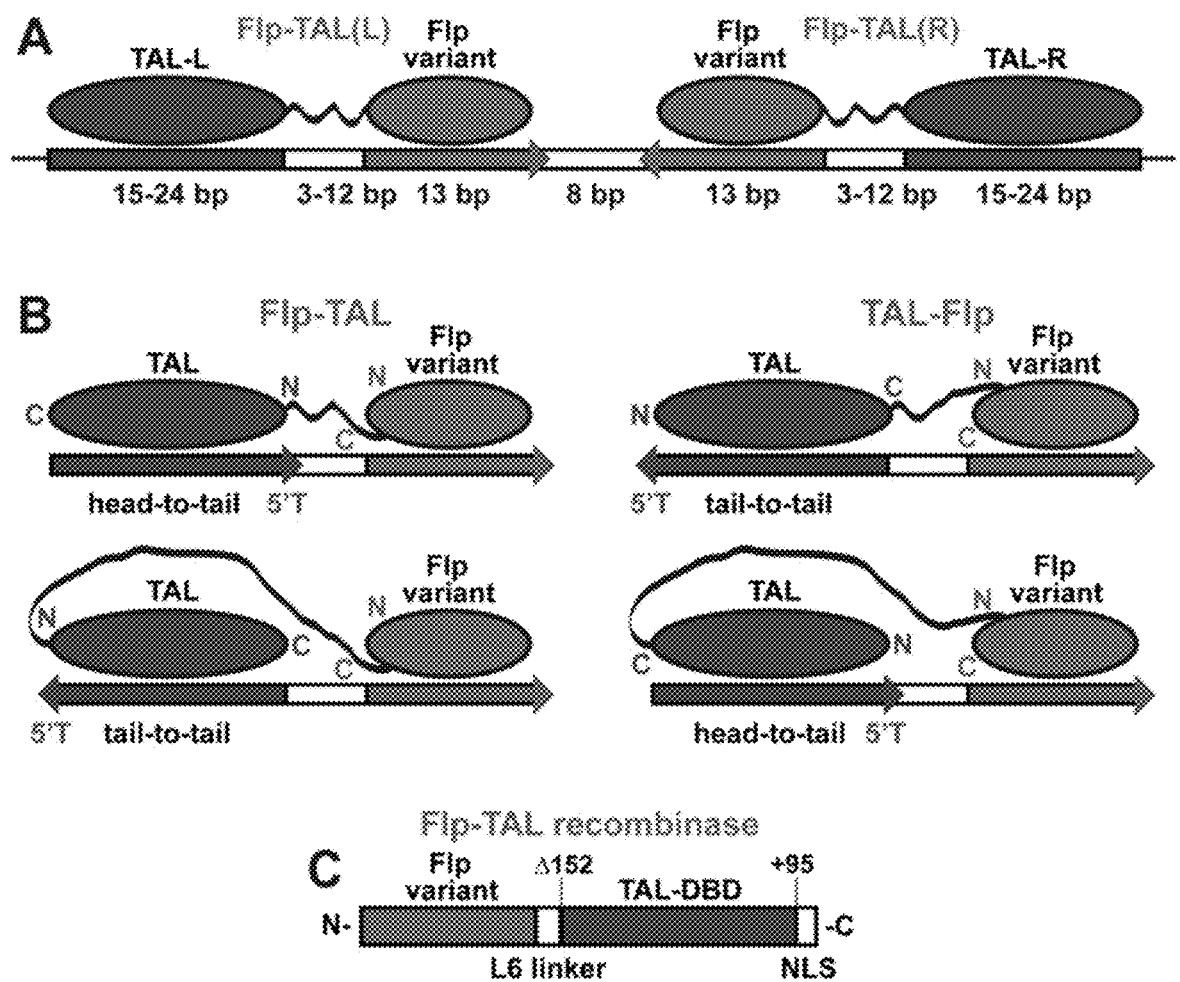
FIG. 1: Flp-TAL recombinases. Panel (A) shows a general mode of target binding by Flp-TAL recombinases. Panel (B) shows the possible relative arrangements of the Flp and TAL recognition sequences and the connections between the Flp and TAL modules. Panel (C) shows an example schematic of a Flp-TAL recombinase.

The present invention applies a different approach to develop tyrosine recombinases with a desired target specificity. In this approach, a chimeric tyrosine recombinase is utilized that has two modules; one to help direct target binding and another for the catalytic function. In this approach, a tyrosine recombinase variant is fused with a DNA binding domain (DBD), the target specificity of which can be readily. The addition of the target-specific DNA binding domain helps to stabilize the recombinase variant on its target, thereby simplifying the process of reprogramming the target specificity of a tyrosine recombinase and increasing the activity of the chimeric recombinase relative to that of the recombinase module alone.

The present invention offers several advantages over existing compositions and methods for altering the genome of a target cell. First, unlike serine recombinases such as Cas9, the tyrosine recombinases utilized in the present invention do not rely on host cell DNA repair machinery to repair the strand breaks that occur during the recombination event. As such, the present invention is able to be utilized on cells that are not actively replicating, regardless of whether the host cell repair machinery is active or not. Second, unlike serine recombinases, tyrosine recombinases make single-stranded breaks (rather than double-stranded breaks), reducing the likelihood of unintended gross rearrangements of the genome. Moreover, the present invention utilizes tyrosine recombinases that have a greater number of potential target sites well distributed throughout the genome than, for example, the CRISPR/Cas9 system. Lastly, the present invention provides a method of targeting alterations in a genome with exceptional accuracy, with a lower potential for recombining at an unintended "off target" site than systems such as CRISPR/Cas9.

Definitions: In general, throughout this specification, terms are intended to be interpreted as they are understood by a person of ordinary skill in the art. However, the following terms may be more clearly understood by reference to the following definitions:

The term "wild-type" as used herein refers to a typical form of an organism, strain, nucleic acid, gene, protein, polypeptide, or characteristic as it occurs in nature.

The term "variant" as used herein refers to a mutated, artificially evolved, or other form of an organism, strain, gene, nucleic acid, protein, polypeptide, or characteristic that differs in some manner from the corresponding wild-type organism, strain, gene, nucleic acid, protein, polypeptide, or characteristic.

The term "chimeric" as used herein refers to a gene, coding region, nucleic acid, protein, or polypeptide that contains part or all of at least two genes, coding regions, nucleic acids, proteins, and/or polypeptides, that do not naturally exist together as such and have been assembled together to form a gene, coding region, nucleic acid, protein, polypeptide or combination thereof that does not naturally exist in nature.

The term "heterologous" as used herein is a term of art understood to refer to a nucleic acid or polypeptide sequence that is not naturally found with the wild-type nucleic acid, gene, protein, or polypeptide.

The term "tyrosine recombinase" as used herein refers to a group of enzymes that perform site-specific recombination in a manner that involves a tyrosine residue in the recombinase forming a covalent protein-DNA linkage in the reaction intermediate. Tyrosine recombinases break and rejoin single strands in pairs and form a Holliday junction intermediate. Examples of tryosine recombinases include the Flp recombinase from the 2u plasmid of *Saccharomyces cerevisiae* (as well as the thermostable variant of Flp, Flpe (SEQ ID NO 1; SEQ ID NO 2)) the Cre recombinase of bacteriophage P1 (as well as the codon optimized form of Cre, iCre (SEQ ID NO 3; SEQ ID NO 4)), the B2 recombinase from the pSB2 plasmid of *Zygosaccharomyces bailii* (SEQ ID NO 5), the B3 recombinase from the pSB3 plasmid of *Zygosaccharomyces rouxii* (SEQ ID NO 6), the KD recombinase from the pKD1 plasmid of *Kluyveromyces drosophilarum* (SEQ ID NO 7), the KW recombinase from the pKWS1 plasmid of *Kluyveromyces waltii* (SEQ ID NO 8), the R recombinase from the pSR1 plasmid of *Zygosaccharomyces rouxii* (SEQ ID NO 9), the SM recombinase from the pSM1 plasmid of *Zygosaccharomyces fermentati* (SEQ ID NO 10), the TD recombinase from the pTD1 plasmid of yeast *Torulaspora delbrueckii* (SEQ ID NO 11), λ Int, and others. Tyrosine recombinases are distinct from serine recombinases, such as Gin, Hin and others, where a serine residue in the recombinase forms a covalent protein-DNA linkage during the reaction intermediate and all strands are cut prior to strand exchange.

The terms "specific" or "specificity" as used herein refers to the property of having a degree of preference for recognizing, binding, hybridizing, recombining, or reacting with a desired target or substrate versus one or more non-desired targets or substrates under the conditions tested or specified.

In general, the terms "specific for" or having "specificity for" is used to refer to a preference of at least 50% for the desired target or substrate versus two or more non-desired targets or substrates collectively or for at least a 4:1 preference for the desired target or substrate versus a particular undesired target or substrate under the conditions tested or specified. The related term "very specific for" is used to refer to a preference of at least 80% for the desired target or substrate versus two or more non-desired targets or substrates collectively or for at least a 10:1 preference for the desired target or substrate versus a particular undesired target or substrate. The related terms "highly specific for" as used herein is used to refer to a preference of at least 90% for the desired target or substrate versus two or more non-desired targets or substrates collectively or for at least a 20:1 preference for the desired target or substrate versus a particular undesired target or substrate. The related term "strictly specific for" or having "strict specificity" as used herein is used to refer to a preference of at least 98% for the desired target or substrate versus two or more non-desired targets or substrates collectively or for at least a 100:1 preference for the desired target or substrate versus a particular undesired target or substrate. The related terms "completely specific for" or "complete specificity" are used herein to refer to a target or substrate preference of such a degree that no other binding, hybridization, or reaction is detectable under the conditions specified. Note that "completely specific for" and "complete specificity" are not intended to suggest that recognizing, binding, hybridizing, recombining, or reacting with an undesired target or substrate does not occur at all, but rather, that it does not occur beyond a barely detectable level under the conditions tested or specified. The words specific and specificity may be used interchangeably. Each of these levels of specificity may be referred to collectively as "narrow specificity."

In contrast, the terms "broadly specific for" or having "broad specificity" or "relaxed specificity" as used herein refers to the characteristic of being able to recognize, bind, hybridize, recombine, or react with a group of two or more desired potential targets or substrates such that each desired potential target or substrate is at least 75% utilized under the conditions tested or specified.

The terms "TAL DNA-binding domain" or "TAL DBD" as used herein refers to a polypeptide having the core TAL effector DNA-binding domain, which is located between position +152 (Δ152 truncation of the N-terminal segment of the TAL effector) and position +95 of the C-terminal segment of the TAL effector. See e.g., Miller J C, et al. (2011) A TALE nuclease architecture for efficient genome editing. Nat Biotechnol 29(2):143-148.

Chimeric tyrosine recombinases of the invention: Two classes of the chimeric tyrosine recombinases are contemplated as within the scope of the invention that, broadly speaking, differ at the level of the target specificity of their recombinase modules. In the first class of chimeric tyrosine recombinases, both modules of the chimeric recombinase (the tyrosine recombinase variant module and the extra DNA binding domain module) are evolved or engineered to be specific, very specific, highly specific, strictly specific, or completely specific for the particular genomic target sequence of interest. As such, this class of chimeric tyrosine recombinases represents what is perhaps the most target specific genome engineering tool presently available. Although modification of the target specificity of both the recombinase module and the DNA binding module can require more effort than that of the second class (described below), the amount of effort required is still quite manageable.

In the second class of chimeric tyrosine recombinases, the two modules can differ at the level of their target specificity such that a recombinase variant is evolved or utilized that has a somewhat relaxed or broad specificity toward a genomic target sequence (as compared to the wild-type recombinase), while the extra TAL DNA-binding module is engineered to be specific, very specific, highly specific, strictly specific or completely specific for a sequence to the left or right of the recombinase target sequence, so as to deliver the recombinase module to the particular target sequence where the recombination reaction is intended to take place. As the target specificity of the recombinase module is relatively broad, the recombinase module can be used to generate hybrid recombinases of different target specificity simply by changing the target specificity of the extra DNA binding module. Since the target specificity of the DNA-binding can be readily programmed, the effort to modify the target specificity of this class of chimeric tyrosine recombinases is relatively low.

The functional properties of chimeric tyrosine recombinases having a broad or relaxed specificity, are expected to be somewhat different. Since, ideally, the recombinase module should be able to recombine many, if not the majority of the high-scoring target-like sequences, target specificity of the respective chimeric tyrosine recombinases should be easily modified since all that will be required is the assembly of new TAL modules. On the other hand, the relaxed target specificity of this tyrosine recombinase module necessarily reduces specificity of these chimeric tyrosine recombinases. Nevertheless, even reduced, target specificity of these chimeric recombinases is expected to be sufficiently high to target just the sequences of interest since, as explained below, in addition to the target specificity of the two TAL modules (See e.g. Flp-TAL (FIG. 1A)), target specificity of the tyrosine recombinase module as well as the functional specificity of the target-like sequence spacer will also contribute to the overall chimeric tyrosine recombinase specificity.

Taking Flp as a representative example, target specificity of the Flp module with relaxed specificity reflects the sequence characteristics of the FRT-like sequences that differ them from a random nucleic acid sequence. In mammalian genomes, these sequence characteristics translate into one FRT-like sequence per about 5,000 base pairs which respectively decreases the probability to find an FRT-like sequence between two TAL binding sequences (FIG. 1A) by about three orders of magnitude.

This probability is further decreased by about three orders of magnitude due to the functional property of the FRT spacer (also called 'strand exchange region', FIG. 2B) that increases the overall recombination specificity of the Flp/FRT system. Although Flp does not make contacts to the spacer, the recombination specificity of the Flp/FRT system depends on the spacer sequence: only FRT variants with the same spacers will efficiently recombine with each other while FRT variants with different spacers will not. Since FRT has an 8-bp spacer, the probability to find a spacer sequence of this length is $1/4^8$ (or $1/65,536$). For the FRT-like sequences this probability is higher: $1/4^6/2$ (or $\sim 1/2,000$) since the first and the last base pairs of the spacer in these sequences are invariant: T/A and A/T, respectively, and the G/C content of the spacer is set to be equal or lower than 50%.

Taken together, the probability of finding an FRT-like sequence with a unique spacer that is located between the two TAL binding sequences is $\sim 1/10^7$ ($\sim 1/(5 \times 10^3) \times \sim 1/(2 \times 10^3)$) which ensures that the TAL-guided Flp variant with relaxed specificity toward FRT-like sequences will recombine just the sequence of interest. This, however, can only be realized if the tyrosine recombinase module of the chimeric tyrosine recombinase is not sufficiently active to recombine target-like sequences on its own, without the target stabilization effect by the TAL module. It is therefore important that tyrosine recombinase variants with relaxed target specificity are evolved to have a relatively low recombination activity as compared to their wild-type counterparts. Generally, when the activity of these recombinase variants is in the range of about 25 to about 50% relative to their wild-type counterparts, they are essentially inactive in a eukaryotic cell without the support of the TAL DBD.

Herein, we describe both classes of chimeric tyrosine recombinases and their use in genome engineering, primarily as exemplified by chimeric recombinases composed of variants of the tyrosine recombinase Flp (or Cre), together with a programmed DNA binding domain of the TAL effectors. More particularly, the chimeric Flp-TAL recombinases described herein contain a recombinase domain composed of a variant of the Flp recombinase (with either narrow or broad target specificity), fused directly or indirectly to a DNA binding domain composed of a TAL effector DNA binding domain (TAL DBD), with a linker optionally between the two domains. It will be readily apparent that since the tyrosine recombinases have similar three-dimensional organization, similar mode of target binding, and are well amenable to modification of their target specificity, the other members of the tyrosine recombinase family can be also utilized to generate chimeric TAL-fused tyrosine recombinases essentially as described herein. Moreover, since each recombinase has its own set of target sequences in a genome, these additional tyrosine recombinases can greatly diversify the sequences that can be targeted by the chimeric TAL-fused recombination system. Further, different TAL-fused chimeric tyrosine recombinases can be paired to perform dual RMCE to efficiently replace genome fragments. Importantly, the availability of several target-specific hybrid recombinases for dual RMCE would translate into shorter genome fragments that can be replaced: our analysis of the distribution of the target-like sequences for different recombinases in a genome shows that an arsenal of 5-6 hybrid recombinases is sufficient for reducing the size of the replaceable genomic fragments to about 1 kb.

Although this is believed to be the first use of such an approach with tyrosine recombinases, a somewhat similar approach has been previously applied to create chimeric serine recombinases such as zinc-finger recombinases, or ZFRs, TALE recombinases, or TALERs, and Cas9 recombinases, or recCas9, that were created by fusing the activated catalytic domains of the invertase Gin or the resolvase Tn3 with the DNA binding domains of either zinc fingers, TAL effectors, or the catalytically inactive Cas9 protein, respectively. See Akopian et al., Chimeric recombinases with designed DNA sequence recognition. Proc Natl Acad Sci USA 100(15):8688-8691 (2003), Gordley et al., Evolution of programmable zinc finger-recombinases with activity in human cells. J Mol Biol 367(3):802-813 (2007); Mercer et al., Chimeric TALE recombinases with programmable DNA sequence specificity. Nucleic Acids Res 40(21):11163-11172 (2012); and Chaikind et al., A programmable Cas9-serine recombinase fusion protein that operates on DNA sequences in mammalian cells. Nucleic Acids Res 44(20):9758-9770 (2016).

A modular design approach, in which proteins with different functional properties are fused together, has also previously been employed to develop hybrid site-specific nucleases: zinc finger nucleases (ZFNs), and transcription activator-like effector nucleases (TALENs), that are composed of a nonspecific DNA nuclease FokI and the respective DNA binding domains with programmable target specificity. Kim et al., Hybrid restriction enzymes: zinc finger fusions to Fok I cleavage domain. Proc Natl Acad Sci USA 93(3):1156-1160 (1996); Christian et al., Targeting DNA double-strand breaks with TAL effector nucleases. Genetics 186(2):757-761 (2010). Target affinity and specificity in these modular systems can be modified by changing the number of the target recognizing units in their DNA binding domains to achieve the optimal balance between target specificity and non-specific DNA binding. See Miller et al., A TALE nuclease architecture for efficient genome editing. Nat Biotechnol 29(2):143-148 (2011); Porteus et al., Gene targeting using zinc finger nucleases. Nat Biotechnol 23(8): 967-973 (2005); Urnov et al., Highly efficient endogenous human gene co/*rrection using designed zinc-finger nucleases. Nature 435(7042):646-651 (2005); Miller et al., An improved zinc-finger nuclease architecture for highly specific genome editing. Nat Biotechnol 25(7):778-785 (2007); Cermak et al., Efficient design and assembly of custom TALEN and other TAL effector-based constructs for DNA targeting. Nucleic Acids Res 39(12):e82 (2011); Gaj et al., ZFN, TALEN, and CRISPR/Cas-based methods for genome engineering. Trends Biotechnol 31(7):397-405 (2013).

As noted, suitable tyrosine recombinase variants for use in the present compositions and methods include, for example, variants of the Flp recombinase from the 2u plasmid of *Saccharomyces cerevisiae* (including the thermostable form of Flp, Flpe (SEQ ID NO 1; SEQ ID NO 2), variants of the Cre recombinase of bacteriophage P1 (including the codon optimized iCre (SEQ ID NO 3; SEQ ID NO 4), variants of the R recombinase from the pSR1 plasmid of *Zygosaccharomyces rouxii* (SEQ ID NO 9), variants of the B2 recombinase from the pSB2 plasmid of yeast *Zygosaccharomyces bailii* (SEQ ID NO 5), variants of the B3 recombinase from the pSB3 plasmid of *Zygosaccharomyces rouxii* (SEQ ID NO 6), variants of the KD recombinase from the pKD1 plasmid of *Kluyveromyces drosophilarum* (SEQ ID NO 7), variants of the KW recombinase from the pKWS1 plasmid of *Kluyveromyces waltii* (SEQ ID NO 8), variants of the SM recombinase from the pSM1 plasmid of *Zygosaccharomyces fermentati* (SEQ ID NO 10), and variants of the TD recombinase from the pTD1 plasmid of yeast *Torulaspora delbrueckii* (SEQ ID NO 10). Suitable variants of these recombinases will generally have at least 80, 85, 90, or 98 percent amino acid homology to at least the enzymatically active portion of their respective wild-type recombinase enzymes.

Suitable tyrosine recombinase variants may also include deletions mutants, thermostable variants, split recombinase proteins (such as described in Jullien et al., (2003) Nucleic Acids Research, Regulation of Cre recombinase by ligand-induced complementation of inactive fragments, Vol. 31, No. 21:e131; Kawano et al. (2016), A photoactivatable Cre-loxP recombination system for optogenetic genome engineering, dOI: 10.1038/nCHeMBIO.2205; and Jun et al. (2019) Noninvasive optical activation of Flp recombinase for genetic manipulation in deep mouse brain regions, Nature Communications, doi.org/10.1038/s41467-018-08282-8), fusions proteins, and the like.

Flp: Flp is a tyrosine recombinase, originally isolated from *Saccharomyces cerevisiae*. In yeast, Flp is found on the 2 plasmid, where it promotes an inversion of the DNA between two 599-bp inverted repeats. Flpe is a thermostable form of Flp and may form a suitable basis for further evolution of Flp variants. (SEQ ID NO 1; SEQ ID NO 2) See Mol Biotechnol. 2011 September; 49(1)82-9. The minimal recombination site, known as the Flippase Recombinase Target (FRT), is composed of two inverted 13 bp arms, separated by an 8 bp spacer. The sequence recognized by the wild-type enzyme is 5'GAAGTTCC-TATACtttctagaGAATAGGAACTTC3'. (SEQ ID NO 12).

However, Flp variants are known and can be readily evolved that recognize FRT-like sequences. FRT-like sequences differ from the wild-type recognition sequence at one or more locations from FRT and are widely represented in the genome of mammalian cells. See Bolusani S, et al. (2006) Evolution of variants of yeast site-specific recombinase Flp that utilize native genomic sequences as recombination target sites. Nucleic Acids Res 34(18):5259-5269, Shultz et al., A genome-wide analysis of FRT-like sequences in the human genome. PLoS One 6(3):e18077 (2011), Shah et al., Li F, Voziyanova E, & Voziyanov Y (2015) Target-specific variants of Flp recombinase mediate genome engineering reactions in mammalian cells. The FEBS journal 282(17):3323-3333.

The Flp variants suitable for the chimeric Flp-TAL recombinases of the invention may either have a narrow target specificity or a somewhat relaxed broader target specificity. Flp variants that are specific, very specific, highly specific, strictly specific, or completely specific will generally be most useful for those embodiments of the invention that utilize a chimeric recombinase of the first class. Flp variants having a somewhat relaxed and broad specificity will be those embodiments of the invention that utilize a chimeric Flp-TAL recombinase of the second class.

Flp variants suitable for the chimeric Flp-TAL recombinases of the invention will typically have at least 80, 85, 90, 95, or 98 percent amino acid homology to the wild type Flp enzyme. Typically, suitable Flp variants will contain at least 2, 3, 4, 5, 6, 7, 8, or 9 of the following amino acid substitutions: A35T, I45V, T50A, A55H, A55S, S59G, S59N, S114P, K173R, I295F, A363E. Most typically, suitable Flp variants will contain at least 3, 4, 5, or all 6 of the following amino acid substitutions: A35T, I45V, T50A, S114P, I295F, and A263E. One specific example of a suitable Flp variant contains the following amino acid substitutions: A35T, M44V, I45V, T50A, A55H, S59G, K75R, S114P, I157V, K173R, S193G, I295F, and A363E. Another specific example of a suitable Flp variant contains the following amino acid substitutions: Q3R, Q18R, A35T, I45V, T50A, A55H, S59G, K85E, S114P, K173R, L285H, I295F, A324I, and A363E. Another specific example of a suitable Flp variant contains the following amino acid substitutions: A35T, I45V, T50A, A55S, S59N, T62S, S114P, S130P, F171S, T176A, V213E, N290S, I295F, and A363E. Without intending to be bound by any particular theory, it is believed that these amino acid substitutions contribute to allowing the Flp variants to recognize different FRT-like sequences in the genome. Additional mutations and amino acid substitutions are both permissible and contemplated, as such mutations and substitutions may contribute to relaxing or narrowing the Flp variant's target specificity.

Evolution of suitable target-specific or target-relaxed Flp variants can be facilitated if genes for known Flp variants bearing common as well as unique mutations are used as templates for generating shuffled variant libraries which can be screened to identify the desired target specificity. Examples of such Flp variants are known in the art and are described, for example, in Bolusani et al., Evolution of variants of yeast site-specific recombinase Flp that utilize native genomic sequences as recombination target sites. Nucleic Acids Res. 34(18):5259-5269 (2006), Shultz et al., A genome-wide analysis of FRT-like sequences in the human genome. PLoS One 6(3):e18077 (2011), and Shah et al., Target-specific variants of Flp recombinase mediate genome engineering reactions in mammalian cells. The FEBS journal 282(17):3323-3333 (2015). The pool of the template variant genes can be further enhanced by including in the library Flp genes that are randomized at codons 55, 58 and 59, since the amino acids at these positions contact the first four base pairs of the Flp binding elements of FRT that are known to be the most critical for the Flp-FRT recognition. (Shultz et al. 2011). By following this approach, Flp variants suitable for the Flp-TAL recombinases can be evolved in as little as one or two rounds of protein evolution using a pair of different, but related, recombination sequences such as a genomic FRT-like sequence and FRT.

Most often, the Flp recombinase activity of the variant utilized as the Flp recombinase module in either class of chimeric recombinases is somewhat reduced, as compared to the wild-type recombinase. Generally, the activity of the Flp recombinase variant will retain 75 percent or less, 50 percent or less, or 25 percent or less of the recombinase activity against the FRT-like target to which it was evolved, as compared to the wild type enzyme against its natural target FRT, under the conditions tested in *E. coli* assays, performed essentially the same as in Voziyanov et al., 2002. Briefly, competent cells harboring the recombination reporter pBU are transformed with p33-mFlp (either as individual variants or a mutagenised pool). LB medium (10 g/l NaCl (Sigma), 10 g/l tryptone peptone (Difco) and 5 g/l yeast extract (Difco)) ares added to the cells and Flp variants are expressed by the addition of L-arabinose to a final concentration of 0.1% for 2.5 hours at 37° C. Then cells are then plated on LB-plates (LB plus Bacto Agar (Difco)) supplemented with 100 mg/l ampicillin, 30 mg/l chloramphenicol, and 100-200 mg/l X-gal. Plates are then incubated at 37° C. for 24 hours and the colonies are then scored for their color (blue or white). Without intending to be bound by any particular theory, it is believed that the reduced recombinase activity in the variant utilized as a recombinase module in the chimeric enzyme helps to reduce the probability of undesired recombination of genomic sequences by the catalytic module on its own. In the context of the chimeric enzyme, however, the recombination activity of the recombinase module is enhanced upon binding to the desired target sequence as a result of the target binding stabilization by the TAL DNA binding domain module.

Figure 3:
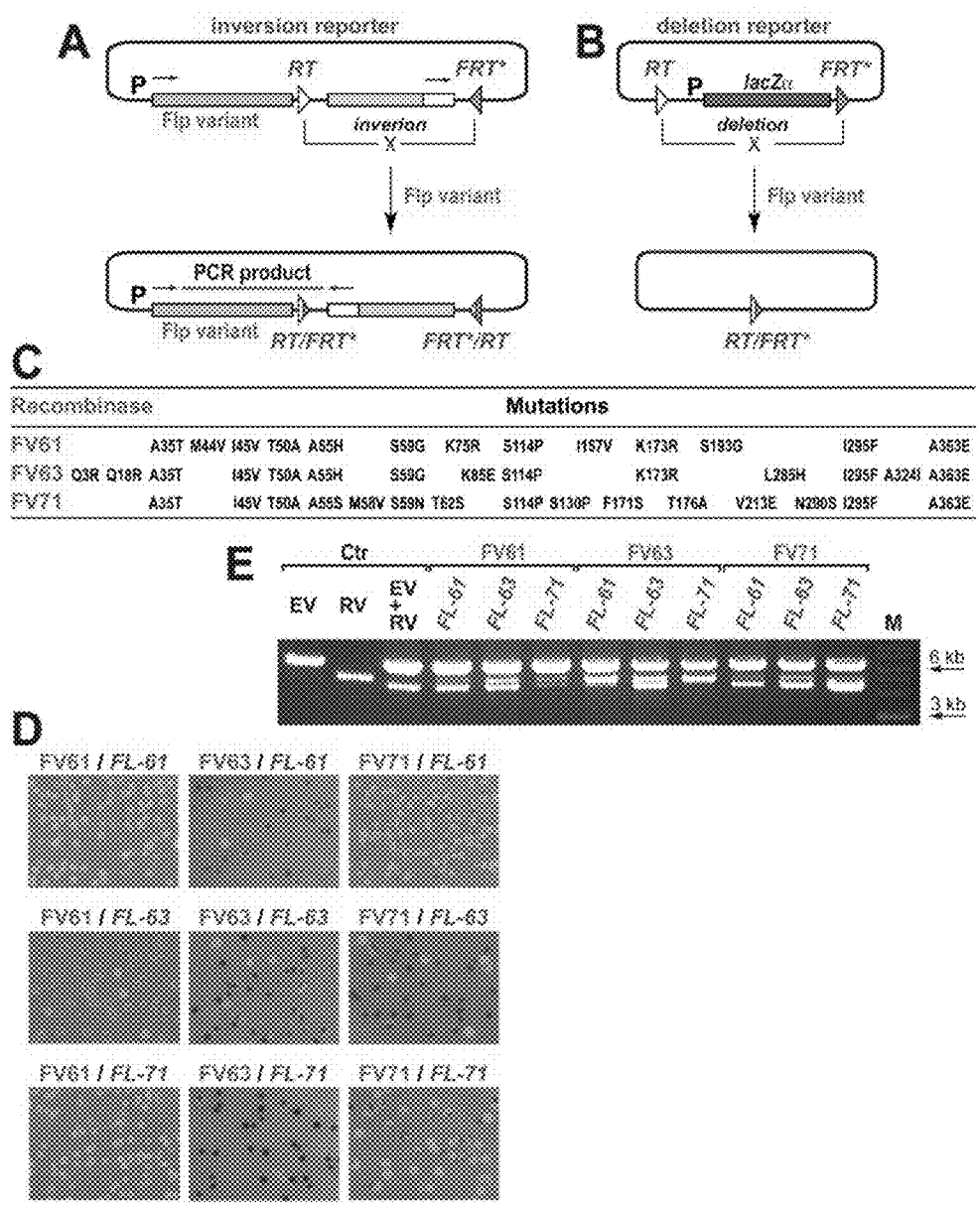
FIG. 3: Evolution of Flp-TAL recombinases. (A) Inversion assay. The reporter contains the inversion cassette flanked by the recombination targets in the head-to-head orientation: FL-61, FL-63, or FL-71 (marked as RT) and FRT* that bears the spacer either from FL-61, FL-63, or FL-71, respectively. Upon expression of a recombination competent Flp variant, the cassette is inverted so the gene that encodes this variant can be amplified. (B) Deletion assay. The deletion reporter has the lacZα cassette flanked by the recombination targets in the head-to-tail orientation. If a Flp variant is able to delete the cassette, the resulting bacterial cells will form white colonies when plated on the X-gal containing plates. (C) Mutations in FV61, FV63, and FV71. (D) Activity of FV61, FV63, and FV71 on the FL-61, FL-63, and FL-71 substrates. The assays were performed using the deletion reporter. (E) Electrophoregram of the uniquely digested plasmid DNA isolated from the colonies poled from the respective plates shown in D. Ctr, control vectors; EV, expression vector; RV, reporter vector; EV+RV, Flpe expression vector and the deletion reporter that bears the lacZα cassette flanked by FRT, which was completely deleted; M, DNA ladder.

Flp variants with the desired properties may be identified, for example, using a screening system that is composed of inversion and deletion reporters that are used sequentially (FIGS. 3A and B). In such a screening system, reporter cassettes in these vectors are flanked by a pair of FRT or FRT-like recombination sites that are arranged in the head-to-head and head-to-tail orientations, respectively. The inversion and deletion reporters have different purpose. The inversion reporter is used to identify a large pool of Flp variants that are able to recombine both the FRT-like sequence and FRT (or two FRT-like sequences); these variants are selected by amplifying the Flp variant genes in the inversion-positive configuration of the reporter (FIG. 3A). The deletion reporter is used to screen the inversion-positive library of the Flp variants that are sufficiently active to delete the reporter cassette in at least some vector molecules (FIG. 3B).

Figure 6:
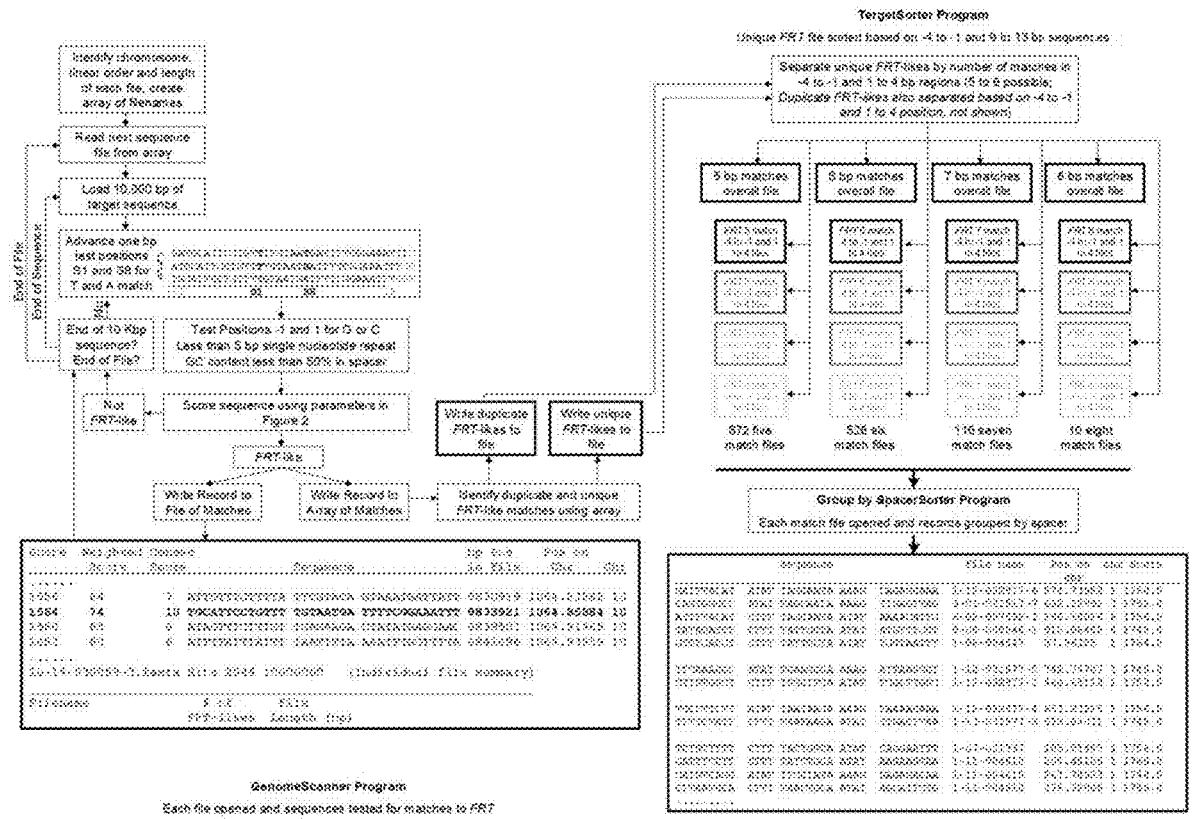
FIG. 6: An overview of the TargetSiteAnalyzer bioinformatics package used to find FRT-like sequences (NCBI build 36.3). Heavy-bordered boxes indicate the creation of a file. File format boxes may have spaces added for readability in this figure (SEQ ID NOS. 54-73).

FRT-like sequences: Suitable target FRT-like sequences in a genome or nucleic acid sequence of interest may be identified using the publicly available program TargetSite-Analzyer. Shultz et al., A genome-wide analysis of FRT-like sequences in the human genome. PLoS One 6(3):e18077 (2011). TargetSiteAnalyzer is composed of three JAVA programs that are sequentially run: GenomeScanner, TargetSorter and SpacerSorter. Together, these programs simplify the task of identifying and then sorting FRT-like sequences within a genome of interest. An overview of these programs and the processing steps is shown in FIG. 6 and described in greater detail in Shultz et al.. The programs were created and executed within the freely b available NetBeans IDE (version 6.8; netbeans.org). The JAVA code for TargetSiteAnalyzer is freely available for download (See Shultz et al.).

GenomeScanner sequentially screens each DNA contig file within a genome build for FRT-like sequences using the rules that describe sites that can serve as functional recombination targets. A contig file is successively read as overlapping 34-nucleotide segments in 1-nucleotide increments. Each 34-nucleotide sequence is separated into three regions (See FIG. 6): two potential inverted recombinase binding elements (positions −13 through −1 and positions 1 through 13) and a spacer (positions s1 through s8). As does Target-Finder, GenomeScanner first checks if a putative spacer has a 'T' at position s1 and an 'A' at position s8 and whether GC content of the spacer equals or is below 50%.

Figure 7:
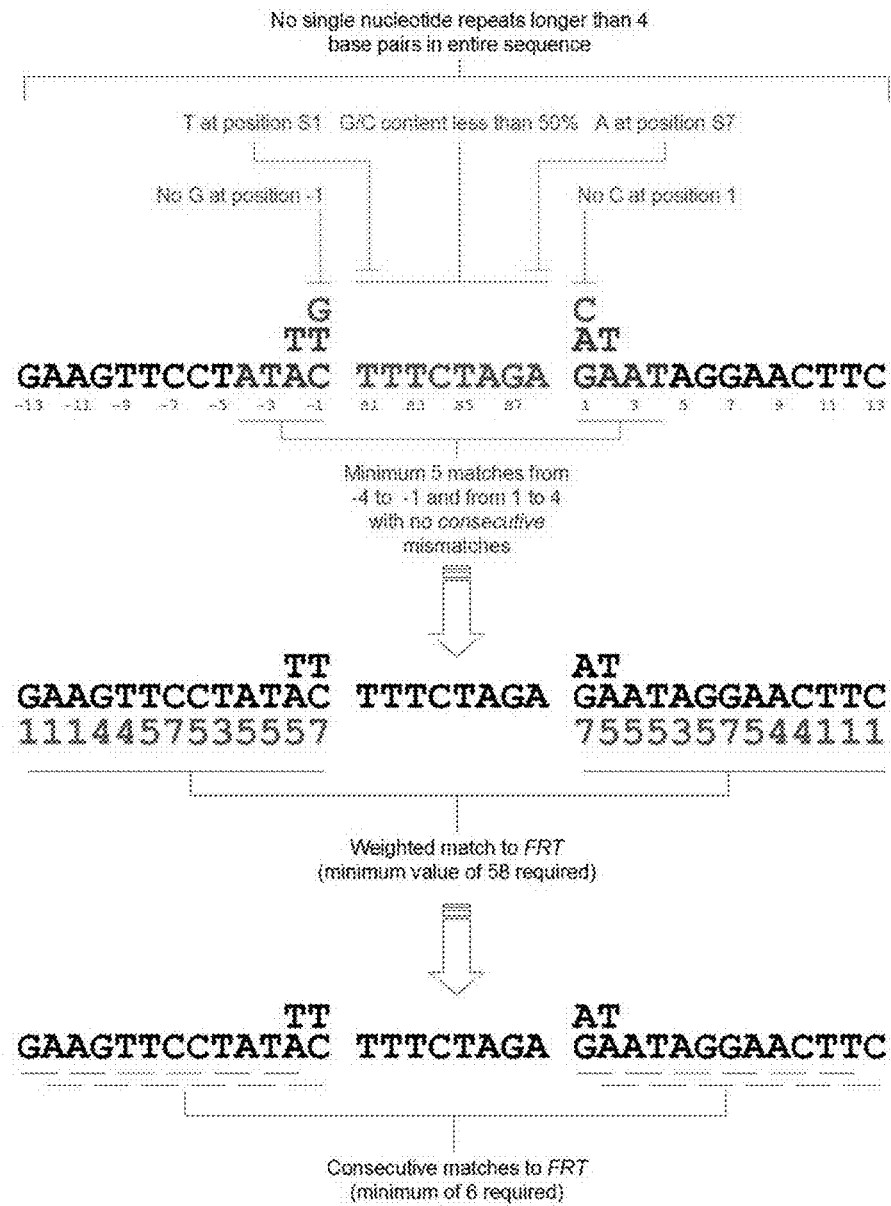
FIG. 7: A graphical representation of some FRT-like sequence identification parameters (relative to the FRT consensus sequence (SEQ ID NO 12).

If these criteria for a functional spacer are met, GenomeScanner tests positions −4 to −1 and 1 to 4 and also −7 and 7 of the putative binding elements of an FRT-like sequence for the number of matches and mismatches to the corresponding positions of FRT. In addition, the entire 34-nucleotide sequence of an FRT-like site is tested for any single nucleotide repeat longer than four nucleotides. The putative binding elements of an FRT-like sequence are also checked for the number of consecutive matches (FIG. 7). Each position in the binding elements of an FRT-like sequence (positions −13 to −1 and 1 to 13) that is matched to the corresponding position in FRT, is given a weighted value and a total score for an FRT-like sequence is generated that includes the number of matches within the 'proximal-8' sequence and the weighted value. Values of 80 or greater are indicative of a functional FRT-like sequence.

During program execution, GenomeScanner writes each match to a linear-order text file and to an internal array. After the last sequence file is processed, GenomeScanner uses the array to determine which FRT-like sequences are unique, then generates two additional output files: one containing only unique FRT-like sequences and a second containing FRT-like sequences with at least one exact duplicate. GenomeScanner reports the position of each identified FRT-like sequence both within the sequence contig files and within a chromosomal fragment map based on linear order of files for each chromosome and the cumulative base pairs for each chromosome.

TargetSorter works with the GenomeScanner generated files that contain both the unique and duplicated FRT-like sequences. The program groups the records based on the sequence of the most functionally important region of the FRT putative recombinase binding elements (−4 to −1 and 1 to 4). In this region, both complimentary strands are assigned a numeric value. The lowest value is used to assign the record to a file.

The SpacerSorter program sorts FRT-like sequences within each output file generated by TargetSorter based on spacer sequence. In similar fashion to the TargetSorter program, both directions of the spacer sequences are used to determine if a match exists. This final sorting step allows identification of those FRT-like sequences that can, in principle, recombine with each other by a single Flp variant specific for a particular sequence pattern in the 'proximal-8' region.

Functional genomic FRT-like sequences may also include 1, 2, or all 3 of the following characteristics: (1) within the proximal 4-bp DNA segments of both binding elements of an FRT-like sequence ('proximal-8 region'; positions 24 through 21 and 1 through 4, which make eight base pairs in total, FIG. 1A), it is desirable that there be at least five matches with the corresponding base pairs of FRT; (2) it is desirable that there not be consecutive mismatches within the same 4-bp DNA segments; (3) it is desirable that at least one binding element have a match at position 7. In addition, functional FRT-like sequences generally do not have mismatches at positions 21 and 1 simultaneously or a 'G' at position 21 or a 'C' at position 1. Functional genomic FRT-like sequences also generally have at least 5 matches in one of the binding elements and at least 6 consecutive matches within both of the binding elements.

Cre: Like Flp, Cre is a tyrosine recombinase. Found in bacteriophage P1, Cre promotes recombination between two 34 bp sites known as loxP. As with FRT, loxP is composed of two inverted 13 bp arms, separated by an 8 bp spacer. The sequence recognized by the wild-type enzyme is (SEQ ID NO 13)
5'ATAACTTCGTATAatgtatgcTATACGAAGTTAT3'.

As with Flp, Cre variants are known and can be readily evolved to recognize loxP-like sequences, which differ from the wild-type recognition sequence at one or more locations from loxP. See e.g. Missirlis et al. (2006). A high-throughput screen identifying sequence and promiscuity characteristics of the loxP spacer region in Cre-mediated recombination. BMC Genomics 7:73. As with Flp, Cre variants suitable for the chimeric tyrosine recombinases of the invention will typically have at least 80, 85, 90, 95, or 98 percent amino acid homology to the wild type Cre enzyme. Suitable Cre variants may, for example, contain one or more mutations at the monomer-monomer interface, such as R24M (which corresponds to codon 32 in iCre).

Other Tyrosine Recombinases:

Any tyrosine recombinase, including the R (SEQ ID NO 9), B2 (SEQ ID NO 5), B3 (SEQ ID NO 5), KD (SEQ ID NO 7), KW (SEQ ID NO 8), SM (SEQ ID NO 8), and TD (SEQ ID NO 11) recombinases may be utilized in the chimeric tyrosine recombinases of the invention in essentially the same manner as described for Flp and Cre. Suitable variants of each may be evolved in a manner analogous to the process described in greater detail for Flp.

TAL: TAL's are transcription-like effectors, from *Xanthomonas* sp., that function to bind DNA sequences in the promotor region of sequences in the host plant genes, promoting expression of plant genes that assist in bacterial infection.

TAL effectors contain a central domain of repeats that functions to specify the target sequence for DNA binding. The core TAL DNA-binding domain (DBD) begins at position +152 (Δ152 truncation of the N-terminal segment of the TAL effector) and ends at the position +95 of the C-terminal segment of the TAL effector. Additional N-terminal and/or C-terminal amino acids may be present, if desired, and in some cases may provide a chimeric enzyme with greater activity than just the core DBD alone. See Miller et al., A TALE nuclease architecture for efficient genome editing. Nat Biotechnol 29(2):143-148 (2011). In certain instances, these additional sequences may function as a linker between the Flp variant module and the TAL DBD module in the chimeric Flp-TAL recombinase.

The TAL DNA-binding domain may be readily programmed to be specific for a target nucleic acid sequence of interest. The requirements for the TAL recognition sequence are quite relaxed. The only major prerequisite for a TAL recognition sequence is a thymine at position N−1 of the sequence. Beyond that, the TAL recognition sequence can be readily programmed.

The core TAL DBD comprises a series of tandem 33-35 amino acid repeats, the consensus sequence of which is (SEQ ID NO 14)
LTPDQVVAIASHDGGKQALETVQRLLPVLCQDHG.

The polymorphic pair of residues at amino acids 12-13 (underlined), known as the repeat variable di-residue (RVD), specifies the nucleotide to which the particular repeat targets according to the following rules: HD→C, NI→A, NG→T, NN→G. See Miller et al. (2011) and Cermak et al., (2011).

The desired number and particular repeats are assembled, according to the above rules, to achieve the desired level of specificity to the desired target sequence. The Golden Gate TALEN kit, for example, may be used to assemble the desired TAL DNA binding domain. See Cermak et al., Efficient design and assembly of custom TALEN and other TAL effector-based constructs for DNA targeting. Nucleic Acids Res 39(12):e82 (2011).

The TAL DBD module is generally programmed to recognize a DNA sequence of about 9-24 bp, 12-24 bp, or 15-24 bp in length, located to the left or the right of desired FRT-like sequence in the genome or nucleic acid of interest. In general, the TAL recognition sequence should be long enough to achieve the desired level of specificity (to be specific, very specific, highly specific, strictly specific, or completely specific) for the particular application. 9-24 bp is a length that is easily manageable from a technical point of view, though longer or shorter recognition sequences such as less than 8 or to 35 bp or more, may be appropriate in particular circumstances and the desired level of specificity. For instance, it may be advantageous for the length of the TAL binding sequences to correlate somewhat with the degree of similarity between the Flp binding elements of the FRT-like sequence and that of FRT: The weaker the similarity, the longer the TAL recognition sequence that may be optimal. Conversely, where there is a stronger the similarity between the Flp binding elements or the FRT-like sequence and FRT, a shorter the TAL recognition sequence may be desired. An example of a TAL DBD module, programmed to recognize an 18 nucleotide sequence is shown in FIG. 9 (SEQ ID NO 15).

Generally, the TAL binding sequence is chosen so as to be separated from the recombinase binding element of the FRT-like sequence by 3 to 12 base pairs, though again, longer and shorter lengths may be appropriate in particular situations. In general, a separation of 3-12 bp is sufficient to minimize steric clashes between the hybrid recombinase module, while still minimizing the spatial separation between the modules in a manner that allows the TAL DBD module to stabilize the Flp variant module and enhance the recombinase activity and/or the target specificity of the Flp variant module.

Chimeric tyrosine recombinase architecture: As exemplified by Flp, the mode of binding of the Flp recombinase to its native recognition sequence, Flp Recombination Target (FRT), specifies the mode of binding of the chimeric Flp-TAL recombinase to its target (FIG. 1A): the Flp variant module binds to the inner segments of the target sequence, which constitutes the actual FRT-like sequence, while the TAL module binds the outer segments of the target sequence.

Analysis of the Flp/DNA and the TAL DBD/DNA complexes shows that the TAL module can be fused to either the C-terminus or to the N-terminus of the module Flp, thus creating two chimeric recombinase architectures: Flp-TAL and TAL-Flp (FIG. 1). Both Flp-TAL and TAL-Flp are capable of binding to the head-to-tail and the tail-to-tail arrangements of the target sequences, provided the length of the linker that connects the modules is sufficiently long (FIG. 1). However, in the compact modes of the Flp-TAL and TAL-Flp architectures (that is, when the linker that connects the modules is short) Flp-TAL is able to bind to the 'convenient' head-to-tail arrangement of the target sequence while TAL-Flp can bind to the 'inconvenient' tail-to-tail arrangements of the target sequences (FIG. 1). The 'convenience' here is the property of the target sequence arrangement that describes (1) how easy it is to increase the length of the DNA sequence to which the TAL module binds without changing the length of the inter-modular linker and (2) how easy is to avoid steric clashes between the hybrid recombinase modules when the TAL module with longer C-terminal domains is used.

A module comprising a TAL DNA-binding domain is fused to the Flp variant module, either directly or through a linker. (FIG. 1C).

Linker: In certain embodiments of the invention, the chimeric Flp-TAL recombinase may optionally contain a linker between the Flp variant module and the TAL DBD module. When a linker is used, the linker may be positioned so as to connect the N terminus of the Flp variant module to the C terminus of the TAL DBD module. Alternatively, the linker may be positioned so as to connect the C terminus of the Flp variant module to the N terminus of the TAL DBD module. Generally, the latter configuration is easier to work with, as modifications to the N terminus of Flp are more likely to adversely affect recombinase activity. Any suitable linker may be used, as long as it does not reduce recombinase activity to such an extent that the chimeric enzyme is rendered non-functional in the desired system. In general, suitable linkers may be about 5 to about 20 amino acids in length, although linkers that are longer or shorter in length may also be used. A selection of suitable linkers are described, for example, in Akopian et al., Chimeric recombinases with designed DNA sequence recognition. Proc Natl Acad Sci USA 100(15):8688-8691 (2003).

NLS: In certain embodiments of the invention, the chimeric Flp-TAL recombinase may optionally include a heterologous nuclear localization signal (NLS). It is known that in certain instances, inclusion of a heterologous NLS may be advantageous and improve activity of the Flp variant. However, the native Flp enzyme, being of eukaryotic origen, naturally localizes to the nucleus. As such, a heterologous NLS is not required for proper functioning of the chimeric Flp-TAL recombinase.

An example of a chimeric Flp-TAL recombinase having a Flp variant domain, a linker, a TAL DBD and an NLS is shown in FIG. 10 (SEQ ID NO 37).

Codon optimization: In certain embodiments of the invention, it may be advantageous to perform codon optimization on all or part of the gene sequence encoding the chimeric Flp-TAL recombinase. Codon optimization is the process of modifying the coding region of a gene to more closely align the codon usage of a gene of interest with the codon usage frequency or codon bias of the target cell or organism, while retaining the same amino acid coding sequence. In some instances, codon optimization may improve translation efficiency. Numerous codon usage tables are publicly available and may be found, for example at www.genscript.com/tools/codon-frequency-tablem or www.kazusa.or.jp/codon/. See also Athey et al., A new and updated resource for codon usage tables, BMC Bioinformatics. 2017; 18: 391 (2017).

As noted above, genome engineering applications can utilize two versions of the Flp-TAL system that differ at the level of target specificity of the Flp variant modules: either strict or broad. In principle, the latter Flp variants (such as FV71 and/or other variants that can be evolved to have similar target selection functionality) can recognize a significant number if not the majority of the genomic FRT-like sequences. Therefore, the Flp-TAL system with such Flp variants can be quite convenient to use since only the TAL module needs to be engineered to target Flp-TAL recombinase to a new FRT-like sequence.

The efficiency of the integration and deletion reactions mediated by Flp-TAL: ~0.1% and ~10%, respectively, is comparable to that of wild-type Flp recombinase which lends confidence that the activity of Flp-TAL in dual recombinase-mediated cassette exchange (dual RMCE) will be also comparable to that of wild-type Flp.

Importantly, the deletion activity of Flp-TAL appears to be about two orders of magnitude higher than that shown for the hybrid serine recombinase recCas9 (Chaikind et al. (2016) A programmable Cas9-serine recombinase fusion protein that operates on DNA sequences in mammalian cells. Nucleic Acids Res 44(20):9758-9770). Moreover, no integration activity for recCas9 on the genomic targets was reported. Taken together, this demonstrates that the Flp-TAL system is a versatile genome engineering tool that can be significantly more active than other tailor-made target-specific recombination systems.

As the tyrosine recombinases have similar three-dimensional organization, similar mode of target binding, and are apparently well amenable to modification of their target specificity, other members of the tyrosine recombinase family can be also utilized to generate TAL-fused recombinases. These recombinases can greatly diversify the sequences that can be targeted by the TAL-fused recombination system, since each recombinase has its own set of target sequences in a genome. Moreover, different TAL-fused recombinases can be paired to perform dual RMCE to efficiently replace genome fragments. Importantly, the availability of several target-specific hybrid recombinases for dual RMCE would translate into shorter genome fragments that can be replaced: our analysis on the distribution of the target-like sequences for different recombinases in a genome shows that the arsenal of 5-6 hybrid recombinases is sufficient for reducing the size of the replaceable fragment to about 1 kb.

In the following examples, we demonstrate that chimeric target-specific Flp-TAL recombinases are a new versatile genome engineering tool that is able to recombine FRT-like sequences in their native genome environment. To our knowledge, this is the first demonstration of such activity for the target-specific variants of the tyrosine recombinases.

EXAMPLES

The invention may be better understood by reference to the following examples:

Using a simplified protein evolution approach, Flp variants for the chimeric Flp-TAL recombinase are evolved to recognize FRT-like sequences in the human β-globin gene. We examined the integration and deletion activity of the Flp-TAL recombinases in intact human HEK293 cells and demonstrated that only the chimeric Flp-TAL variants, but not the respective target-specific Flp variants, were able to efficiently perform these reactions. We also demonstrated that Flp variants with broad specificity toward FRT-like sequences can be fused to TAL DBDs of a desired target specificity, to direct the variant to new genomic target sequences. We estimate that the efficiency of the integration and deletion reactions mediated by the Flp-TAL variants is about 0.1% and 10%, respectively, which is comparable to that of wild-type Flp. Our results demonstrate that the present chimeric tyrosine recombinases are an attractive genome engineering platform.

Example 1: Selection of Genomic Target-Like Sequences

FRT-like sequences in the human genome are identified, essentially as described in Shultz et al. 2011.

Figure 2:
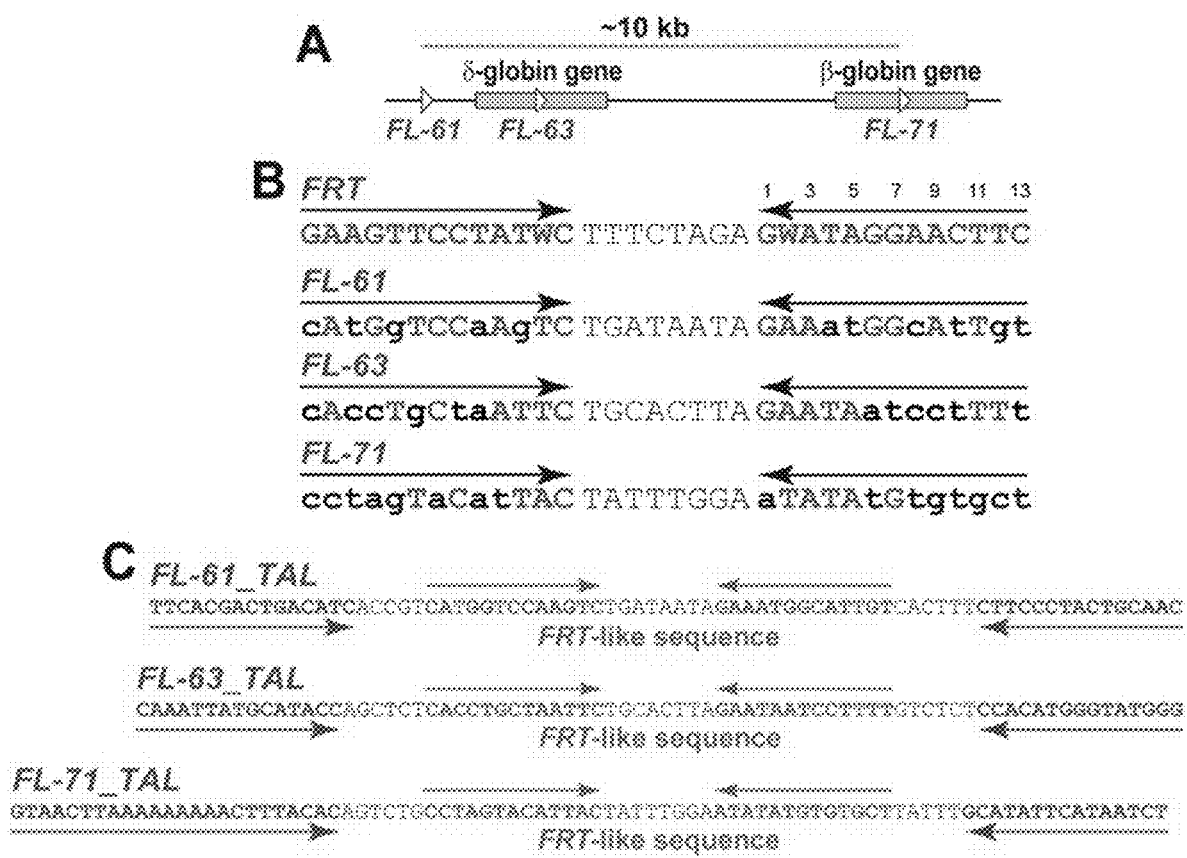
FIG. 2: FRT-like sequences FL-61, FL-63, and FL-71. Panel (A) shows the relative location of FL-61, FL-63, and FL-71 in the human genome. Panel (B) shows an alignment of FRT (SEQ ID NO 47), FL-61 (SEQ ID NO 16), FL-63 (SEQ ID NO 17), and FL-71 (SEQ ID NO 18). The base pairs in FL-61, FL-63, and FL-71 that differ from the corresponding base pairs in FRT are shown as lower case bold black letters. Panel (C) shows FL-61_TAL (SEQ ID NO 19), FL-63_TAL (SEQ ID NO 20), and FL-71_TAL (SEQ ID NO 21) sequences. 5'T bases for the TAL recognition sequences (marked by blue arrows) are shown in red.

Three FRT-like sequences located upstream of the human S-globin gene and within the S-globin and β-globin genes are selected, denoted FL-61 (SEQ ID NO 16), FL-63 (SEQ ID NO 17), and FL-71 (SEQ ID NO 18), respectively, which are separated from each other by 2.7 kb and ~7.5 kb, respectively (FIGS. 2A and B). These FRT-like sequences, as well as other genomic FRT-like sequences, can have several potential upstream and downstream TAL recognition sequences since the requirements for the TAL recognition sequences are quite relaxed—the only major prerequisite being a thymine at the position N−1 of the sequence: 5'T (Lamb B M, Mercer A C, & Barbas C F, 3rd (2013) Directed evolution of the TALE N-terminal domain for recognition of all 5' bases. Nucleic Acids Res 41(21):9779-9785).

We reasoned that to be useful in targeting Flp-TAL recombinases to the desired FRT-like sequences and yet to be easily manageable from the technical point of view, the TAL module should recognize a DNA sequence of about 9-24 bp, 12-24 bp, or 15-24 bp in length. We also reasoned that the TAL binding sequence should be separated from the recombinase binding element of the FRT-like sequence by 3 to 12 base pairs to avoid steric clashes between the hybrid recombinase modules or their significant spatial separation.

Additionally, we reasoned that the length of the TAL binding sequences should correlate with the degree of similarity between the Flp binding elements of the FRT-like sequence and that of FRT: the weaker the similarity, the longer the TAL recognition sequence.

Based on the above considerations, we decided to examine TAL binding sequences of 15 bp in length (except for the upstream 24-bp TAL binding site for FL-71) that are separated from FL-61 (SEQ ID NO 19), FL-63 (SEQ ID NO 20), and FL-71 (SEQ ID NO 21) by 4-5 bp (FIG. 2C)

Example 2: Evolution of Flp Variants with Strict and Relaxed Target Specificity

Previously we had evolved a number of Flp variants that recognize different genomic targets (Bolusani S, et al. (2006); Shultz J L, et al., (2011); (Shah et al. (2015)). In addition to unique mutations, these enzymes contain a group of mutations that is usually present in all variants. Without intending to be bound by a particular theory, we believe that these common mutations collectively relax the strict target specificity of Flp and allow it to recombine not only FRT but also FRT-like sequences. The unique mutations in these Flp variants either further relax or, in contrast, narrow the variant's target specificity.

The Flp variants that bear the common as well the unique mutations can be used to speed up the evolution of the Flp variants with target-specific or target-relaxed phenotypes if their genes are used as templates for generating shuffled variant libraries which can be screened to identify the desired target specificity. The pool of the template variant genes can be enhanced by including the library of the Flp genes that are randomized at codons 55, 58 and 59, since the amino acids at these positions contact the first four base pairs of the Flp binding elements of FRT that were shown to be the most critical for the Flp-FRT recognition (Shultz J L, et al., (2011)). Flp variants suitable for generating hybrid Flp-TAL recombinases, that is, those with relatively low activity and with strict or somewhat relaxed target specificity are evolved by one-two rounds of protein evolution using a pair of different but related recombination sequences: a genomic FRT-like sequence and FRT. Thus, Flp variants for the FL-61 FRT-like sequence are evolved using the recombining pair FL-61/FRT (SEQ ID NO 16/SEQ ID NO 12); Flp variants for the FL-63 FRT-like sequence are evolved using the recombining pair FL-63/FRT (SEQ ID NO 17/SEQ ID NO 12); and Flp variants for the FL-71 FRT-like sequence are evolved using the recombining pair FL-71/FRT (SEQ ID NO 18/SEQ ID NO 12). We then compared the activity of the evolved Flp variants on the FL-61 (SEQ ID NO 16), FL-63 (SEQ ID NO 17), and FL-71 (SEQ ID NO 18) sequences.

To identify Flp variants with the desired properties a screening system that is composed of the inversion and deletion reporters that are used sequentially was utilized (FIGS. 3A and B). The reporter cassettes in these vectors are flanked by the pair of the recombination sites that are arranged in the head-to-head and head-to-tail orientations, respectively. The inversion and deletion reporters have different purpose. The inversion reporter is used to identify a large pool of Flp variants that are able to recombine both the FRT-like sequence and FRT (SEQ ID NO 12); these variants are selected by amplifying the Flp variant genes in the inversion-positive configuration of the reporter (FIG. 3A). The deletion reporter is used to screen the inversion-positive library of the Flp variants that are sufficiently active to delete the reporter cassette in at least some vector molecules (FIG. 3B).

Inversion Experiments

A Flp variant library is constructed using Flp variants that bear both common and unique mutations, as well as Flp genes that are randomized at codons 55, 58, and 59, as templates for generating a shuffled Flp variant library. The shuffled Flp variant library is then ligated into an inversion reporter (a derivative of pBAD33) and transformed into bacterial cells and incubated with the inducer L-arabinose at the final concentration 0.1% for 2.5 hours. The transformed cells (0.3 ml) are then transferred into 20 ml of LB medium supplemented with chloramphenicol (35 µg/ml) and incubated overnight. The reporter plasmids are then isolated and subjected to the PCR analysis to identify those Flp variants that are able to invert the reporter.

The reporter contains the inversion cassette flanked by the recombination targets in the head-to-head orientation: FL-61, FL-63, or FL-71 (marked as RT) and FRT* that bears the spacer either from FL-61, FL-63, or FL-71, respectively. Upon expression of a recombination competent Flp variant, the cassette is inverted so the gene that encodes this variant can be amplified. (FIG. 3A).

Deletion Experiments

The deletion experiments are performed essentially as described in Voziyanov et al., 2002. In brief, the Flp variant library (from the example above) is transformed into bacterial cells that harbor the deletion reporter (a derivative of pBAD24 (Guzman et al. (1995) Tight regulation, modulation, and high-level expression by vectors containing the arabinose PBAD promoter. J Bacteriol 177(14):4121-4130)). After incubating the transformed cells with the inducer L-arabinose at the final concentration 0.1% for 2.5 hours, the cells are plated onto LB/agar plates that contained X-gal to visualize the colonies in which the deletion of the lacZα cassette has occurred. (FIG. 3B).

The deletion reporter has the lacZα cassette flanked by the recombination targets in the head-to-tail orientation. If a Flp variant is able to delete the cassette, the resulting bacterial cells will form white colonies when plated on the X-gal containing plates. (FIG. 3D).

The screen of the library of the shuffled Flp variant genes that bear the desired set of mutations using the respective inversion and deletion reporters identified several Flp variants that were able to recombine the FL-61/FRT (SEQ ID NO 16/SEQ ID NO 12), FL-63/FRT (SEQ ID NO 17/SEQ ID NO 12), and FL-71/FRT (SEQ ID NO 18/SEQ ID NO 12) pairs with reasonable efficiency. The variants that demonstrated the highest activity on their respective recombination pairs were named FV61, FV63, and FV71 and tested for their ability to recombine all three FRT-like sequences to identify the variants with either strict or broad target specificity (FIGS. 3D and E).

FV61, FV63, and FV71 responded differently when they were challenged with the 'non-cognate' FRT-like sequences (FIGS. 3D and E). FV63 was the most specific and was able to recombine with the reasonable efficiency only the FL-63 sequence; some minor recombination activity was seen on FL-61 but the recombination activity on FL-71 was barely detectable. FV71 was the least specific and was able to recombine all three FRT-like sequences. FV61 was also able to recombine FL-61, FL-63, and FL-71 but we noticed abnormalities in its phenotype: the pale blue colonies in the experiments with all FRT-likes sequences (FIG. 3D) and the faint reporter bands in the FL-71 experiments (both unrecombined and recombined, FIG. 3E); these abnormalities apparently indicate that FV61 binds to DNA (or just to the FRT-like sequences) tighter than do FV63 and FV71. Off note, our evolution experiments sometimes generate Flp variants with the FV61-like phenotype.

The mutational profile of FV61, FL63, and FV71 is shown in FIG. 3C. As anticipated, these Flp variants bear a group of common mutations at positions 35, 45, 50, 114, 295, and 363. In addition, each variant has a set of unique mutations, some of which were seen before in other target-specific Flp variants (positions 44, 62, 130, 173, 176, 193, and 324) while the other unique mutations are new (positions 3, 18, 75, 85, 157, 171, 213, and 290). In addition, FV61 and FV63 have the same set of mutations at positions 55, 58, and 59 which is different from that of FV71. We also noted that the profile of mutations in FV61, FL63, and FV71 is different from that of the Flp variants that were evolved to recombine FL-61, FL-63, and FL-71 (individually, rather than against the combinations FRT/FL-61, FRT/FL063, or FRT/FL-71) (Shultz et al. (2011)).

Note: All bacterial experiments were performed using *E. coli* strain NEB 10-beta from New England Biolabs: araD139 Δ(ara-leu)7697 fhuA lacX74 galK (φ80 Δ(lacZ) M15) mcrA galU recAl endAl nupG rpsL (StrR) Δ(mrr-hsdRMS-mcrBC).

Example 3: Flp-TAL Variants can Integrate a Reporter into the Desired Locations in the Human Genome As noted, FL-61 (SEQ ID NO 16), FL-63 (SEQ ID NO 17), and FL-71 (SEQ ID NO 18) each have several potential TAL DBD upstream and downstream of these sites. Since it was reasoned that the TAL DBD should be separated from each FRT-like sequence by about 3-12 to avoid steric clashes between the hybrid recombinase module while still minimizing the separation so as to bet the most substantial benefit of the TAL DBD stabilizing the recombinase module on the FRT-like site, TAL DBD's are programmed to be specific for sequences separated from FL-61, FL-63, and FL-71 by 4-5 bp (FIG. 2C) (SEQ ID NO 19, SEQ ID NO 20, SEQ ID NO 21). Sequences of 15 bp in length upstream and downstream of each of the sites are selected, with the exception of the sequence upstream from FL-71. A longer sequence of 24 bp is chosen for the latter TAL DBD. Sequences of 15 and 18 bp were also tested for the upstream sequences of FL-71. (SEQ ID NO 44 and SEQ ID NO 45). These sequences performed as well as the longer 24 bp sequence.

To demonstrate that Flp-TAL recombinases are capable of targeting FRT-like sequences in their native environment, we fused the FV61, FV63, and FV71 variants with their respective TAL modules (FIGS. 1A and 2C). Since the TAL modules in the Flp-TAL recombinase have to be specific for both upstream and downstream TAL recognition sequences of the FRT-like sequence, two Flp-TAL variants for each fusion recombinase were engineered: Flp-TAL(L) and Flp-TAL(R), FIG. 1A. For the sake of simplicity, the left and the right Flp-TAL variants of FV61, FV63, and FV71 are collectively called FV61-TAL, FV63-TAL, and FV71-TAL, respectively.

TAL DBD's are programmed using the Golden Gate TALEN kit, following the procedure of Cermak et al. (2011). Following the known rules, where the repeat variable di-residues (RVD) HD, NI, NG, and NN encode for binding to C, A, T, and G, respectively, 15 tandem repeats are assembled for the sequences upstream and downstream (left and right) of FL-61 (SEQ ID NO 22) (SEQ ID NO 23) and FL-63 (SEQ ID NO 24) (SEQ ID NO 25) and downstream of FL-71 (SEQ ID NO 27), as denoted in FIG. 2C. 24 tandem repeats are assembled to be specific for the 24 bp upstream of FL-71 (SEQ ID NO 26). These TAL DBD's are referred to as FL-61_TAL(L) (SEQ ID NO 28), FL-61_TAL(R) (SEQ ID NO 29), FL-63_TAL(L) (SEQ ID NO 30), FL-63_TAL(R) (SEQ ID NO 31), FL-71_TAL(L) (SEQ ID NO 32), FL-71_TAL(R) (SEQ ID NO 33), respectively.

Mammalian cell experiments were performed in human embryonic kidney HEK-293 cells (ATCC, CRL-1573) which were propagated in EMEM medium. Cell transfections were performed using DNA-In (Molecular Transfer) or Turbo293 reagents (Speed BioSystems).

Flp and Flp-TAL variants were expressed from the pOG100 vector (a derivative of pOG44 (Anderson et al. (2012) Flp and Cre expressed from Flp-2A-Cre and Flp-IRES-Cre transcription units mediate the highest level of dual recombinase-mediated cassette exchange. Nucleic Acids Res 40(8):e62.). The pTarget reporter is a derivative of the pDNA3 vector (Invitrogen).

The experiments to integrate pTarget into FL-61 (SEQ ID NO 16), FL-63 (SEQ ID NO 17), and FL-71 (SEQ ID NO 18) were performed as follows. HEK-293 cells were co-transfected, in 24-well plates, with pTarget (0.4 µg) and the respective pOG100-FV-TAL vector (1 µg). 48 hours post-transfection, 1/10 of the cells were transferred into 6-well plate containing EMEM medium supplemented with hygromycin (550 mg/l). About 10 days later, all hygromycin resistant colonies were pooled and analyzed by PCR and sequencing. Alternatively, individual red (FV61-TAL and FV63-TAL experiments) or green (FV71-TAL experiments) colonies were transferred into 48-well plate, expanded and analyzed.

The deletion experiments were performed by transfecting the respective cells in 24-well plates with pOG100-FV71-TAL (1 µg). 48 hours post transfection, all cells were transferred into 6-well plates, allowed to become confluent, collected, and analyzed by PCR and sequencing.

Figure 4:
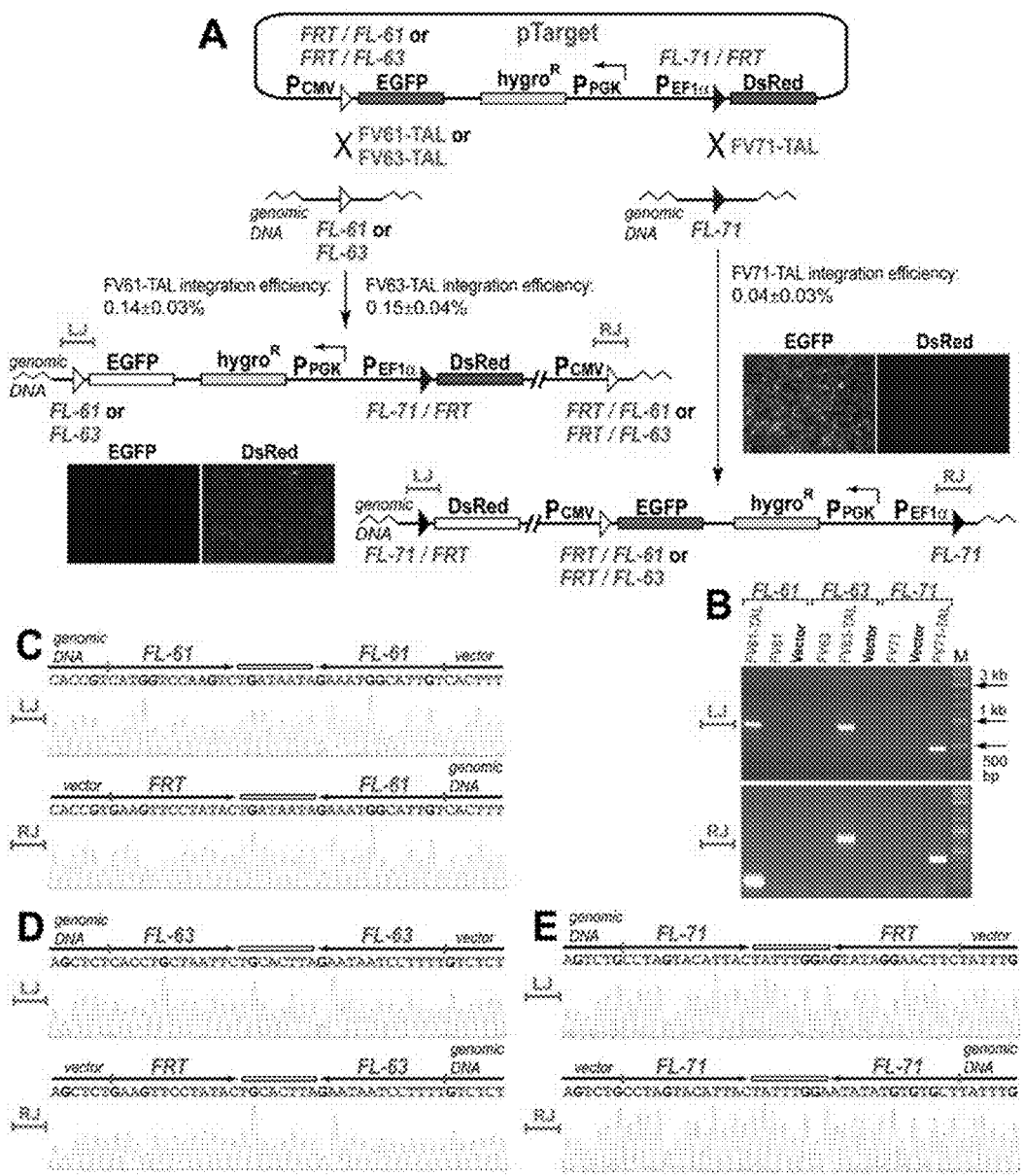
FIG. 4: Flp-TAL variants can target FL-61, FL-63, and FL-71 in unmodified HEK-293 cells. (A) Schematics of the integration assays. The reporter can be integrated either into FL-61, FL-63, or FL-71 depending on the specificity of the Flp-TAL recombinase. Upon integration of pTarget into FL-61 or FL-63 the resultant cells become hygromycin resistant and red, while if integrated into FL-71, the cells become hygromycin resistant and green (images of the individual expanded hygro$^R$/red and hygro$^R$/green colonies are shown as examples). The analysis of the individual colonies was performed in two biological replicates. LJ and RJ show the locations of the diagnostic PCR products at the left and right junctions of the integrated reporter and genomic DNA. (B) PCR analysis of the pooled hygro$^R$ colonies generated in the experiments with the Flp-TAL recombinase, the 'plain' recombinase variant, or the empty expression vector. LJ, RJ, the PCR analysis of the left and right junctions of pTarget integrated into the respective genomic sequences; M, DNA ladder. (C), (D), and (E) Sequencing of the integration-specific PCR products LJ and RJ of pTarget integrated into FL-61 (SEQ ID NO 48) (SEQ ID NO 49), FL-63 (SEQ ID NO 50) (SEQ ID NO 51), and FL-71 (SEQ ID NO 52) (SEQ ID NO 53), respectively, confirmed their identity.
Figure 5:
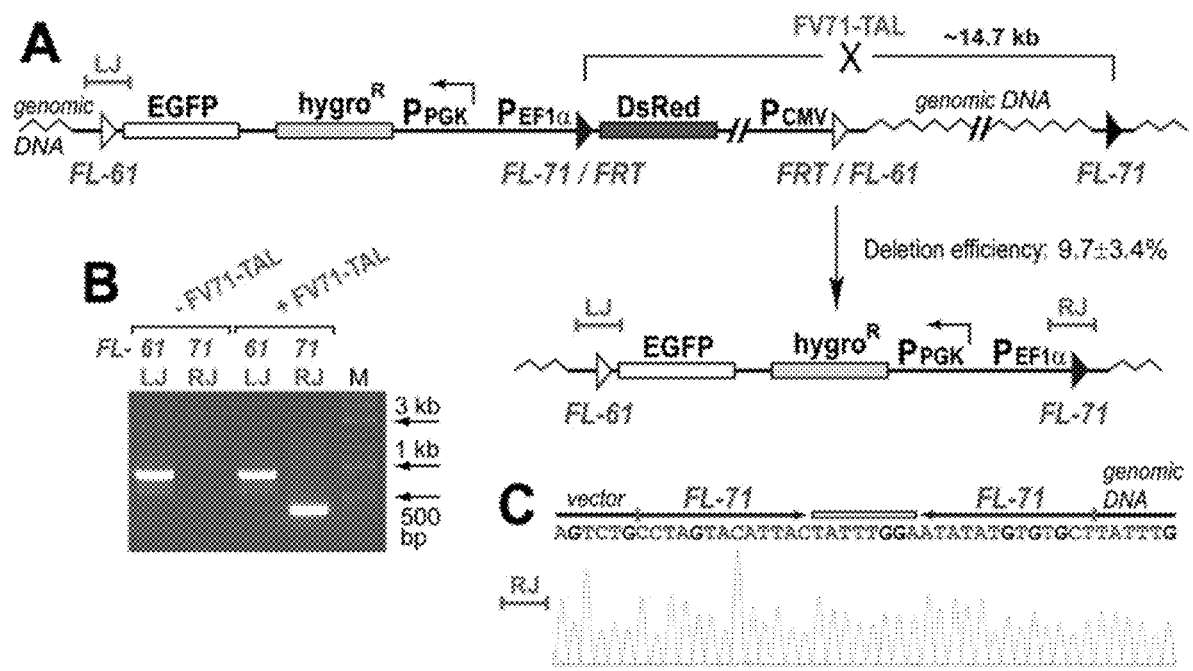
FIG. 5: Flp-TAL recombinase can delete a genome fragment. (A) Schematic of the deletion assay. Upon expression of FV71-TAL, the DNA fragment that is located between two FL-71 sequences and that contains part of the reporter and genomic DNA gets deleted. (B) PCR analysis of the FV71-TAL treated cells which bear pTarget integrated into FL-61. The deletion activity was analyzed in three biological replicates. FL-61/LJ and FL-71/RJ, the PCR analysis of the respective junctions of the integrated pTarget before and after the treatment with FV71-TAL. M, DNA ladder. (C) Sequencing of the deletion-specific PCR product FL-71/RJ confirmed its identity (SEQ ID NO 53).

The targeting activity of the hybrid Flp-TAL recombinases were analyzed via integration and deletion assays (FIGS. 4 and 5). The schematic of the integration assay is shown in FIG. 4A. The reporter vector pTarget bears three transcriptional units that express EGFP, hygromycin B phosphotransferase (hygroR), and DsRed. In this reporter, the hybrid FRT/FL-61 (SEQ ID NO 34) (or FRT/FL-63 (SEQ ID NO 35)) site is located between the CMV promoter and the EGFP gene while the hybrid FRT/FL-71 site is positioned between the EF1α promoter and the DsRed gene (SEQ ID NO 36). (FIG. 8).

If FV61-TAL (or FV63-TAL) integrates pTarget into the native FL-61 (SEQ ID NO 16) (or FL-63 (SEQ ID NO 17)) sequence, the EGFP gene loses its promoter and thus cannot be expressed. The resultant cells should be therefore red and not green (FIG. 4A). Alternatively, if FV71-TAL is capable of integrating pTarget into the native FL-71 sequence (SEQ ID NO 18), the DsRed gene loses its promoter and cannot be expressed. The resultant cells should be therefore just green (FIG. 4A).

To demonstrate the integration activity of the Flp-TAL recombinases, we co-transfected HEK293 cells with the pTarget reporter and the vectors that express FV61-TAL, FV63-TAL, or FV71-TAL. 48 hours post-transfection, 1/10 of the cells were transferred into medium supplemented with hygromycin and incubated for about 10 days until the hygroR colonies are formed. Four types of colonies were observed: with no color, green and red, just green, and just red. We did not note apparent differences in the ratios of these colony types in the experiments with FV61-TAL, FV63-TAL, and FV71-TAL.

To demonstrate that the Flp-TAL recombinases are capable of integrating the reporter into the desired FRT-like sequences, the hygromycin resistant colonies were pooled and their genomic DNA isolated and subjected to the PCR analysis, which confirmed the correct integration events (FIG. 4B).

Importantly, the control experiments with the 'plain' (i.e., lacking a TAL DBD) Flp variants FV61, FV63, and FV71 did not yield detectable integration of the reporter into the respective genomic FRT-like sequences.

To determine the efficiency of integration, we performed a series of integration experiments as described above but instead of pooling all hygromycin resistance colonies we expanded only either just red colonies (FV61-TAL and FV63-TAL experiments) or just green colonies (FV71-TAL experiments) and subjected them to the PCR analysis. These experiments revealed that the hybrid recombinases integrated the reporter vector, on average, in about 0.1% of the transfected cells (although the efficiency of integration into FL-61 (SEQ ID NO 16) and FL-63 (SEQ ID NO 17) was about three times higher than into FL-71) (SEQ ID NO 18).

Example 4: FV71 can Recombine Different FRT-Like Sequences in the Human Genome when Fused to the TAL Modules with the Respective Target Specificity We next examine whether FV71, which was able to recombine different FRT-like sequences in bacteria (FIGS. 3E and D), could also recombine these sequences in their native genome environment. For this, we fused FV71 with the respective TAL modules that are specific for either FL-61 or FL-63 (FIG. 2C) to obtain the FV71-TAL61 and FV71-TAL63 variants, respectively. We then performed the integration experiments as described in the previous section and found that FV71-TAL61 and FV71-TAL63 were able to target FL-61 and FL-63 as efficiently as did FV61-TAL and FV63-TAL (FIG. 4).

In parallel, we also tested whether FV61, which showed an apparent tight binding phenotype in bacterial cells (FIGS. 3E and D), was able to target FL-71 if fused to the respective TAL module. Despite extensive experimenting we were unable to detect FV61-TAL71-mediated integration of the reporter vector into FL-71.

Example 5: Flp-TAL Recombinases can Delete Genome Fragments

Finally, we examined the ability of the Flp-TAL recombinases to delete large genome fragments. In these experiments we utilized the property of the targeting vector to bear two different FRT-like sequences (FIG. 4A). Upon integration of the vector into one of the respective genomic FRT-like sequences, the other vector-borne FRT-like sequence can be used to delete the DNA fragment that is located between this sequence and the corresponding genomic FRT-like sequence (FIG. 5A).

In the deletion assays we used the expanded integration-positive red cells that were obtained in the FV61-TAL integration experiments (FIG. 5). These cells were transfected with the vector that expresses the FV71-TAL recombinase and then expanded and subjected to the PCR analysis to assess the ratio of the cells, in which the 14.7 kb DNA fragment was deleted. The analysis of the sequentially diluted genomic DNA (Chaikind et al. A programmable Cas9-serine recombinase fusion protein that operates on DNA sequences in mammalian cells. Nucleic Acids Res 44, 9758-9770, doi:10.1093/nar/gkw707 (2016)) revealed that the deletion occurred, on average, in about 10% of the transfected cells.

Example 6: Evolution of iCre Variant Having Relaxed Target Specificity

Essentially as described in Example 2 above, iCre variants with relaxed target specificity are evolved using loxP (SEQ ID NO 13) and the lox-like target sequence 69058 (LL-69) (SEQ ID NO 46). One particular clone is selected for further characterization and experimentation. The variant contains an amino acid R to M substitution at position 32 of iCre (SEQ ID NO 4), which corresponds to an R to M substation at position 24 of wild-type Cre. The iCre variant is referred to herein as iCreM24 (SEQ ID NO 38) (SEQ ID NO 39).

Chimeric tyrosine recombinases using iCreM24 as the recombinase module are then constructed, as described above, using different TAL DBD modules designed to target potential TAL binding sites near LL-69 (SEQ ID NO 41) (SEQ ID NO 42) (SEQ ID NO 43). (FIG. 12) Each were successfully tested in CHO cells, essentially as described above. TAL/L15-TAL/R12_1 (SEQ ID NO 41) was recombined by the mixture of two variants: iCreM24-TAL(L15-1) and iCreM24-TAL(R12); TAL/L15-TAL/R15_2 (SEQ ID NO 42) was recombined by the mixture of two variants: iCreM24-TAL(L15-2) and iCreM24-TAL(R15); and TAL/L15-TAL/R12_2 (SEQ ID NO 43) was recombined by the mixture of two variants: iCreM24-TAL(L15-2) and iCreM24-TAL(R12). The chimeric Cre-TAL recombinase pairs directed to LL-69 are referred to collectively as Cre69-TAL.

A partial sequence of a CreM24-TAL chimeric recombinase is shown in FIG. 13. (SEQ ID NO 40). Note that in this instance, the TAL DBD module begins at position delta-117. The additional TAL sequence is believed to function as a longer linker. In general, chimeric Cre-TAL recombinases appear to function better with longer linker sequences than Flp-TAL recombinases. Without intending to be bound by any particular theory, it is believed that this is related to the differences in the 3D structures of Flp and Cre. In Flp, the C-terminus is closer to the 5'-end of the recombinase binding sequence than that of Cre.

Example 7: Dual RMCE Mediated by Cre-TAL and Flp-TAL

Figure 14:
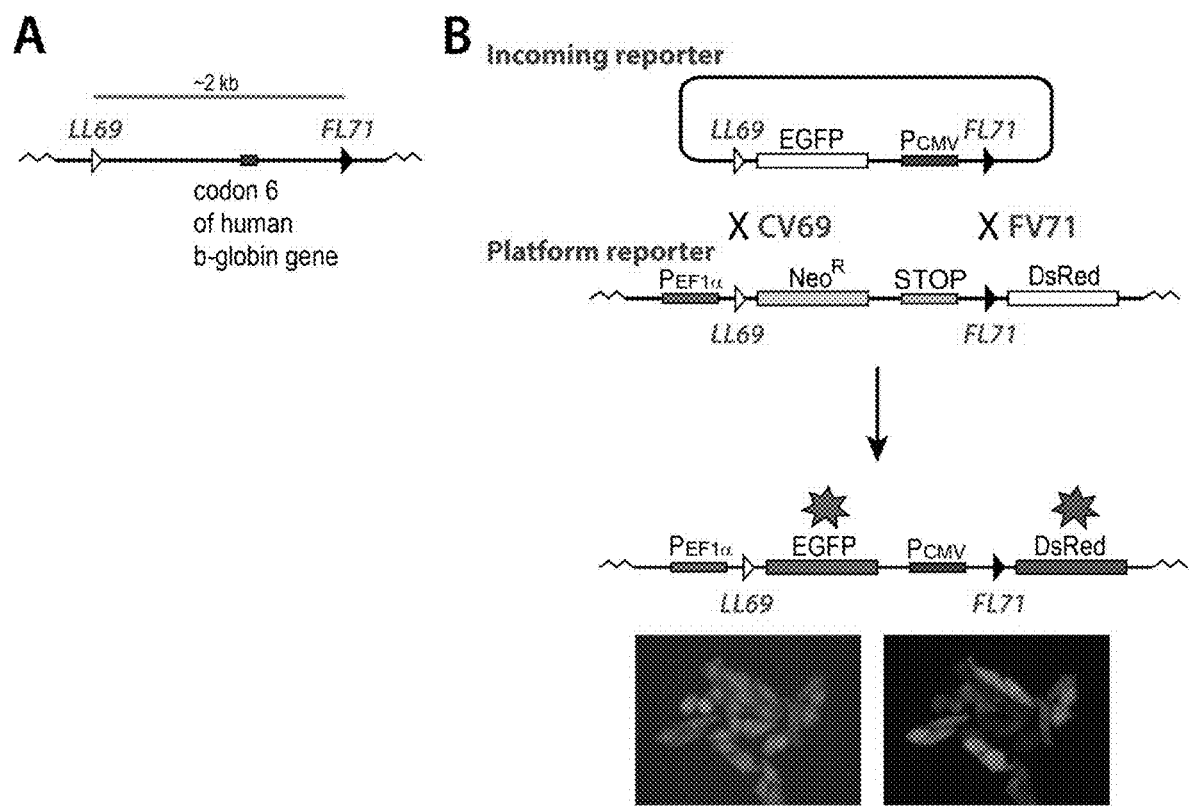
FIG. 14: Dual RMCE mediated by Cre-TAL and Flp-TAL variants CV69 and FV71. (A) Relative location of the loxP-like sequence LL69 and FRT-like sequence FL71 in the human genome. These sequences are recognized by CV69 and FV71, respectively. (B) Schematic of the dual RMCE reaction to test the replacement activity of the Cre and Flp variants. The cells, in which the replacement occurred, express both EGFP and DsRed.

To monitor the activity of Flp71-TAL and Cre69-TAL during dual RMCE, we have constructed a set of two reporter plasmids that, via activating the expression of two different fluorescent markers, can assess the efficiency of a replacement reaction catalyzed by the hybrid recombinases in the absence of a selection force (FIG. 14B). One of the two reporter plasmids serves as a platform that is integrated into an actively transcribed locus of the CHO genome, and the other is an incoming reporter.

The reporter cassette in the platform plasmid p1372/69-71 contains the NeoR gene under the control of the EF1α promoter. The NeoR gene is followed by the transcription terminator STOP (Sauer, B. (1993) Manipulation of transgenes by site-specific recombination: use of Cre recombinase. Methods Enzymol, 225, 890-900)) and the promoterless DsRed gene. The Cre69-TAL cognate sequence LL-69 (SEQ ID NO 46) is located between the EF1α promoter and the NeoR gene; the Flp71-TAL cognate sequence FL-71 (SEQ ID NO 18) is located between STOP and the DsRed gene. The platform reporter p1372/69-71, which is a derivative of the pcTD plasmid of the TD-In system (Anderson et al. (2012) Flp and Cre expressed from Flp-2A-Cre and Flp-IRES-Cre transcription units mediate the highest level of dual recombinase-mediated cassette exchange. Nucleic Acids Res, 40, e62.), was integrated into the TDRT site located in the genome of the CHO TD-In cells using the TD-40 variant of TD recombinase to obtain the CHO-1372/69-71 cell line. The incoming plasmid p1345/69-71 carries a reporter cassette composed of the promoterless EGFP gene followed by the CMV promoter. LL-69 and FL-71 that can recombine with their counterparts in the plasmid p1372/69-71, flank the EGFP-CMV reporter cassette (FIG. 14A).

Cre69-TAL-catalyzed recombination between the LL-69 sites located on the platform and the incoming reporters leads to the swap between the NeoR and the EGFP genes and therefore activates the expression of the EGFP gene (FIG. 14B). Flp71-TAL-catalyzed recombination between the FL-71 sites leads to the swap between the transcription terminator STOP and the CMV promoter thus activating the expression of the DsRed gene (FIG. 14B).

A dual RMCE reaction between the reporter cassettes located in the incoming and the platform plasmids is catalyzed by a simultaneous supply of both Cre69-TAL and Flp71-TAL recombinases (FIG. 14B). Successful dual RMCE is expected to replace the NeoR-STOP cassette in the integrated platform reporter with the EGFP-CMV cassette in the incoming plasmid. As a result, the expression of both EGFP and DsRed genes is activated which can be detected by the appearance of cells that are both green and red (FIG. 14B).

Construction of CHO-1372/69-71 cell line

To construct CHO-1372/69-71 cell line, CHO TD-In cells were co-transfected with the platform reporter p1372/69-71 and pOG-TD1-40 (Anderson et al. (2012)), which expresses the TD1-40 variant of the TD recombinase (Blaisonneau, et al. (1997) A circular plasmid from the yeast *Torulaspora delbrueckii*. Plasmid, 38, 202-209.). 48 hours post-transfection, ⅙ of the cells were transferred into a 100 mm plate into the medium supplemented with hygromycin. After about 10 days, several hygromycin resistant colonies were transferred into 96-well plate and their sensitivity to zeocin and neomycin was tested. The colonies that were sensitive to zeocin and resistant to neomycin were used in the RMCE experiments.

Recombinase-Mediated Cassette Exchange Experiments

Dual RMCE experiments were performed by transfecting the platform CHO-1372/69-71 cells with the incoming reporter p1372/69-71 and both expression vectors: Cre69-TAL and Flp71-TAL. 48 hours post transfection, ⅙ of the cells were transferred into 6-well plates, the cells were allowed to become confluent, and the number of the green, red, and green-red colonies was counted. Several colonies that were both green and red were expanded and analyzed. The efficiency of the replacement reaction was about 0.01-0.03%.

REFERENCES

1. Miller J C, et al. (2011) A TALE nuclease architecture for efficient genome editing. Nat Biotechnol 29(2):143-148.
2. Cong L, et al. (2013) Multiplex genome engineering using CRISPR/Cas systems. Science 339(6121):819-823.
3. Komor A C, Kim Y B, Packer M S, Zuris J A, & Liu D R (2016) Programmable editing of a target base in genomic DNA without double-stranded DNA cleavage. Nature 533(7603):420-424.
4. Kim Y B, et al. (2017) Increasing the genome-targeting scope and precision of base editing with engineered Cas9-cytidine deaminase fusions. Nat Biotechnol 35(4): 371-376.
5. Grindley N D, Whiteson K L, & Rice P A (2006) Mechanisms of site-specific recombination. Annual review of biochemistry 75:567-605.
6. Buchholz F & Stewart A F (2001) Alteration of Cre recombinase site specificity by substrate-linked protein evolution. Nat Biotechnol 19(11):1047-1052.
7. Sarkar I, Hauber I, Hauber J, & Buchholz F (2007) HIV-1 proviral DNA excision using an evolved recombinase. Science 316(5833):1912-1915.
8. Bolusani S, et al. (2006) Evolution of variants of yeast site-specific recombinase Flp that utilize native genomic sequences as recombination target sites. Nucleic Acids Res 34(18):5259-5269.
9. Shultz J L, Voziyanova E, Konieczka J H, & Voziyanov Y (2011) A genome-wide analysis of FRT-like sequences in the human genome. PLoS One 6(3):e18077.
10. Guo F, Gopaul D N, & van Duyne G D (1997) Structure of Cre recombinase complexed with DNA in a site-specific recombination synapse. Nature 389(6646):40-46.
11. Chen Y, Narendra U, Iype L E, Cox M M, & Rice P A (2000) Crystal structure of a Flp recombinase-Holliday junction complex: assembly of an active oligomer by helix swapping. Mol Cell 6(4):885-897.
12. Karpinski J, et al. (2016) Directed evolution of a recombinase that excises the provirus of most HIV-1 primary isolates with high specificity. Nat Biotechnol 34(4):401-409.
13. Shah R, Li F, Voziyanova E, & Voziyanov Y (2015) Target-specific variants of Flp recombinase mediate genome engineering reactions in mammalian cells. The FEBS journal 282(17):3323-3333.
14. Akopian A, He J, Boocock MR, & Stark WM (2003) Chimeric recombinases with designed DNA sequence recognition. Proc Natl Acad Sci USA 100(15):8688-8691.

15. Gordley R M, Smith J D, Graslund T, & Barbas C F, 3rd (2007) Evolution of programmable zinc finger-recombinases with activity in human cells. J Mol Biol 367(3): 802-813.
16. Mercer A C, Gaj T, Fuller RP, & Barbas CF, 3rd (2012) Chimeric TALE recombinases with programmable DNA sequence specificity. Nucleic Acids Res 40(21):11163-11172.
17. Chaikind B, Bessen J L, Thompson DB, Hu J H, & Liu D R (2016) A programmable Cas9-serine recombinase fusion protein that operates on DNA sequences in mammalian cells. Nucleic Acids Res 44(20):9758-9770.
18. Kim Y G, Cha J, & Chandrasegaran S (1996) Hybrid restriction enzymes: zinc finger fusions to Fok I cleavage domain. Proc Natl Acad Sci USA 93(3):1156-1160.
19. Christian M, et al. (2010) Targeting DNA double-strand breaks with TAL effector nucleases. Genetics 186(2):757-761.
20. Porteus MH & Carroll D (2005) Gene targeting using zinc finger nucleases. Nat Biotechnol 23(8):967-973.
21. Urnov F D, et al. (2005) Highly efficient endogenous human gene correction using designed zinc-finger nucleases. Nature 435(7042):646-651.
22. Miller J C, et al. (2007) An improved zinc-finger nuclease architecture for highly specific genome editing. Nat Biotechnol 25(7):778-785.
23. Cermak T, et al. (2011) Efficient design and assembly of custom TALEN and other TAL effector-based constructs for DNA targeting. Nucleic Acids Res 39(12):e82.
24. Gaj T, Gersbach C A, & Barbas CF, 3rd (2013) ZFN, TALEN, and CRISPR/Cas-based methods for genome engineering. Trends Biotechnol 31(7):397-405.
25. Mak AN, Bradley P, Cernadas RA, Bogdanove AJ, & Stoddard BL (2012) The crystal structure of TAL effector PthXol bound to its DNA target. Science 335(6069):716-719.
26. Lamb BM, Mercer A C, & Barbas CF, 3rd (2013) Directed evolution of the TALE N-terminal domain for recognition of all 5' bases. Nucleic Acids Res 41(21): 9779-9785.
27. Guzman L M, Belin D, Carson MJ, & Beckwith J (1995) Tight regulation, modulation, and high-level expression by vectors containing the arabinose PBAD promoter. J Bacteriol 177(14):4121-4130.
28. Voziyanov Y, Stewart A F, & Jayaram M (2002) A dual reporter screening system identifies the amino acid at position 82 in Flp site-specific recombinase as a determinant for target specificity. Nucleic Acids Res 30(7):1656-1663.
29. Anderson RP, Voziyanova E, & Voziyanov Y (2012) Flp and Cre expressed from Flp-2A-Cre and Flp-IRES-Cre transcription units mediate the highest level of dual recombinase-mediated cassette exchange. Nucleic Acids Res 40(8):e62.

Although the present invention has been described in terms of the preferred embodiments, it is to be understood that such disclosure is not intended to be limiting. Various alterations and modifications will be readily apparent to those of skill in the art. Accordingly, it is intended that the appended claims be interpreted as covering all alterations and modifications as fall within the spirit and scope of the invention. Each or the documents cited herein are incorporated by reference in their entirety.

What is claimed is:

1. A non-naturally occurring chimeric Flp-TAL recombinase comprising a Flp recombinase variant domain and a TAL DNA-binding domain, wherein said chimeric Flp-TAL recombinase has a more narrow or more broad target specificity for FRT-like target sequences, relative to wild-type Flp recombinase.

2. The chimeric Flp-TAL recombinase of claim 1, additionally having a linker peptide that operably connects the Flp recombinase variant domain and the TAL DNA-binding domain.

3. The chimeric Flp-TAL recombinase of claim 2, wherein the linker peptide operably connects the C-terminus of the Flp recombinase variant domain to the N-terminus of the TAL DNA-binding domain.

4. The chimeric Flp-TAL recombinase of claim 2, further having a heterologous nuclear localization signal (NLS) operably linked to the chimeric Flp-TAL recombinase.

5. The chimeric Flp-TAL recombinase of claim 2, wherein the Flp-recombinase variant domain has reduced recombinase activity, relative to wild-type Flp recombinase.

6. The chimeric Flp-TAL recombinase of claim 2, where the Flp recombinase variant domain is broadly specific for a multiplicity of FRT-like sequences.

7. The chimeric Flp-TAL recombinase of claim 2, where the Flp recombinase variant domain has narrow specificity for a desired FRT-like sequence.

8. The chimeric Flp-TAL recombinase of claim 6, where the TAL DNA-binding domain has narrow specificity for a nucleic acid sequence 3-12 bp upstream or downstream of the FRT-like sequence.

9. The chimeric Flp-TAL recombinase of claim 6, where the TAL DNA-binding domain has narrow specificity for a nucleic acid sequence 9-24 bp in length.

10. The chimeric Flp-TAL recombinase of claim 1, where the TAL DNA-binding domain stabilizes the binding of the chimeric recombinase on its target sequence and enhances the recombinase activity of the Flp recombinase variant domain.

11. The chimeric Flp-TAL recombinase of claim 1, wherein the chimeric recombinase is able to recombine a genomic target sequence in a eukaryotic cell.

12. A composition comprising a first chimeric Flp-TAL recombinase of claim 1 and a second chimeric Flp-TAL recombinase of claim 1, where the first chimeric Flp-TAL recombinase contains a TAL DNA-binding domain that has narrow specificity for a nucleic acid sequence upstream of a desired FRT-like sequence and the second chimeric Flp-TAL recombinase contains a TAL DNA-binding domain that has narrow specificity for a nucleic acid sequence downstream of the desired FRT-like sequence.

13. The chimeric Flp-TAL recombinase of claim 2, where the Flp variant domain is evolved from a library Flp genes where genes bearing common as well as unique mutations are used as templates for generating shuffled variant libraries which can be screened to identify the desired target specificity.

14. The chimeric Flp-TAL recombinase of claim 2, where the Flp recombinase variant domain contains at least three mutations selected from the group consisting of A35T, I45V, T50A, S114P, I295F, and A363E of SEQ ID NO: 37.

15. The chimeric Flp-TAL recombinase of claim 2, where the TAL DNA-binding domain contains a core TAL DNA-binding domain that begins at position delta-152 of the N-terminus of the TAL effector and ends at the position +95 as set forth in SEQ ID NO: 37.

16. The chimeric Flp-TAL recombinase of claim 15, where the TAL DNA-binding domain contains additional TAL amino acid sequence extending from the N-terminus and/or the C-terminus of the core TAL DNA-binding domain of the TAL effector, said additional sequence functioning as a linker between the Flp recombinase variant domain and the TAL DNA-binding domain.

17. The chimeric Flp-TAL recombinase of claim 2, where the Flp recombinase variant domain has broad specificity to more than one FRT-like sequence and target specificity is primarily driven by the specificity of the TAL DNA-binding domain.

18. The chimeric Flp-TAL recombinase of claim 2, where the isolated Flp variant domain is substantially unable to recombine an FRT-like genomic target sequence in a eukaryote in the absence of the TAL DNA-binding domain.

* * * * *

SEQUENCE LISTING

```
<160> NUMBER OF SEQ ID NOS: 73

<210> SEQ ID NO 1
<211> LENGTH: 1272
<212> TYPE: DNA
<213> ORGANISM: Artificial Sequence
<220> FEATURE:
<223> OTHER INFORMATION: Thermostable derivitive of wild-type Flp.

<400> SEQUENCE: 1
atgtcacaat tgatatatt  atgtaaaaca  ccacctaagg  tcctggttcg  tcagtttgtg      60
gaaaggtttg aaagaccttc  aggggaaaaa  atagcatcat  gtgctgctga  actaacctat     120
ttatgttgga tgattactca  taacggaaca  gcaatcaaga  gagccacatt  catgagctat     180
aatactatca taagcaattc  gctgagtttc  gatattgtca  acaaatcact  ccagtttaaa     240
tacaagacgc aaaaagcaac  aattctgaa   gcctcattaa  agaaattaat  tcctgcttgg     300
gaatttacaa ttattcctta  caatggacaa  aaacatcaat  ctgatatcac  tgatattgta     360
agtagtttgc aattacagtt  cgaatcatcg  gaagaagcag  ataagggaaa  tagccacagt     420
aaaaaaatgc ttaaagcact  tctaagtgag  ggtgaaagca  tctgggagat  cactgagaaa     480
atactaaatt cgtttgagta  tacctcgaga  tttacaaaaa  caaaaacttt  ataccaattc     540
ctcttcctag ctactttcat  caattgtgga  agattcagcg  atattaagaa  cgttgatccg     600
aaatcattta aattagtcca  aaataagtat  ctgggagtaa  taatccagtg  tttagtgaca     660
gagacaaaga caagcgttag  taggcacata  tacttcttta  gcgcaagggg  taggatcgat     720
ccacttgtat atttggatga  attttttgagg  aattctgaac  cagtcctaaa  acgagtaaat     780
```

```
aggaccggca attcttcaag caacaaacag gaataccaat tattaaaaga taacttagtc      840
agatcgtaca acaaggcttt gaagaaaaat gcgccttatc caatctttgc tataaagaat      900
ggcccaaaat ctcacattgg aagacatttg atgacctcat ttctgtcaat gaagggccta      960
acggagttga ctaatgttgt gggaaattgg agcgataagc gtgcttctgc cgtggccagg     1020
acaacgtata ctcatcagat aacagcaata cctgatcact acttcgcact agtttctcgg     1080
tactatgcat atgatccaat atcaaaggaa atgatagcat tgaaggatga gactaatcca     1140
attgaggagt ggcagcatat agaacagcta aagggtagtg ctgaaggaag catacgatac     1200
cccgcatgga atgggataat atcacaggag gtactagact accttctcatc ctacataaat     1260 agacgcatat aa                                                         1272
```

<210> SEQ ID NO 2
<211> LENGTH: 423
<212> TYPE: PRT
<213> ORGANISM: Artificial Sequence
<220> FEATURE:
<223> OTHER INFORMATION: Amino acid sequence of the thermostable varient
      of Flp, Flpe.

<400> SEQUENCE: 2

```
Met Ser Gln Phe Asp Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
            20                  25                  30

Ser Cys Ala Ala Glu Leu Thr Tyr Leu Cys Trp Met Ile Thr His Asn
        35                  40                  45

Gly Thr Ala Ile Lys Arg Ala Thr Phe Met Ser Tyr Asn Thr Ile Ile
    50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Asn Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
    130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
    210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Ser Asn Lys Gln Glu Tyr
            260                 265                 270
```

```
Gln Leu Leu Lys Asp Asn Leu Val Arg Ser Tyr Asn Lys Ala Leu Lys
            275                 280                 285
Lys Asn Ala Pro Tyr Pro Ile Phe Ala Ile Lys Asn Gly Pro Lys Ser
        290                 295                 300
His Ile Gly Arg His Leu Met Thr Ser Phe Leu Ser Met Lys Gly Leu
305                 310                 315                 320
Thr Glu Leu Thr Asn Val Val Gly Asn Trp Ser Asp Lys Arg Ala Ser
                325                 330                 335
Ala Val Ala Arg Thr Thr Tyr Thr His Gln Ile Thr Ala Ile Pro Asp
            340                 345                 350
His Tyr Phe Ala Leu Val Ser Arg Tyr Tyr Ala Tyr Asp Pro Ile Ser
        355                 360                 365
Lys Glu Met Ile Ala Leu Lys Asp Glu Thr Asn Pro Ile Glu Glu Trp
    370                 375                 380
Gln His Ile Glu Gln Leu Lys Gly Ser Ala Glu Gly Ser Ile Arg Tyr
385                 390                 395                 400
Pro Ala Trp Asn Gly Ile Ile Ser Gln Glu Val Leu Asp Tyr Leu Ser
                405                 410                 415
Ser Tyr Ile Asn Arg Arg Ile
            420

<210> SEQ ID NO 3
<211> LENGTH: 1056
<212> TYPE: DNA
<213> ORGANISM: Artificial Sequence
<220> FEATURE:
<223> OTHER INFORMATION: iCre gene from pDIRE. ICre is a codon optimized
      variant of Cre wt.

<400> SEQUENCE: 3
atggtgccca agaagaagag gaaagtctcc aacctgctga ctgtgcacca aaacctgcct        60 gcccctccctg tggatgccac ctctgatgaa gtcaggaaga acctgatgga catgttcagg      120
gacaggcagg ccttctctga acacacctgg aagatgctcc tgtctgtgtg cagatcctgg      180
gctgcctggt gcaagctgaa caacaggaaa tggttccctg ctgaacctga ggatgtgagg      240
gactacctcc tgtacctgca agccagaggc ctggctgtga gaccatccaa cagcacctg       300 ggccagctca catgctgca caggagatct ggcctgcctc gcccttctga ctccaatgct       360
gtgtccctgg tgatgaggag aatcagaaag gagaatgtgg atgctgggga gagagccaag      420
caggccctgg cctttgaacg cactgacttt gaccaagtca gatccctgat ggagaactct      480
gacagatgcc aggacatcag gaacctggcc ttcctgggca ttgcctacaa caccctgctg      540
cgcattgccg aaattgccag aatcagagtg aaggacatct cccgcaccga tggtgggaga      600
atgctgatcc acattggcag gaccaagacc ctggtgtcca gctggtgt ggagaaggcc       660 ctgtccctgg gggttaccaa gctggtggag atggatct ctgtgtctgg tgtggctgat       720
gaccccaaca actacctgtt ctgccgggtc agaaagaatg gtgtggctgc ccttctgcc     780 acctcccaac tgtccacccg ggccctggaa gggatctttg aggccaccca ccgcctgatc      840
tatggtgcca aggatgactc tgggcagaga tacctggcct ggtctggcca ctctgccaga      900
gtgggtgctg ccagggacat ggccagggct ggtgtgtcca tccctgaaat catgcaggct      960
ggtggctgga ccaatgtgaa cattgtgatg aactacatca gaaacctgga ctctgagact     1020
ggggccatgg tgaggctgct cgaggatggg gactga                               1056
```

```
<210> SEQ ID NO 4
<211> LENGTH: 351
<212> TYPE: PRT
<213> ORGANISM: Artificial Sequence
<220> FEATURE:
<223> OTHER INFORMATION: Amino acid sequence of iCre.

<400> SEQUENCE: 4
```

| Met | Val | Pro | Lys | Lys | Lys | Arg | Lys | Val | Ser | Asn | Leu | Leu | Thr | Val | His |
|---|---|---|---|---|---|---|---|---|---|---|---|---|---|---|---|
| 1 | | | | 5 | | | | | 10 | | | | | 15 | |

Gln Asn Leu Pro Ala Leu Pro Val Asp Ala Thr Ser Asp Glu Val Arg
            20                  25                  30

Lys Asn Leu Met Asp Met Phe Arg Asp Arg Gln Ala Phe Ser Glu His
                35                  40                  45

Thr Trp Lys Met Leu Leu Ser Val Cys Arg Ser Trp Ala Ala Trp Cys
 50                  55                  60

Lys Leu Asn Asn Arg Lys Trp Phe Pro Ala Glu Pro Glu Asp Val Arg
 65                  70                  75                  80

Asp Tyr Leu Leu Tyr Leu Gln Ala Arg Gly Leu Ala Val Lys Thr Ile
                85                  90                  95

Gln Gln His Leu Gly Gln Leu Asn Met Leu His Arg Arg Ser Gly Leu
                100                 105                 110

Pro Arg Pro Ser Asp Ser Asn Ala Val Ser Leu Val Met Arg Arg Ile
            115                 120                 125

Arg Lys Glu Asn Val Asp Ala Gly Glu Arg Ala Lys Gln Ala Leu Ala
        130                 135                 140

Phe Glu Arg Thr Asp Phe Asp Gln Val Arg Ser Leu Met Glu Asn Ser
145                 150                 155                 160

Asp Arg Cys Gln Asp Ile Arg Asn Leu Ala Phe Leu Gly Ile Ala Tyr
                165                 170                 175

Asn Thr Leu Leu Arg Ile Ala Glu Ile Ala Arg Ile Arg Val Lys Asp
            180                 185                 190

Ile Ser Arg Thr Asp Gly Gly Arg Met Leu Ile His Ile Gly Arg Thr
        195                 200                 205

Lys Thr Leu Val Ser Thr Ala Gly Val Glu Lys Ala Leu Ser Leu Gly
210                 215                 220

Val Thr Lys Leu Val Glu Arg Trp Ile Ser Val Ser Gly Val Ala Asp
225                 230                 235                 240

Asp Pro Asn Asn Tyr Leu Phe Cys Arg Val Arg Lys Asn Gly Val Ala
                245                 250                 255

Ala Pro Ser Ala Thr Ser Gln Leu Ser Thr Arg Ala Leu Glu Gly Ile
            260                 265                 270

Phe Glu Ala Thr His Arg Leu Ile Tyr Gly Ala Lys Asp Asp Ser Gly
        275                 280                 285

Gln Arg Tyr Leu Ala Trp Ser Gly His Ser Ala Arg Val Gly Ala Ala
        290                 295                 300

Arg Asp Met Ala Arg Ala Gly Val Ser Ile Pro Glu Ile Met Gln Ala
305                 310                 315                 320

Gly Gly Trp Thr Asn Val Asn Ile Val Met Asn Tyr Ile Arg Asn Leu
                325                 330                 335

Asp Ser Glu Thr Gly Ala Met Val Arg Leu Leu Glu Asp Gly Asp
            340                 345                 350

```
<210> SEQ ID NO 5
<211> LENGTH: 474
<212> TYPE: PRT
```

<213> ORGANISM: Zygosaccharomyces bailii

<400> SEQUENCE: 5

```
Met Ser Glu Phe Ser Glu Leu Val Arg Ile Leu Pro Leu Asp Gln Val
1               5                   10                  15

Ala Glu Ile Lys Arg Ile Leu Ser Arg Gly Asp Pro Ile Pro Leu Gln
            20                  25                  30

Arg Leu Ala Ser Leu Leu Thr Met Val Ile Leu Thr Val Asn Met Ser
        35                  40                  45

Lys Lys Arg Lys Ser Ser Pro Ile Lys Leu Ser Thr Phe Thr Lys Tyr
50                  55                  60

Arg Arg Asn Val Ala Lys Ser Leu Tyr Tyr Asp Met Ser Ser Lys Thr
65                  70                  75                  80

Val Phe Phe Glu Tyr His Leu Lys Asn Thr Gln Asp Leu Gln Glu Gly
                85                  90                  95

Leu Glu Gln Ala Ile Ala Pro Tyr Asn Phe Val Val Lys Val His Lys
            100                 105                 110

Lys Pro Ile Asp Trp Gln Lys Gln Leu Ser Ser Val His Glu Arg Lys
        115                 120                 125

Ala Gly His Arg Ser Ile Leu Ser Asn Asn Val Gly Ala Glu Ile Ser
130                 135                 140

Lys Leu Ala Glu Thr Lys Asp Ser Thr Trp Ser Phe Ile Glu Arg Thr
145                 150                 155                 160

Met Asp Leu Ile Glu Ala Arg Thr Arg Gln Pro Thr Thr Arg Val Ala
                165                 170                 175

Tyr Arg Phe Leu Leu Gln Leu Thr Phe Met Asn Cys Cys Arg Ala Asn
            180                 185                 190

Asp Leu Lys Asn Ala Asp Pro Ser Thr Phe Gln Ile Ile Ala Asp Pro
        195                 200                 205

His Leu Gly Arg Ile Leu Arg Ala Phe Val Pro Glu Thr Lys Thr Ser
210                 215                 220

Ile Glu Arg Phe Ile Tyr Phe Phe Pro Cys Lys Gly Arg Cys Asp Pro
225                 230                 235                 240

Leu Leu Ala Leu Asp Ser Tyr Leu Leu Trp Val Gly Pro Val Pro Lys
                245                 250                 255

Thr Gln Thr Thr Asp Glu Glu Thr Gln Tyr Asp Tyr Gln Leu Leu Gln
            260                 265                 270

Asp Thr Leu Leu Ile Ser Tyr Asp Arg Phe Ile Ala Lys Glu Ser Lys
        275                 280                 285

Glu Asn Ile Phe Lys Ile Pro Asn Gly Pro Lys Ala His Leu Gly Arg
290                 295                 300

His Leu Met Ala Ser Tyr Leu Gly Asn Asn Ser Leu Lys Ser Glu Ala
305                 310                 315                 320

Thr Leu Tyr Gly Asn Trp Ser Val Glu Arg Gln Glu Gly Val Ser Lys
                325                 330                 335

Met Ala Asp Ser Arg Tyr Met His Thr Val Lys Ser Pro Pro Ser
            340                 345                 350

Tyr Leu Phe Ala Phe Leu Ser Gly Tyr Lys Lys Ser Asn Gln Gly
        355                 360                 365

Glu Tyr Val Leu Ala Glu Thr Leu Tyr Asn Pro Leu Asp Tyr Asp Lys
370                 375                 380

Thr Leu Pro Ile Thr Thr Asn Glu Lys Leu Ile Cys Arg Arg Tyr Gly
385                 390                 395                 400
```

-continued

```
Lys Asn Ala Lys Val Ile Pro Lys Asp Ala Leu Leu Tyr Leu Tyr Thr
                405                 410                 415

Tyr Ala Gln Gln Lys Arg Lys Gln Leu Ala Asp Pro Asn Glu Gln Asn
            420                 425                 430

Arg Leu Phe Ser Ser Glu Ser Pro Ala His Pro Phe Leu Thr Pro Gln
        435                 440                 445

Ser Thr Gly Ser Ser Thr Pro Leu Thr Trp Thr Ala Pro Lys Thr Leu
    450                 455                 460

Ser Thr Gly Leu Met Thr Pro Gly Glu Glu
465                 470

<210> SEQ ID NO 6
<211> LENGTH: 568
<212> TYPE: PRT
<213> ORGANISM: Zygosaccharomyces rouxii

<400> SEQUENCE: 6

Met Ser Ser Tyr Met Asp Leu Val Asp Glu Pro Ala Thr Leu Tyr
1                5                  10                  15

His Lys Phe Val Glu Cys Leu Lys Ala Gly Glu Asn Phe Cys Gly Asp
            20                  25                  30

Lys Leu Ser Gly Ile Ile Thr Met Ala Ile Leu Lys Ala Ile Lys Ala
        35                  40                  45

Leu Thr Glu Val Lys Lys Thr Thr Phe Asn Lys Tyr Lys Thr Thr Ile
    50                  55                  60

Lys Gln Gly Leu Gln Tyr Asp Val Gly Ser Ser Thr Ile Ser Phe Val
65                  70                  75                  80

Tyr His Leu Lys Asp Cys Asp Glu Leu Ser Arg Gly Leu Ser Asp Ala
                85                  90                  95

Phe Glu Pro Tyr Lys Phe Lys Ile Lys Ser Asn Lys Glu Ala Thr Ser
            100                 105                 110

Phe Lys Thr Leu Phe Arg Gly Pro Ser Phe Gly Ser Gln Lys Asn Trp
        115                 120                 125

Arg Lys Lys Glu Val Asp Arg Glu Val Asp Asn Leu Phe His Ser Thr
    130                 135                 140

Glu Thr Asp Glu Ser Ile Phe Lys Phe Ile Leu Asn Thr Leu Asp Ser
145                 150                 155                 160

Ile Glu Thr Gln Thr Asn Thr Asp Arg Gln Lys Thr Val Leu Thr Phe
                165                 170                 175

Ile Leu Leu Met Thr Phe Phe Asn Cys Cys Arg Asn Asn Asp Leu Met
            180                 185                 190

Asn Val Asp Pro Ser Thr Phe Lys Ile Val Lys Asn Lys Phe Val Gly
        195                 200                 205

Tyr Leu Leu Gln Ala Glu Val Lys Gln Thr Lys Thr Arg Lys Ser Arg
    210                 215                 220

Asn Ile Phe Phe Phe Pro Ile Arg Glu Asn Arg Phe Asp Leu Phe Leu
225                 230                 235                 240

Ala Leu His Asp Phe Phe Arg Thr Cys Gln Pro Thr Pro Lys Ser Arg
                245                 250                 255

Leu Ser Asp Gln Val Ser Glu Lys Trp Gln Leu Phe Arg Asp Ser
            260                 265                 270

Met Val Ile Asp Tyr Asn Arg Phe Arg Lys Phe Pro Ala Ser Pro
        275                 280                 285

Ile Phe Ala Ile Lys His Gly Pro Lys Ser His Leu Gly Arg His Leu
    290                 295                 300
```

```
Met Asn Ser Phe Leu His Lys Asn Glu Leu Asp Ser Trp Ala Asn Ser
305                 310                 315                 320

Leu Gly Asn Trp Ser Ser Gln Asn Gln Arg Glu Ser Gly Ala Arg
            325                 330                 335

Leu Gly Tyr Thr His Gly Gly Arg Asp Leu Pro Gln Pro Leu Phe Gly
            340                 345                 350

Phe Leu Ala Gly Tyr Cys Val Arg Asn Glu Glu Gly His Ile Val Gly
            355                 360                 365

Leu Gly Leu Glu Lys Asp Ile Asn Asp Leu Phe Asp Gly Ile Met Asp
        370                 375                 380

Pro Leu Asn Glu Lys Glu Asp Thr Glu Ile Cys Glu Ser Tyr Gly Glu
385                 390                 395                 400

Trp Ala Lys Ile Val Ser Lys Asp Val Leu Ile Phe Leu Lys Arg Tyr
                405                 410                 415

His Ser Lys Asn Ala Cys Arg Arg Tyr Gln Asn Ser Thr Leu Tyr Ala
            420                 425                 430

Arg Thr Phe Leu Lys Thr Glu Ser Val Thr Leu Ser Gly Ser Lys Gly
        435                 440                 445

Ser Glu Glu Pro Ser Ser Pro Val Arg Ile Pro Ile Leu Ser Met Gly
    450                 455                 460

Lys Ala Ser Pro Ser Glu Gly Arg Lys Leu Arg Ala Ser Glu His Ala
465                 470                 475                 480

Asn Asp Asp Asn Glu Ile Glu Lys Ile Asp Ser Asp Ser Ser Gln Ser
                485                 490                 495

Glu Glu Ile Pro Ile Glu Met Ser Asp Ser Asp Glu Thr Thr Ala
            500                 505                 510

Ser Asn Ile Ser Gly Ile Tyr Leu Asp Met Ser Lys Ala Asn Ser Asn
            515                 520                 525

Val Val Tyr Ser Pro Pro Ser Gln Thr Gly Arg Ala Ala Gly Ala Gly
        530                 535                 540

Arg Lys Arg Gly Val Gly Gly Arg Arg Thr Val Glu Ser Lys Arg Arg
545                 550                 555                 560

Arg Val Leu Ala Pro Ile Asn Arg
                565

<210> SEQ ID NO 7
<211> LENGTH: 447
<212> TYPE: PRT
<213> ORGANISM: Kluyveromyces drosophilarum

<400> SEQUENCE: 7

Met Ser Thr Phe Ala Glu Ala Ala His Leu Thr Pro His Gln Cys Ala
1               5                   10                  15

Asn Glu Ile Asn Glu Ile Leu Glu Ser Asp Thr Phe Asn Ile Asn Ala
            20                  25                  30

Lys Glu Ile Arg Asn Lys Leu Ala Ser Leu Phe Ser Ile Leu Thr Met
        35                  40                  45

Gln Ser Leu Ser Ile Arg Arg Glu Met Lys Ile Asn Thr Tyr Arg Ser
    50                  55                  60

Tyr Lys Ser Ala Ile Gly Lys Ser Leu Ser Phe Asp Lys Asp Lys
65                  70                  75                  80

Ile Ile Lys Phe Thr Val Arg Leu Arg Lys Thr Glu Ser Leu Gln Lys
                85                  90                  95

Asp Ile Glu Ser Ala Leu Pro Ser Tyr Lys Val Val Val Ser Pro Phe
```

```
            100                 105                 110
Lys Asn Gln Glu Val Ser Leu Phe Asp Arg Tyr Glu Glu Thr His Lys
        115                 120                 125

Tyr Asp Ala Ser Met Val Gly Leu Gln Phe Thr Asn Ile Leu Ser Lys
        130                 135                 140

Glu Lys Asp Ile Trp Lys Ile Val Ser Arg Ile Ala Cys Phe Phe Asp
145                 150                 155                 160

Gln Ser Cys Val Thr Thr Thr Lys Arg Ala Glu Tyr Arg Leu Leu Leu
                165                 170                 175

Leu Gly Ala Val Gly Asn Cys Cys Arg Tyr Ser Asp Leu Lys Asn Leu
            180                 185                 190

Asp Pro Arg Thr Phe Glu Ile Tyr Asn Asn Ser Phe Leu Gly Pro Ile
        195                 200                 205

Val Arg Ala Thr Val Thr Glu Thr Lys Ser Arg Thr Glu Arg Tyr Val
        210                 215                 220

Asn Phe Tyr Pro Val Asn Gly Asp Cys Asp Leu Leu Ile Ser Leu Tyr
225                 230                 235                 240

Asp Tyr Leu Arg Val Cys Ser Pro Ile Glu Lys Thr Val Ser Ser Asn
                245                 250                 255

Arg Pro Thr Asn Gln Thr His Gln Phe Leu Pro Glu Ser Leu Ala Arg
                260                 265                 270

Thr Phe Ser Arg Phe Leu Thr Gln His Val Asp Glu Pro Val Phe Lys
            275                 280                 285

Ile Trp Asn Gly Pro Lys Ser His Phe Gly Arg His Leu Met Ala Thr
        290                 295                 300

Phe Leu Ser Arg Ser Glu Lys Gly Lys Tyr Val Ser Ser Leu Gly Asn
305                 310                 315                 320

Trp Ala Gly Asp Arg Glu Ile Gln Ser Ala Val Ala Arg Ser His Tyr
                325                 330                 335

Ser His Gly Ser Val Thr Val Asp Asp Arg Val Phe Ala Phe Ile Ser
                340                 345                 350

Gly Phe Tyr Lys Glu Ala Pro Leu Gly Ser Glu Ile Tyr Val Leu Lys
            355                 360                 365

Asp Pro Ser Asn Lys Pro Leu Ser Arg Glu Glu Leu Leu Glu Glu Glu
        370                 375                 380

Gly Asn Ser Leu Gly Ser Pro Pro Leu Ser Pro Ser Ser Pro Arg
385                 390                 395                 400

Leu Val Ala Gln Ser Phe Ser Ala His Pro Ser Leu Gln Leu Phe Glu
                405                 410                 415

Gln Trp His Gly Ile Ile Ser Asp Glu Val Leu Gln Phe Ile Ala Glu
            420                 425                 430

Tyr Arg Arg Lys His Glu Leu Arg Ser Gln Arg Thr Val Val Ala
        435                 440                 445

<210> SEQ ID NO 8
<211> LENGTH: 413
<212> TYPE: PRT
<213> ORGANISM: Kluyveromyces waltii

<400> SEQUENCE: 8

Met Ser Val Phe Glu Glu Leu Ile Ser Lys Asn Leu Met Ser Leu Met
1               5                   10                  15

Glu Glu Leu Met Ser Met Leu Thr Asn Glu Lys Glu Phe Gln Arg Glu
            20                  25                  30
```

-continued

Arg Phe Ala Ser Leu Leu Ala Tyr Met Ile Met Ala Thr Gly Glu Leu
           35                  40                  45

Glu Glu Lys Lys Leu Ser Thr Phe Thr Lys Tyr Ser Arg Arg Ile Arg
 50                  55                  60

Gln Thr Val Glu Phe Asp Ser Asn Asn Gln Ile Val Arg Phe Glu Tyr
 65                  70                  75                  80

His Leu Lys Asn Pro Thr Glu Leu Lys Glu Thr Leu Asp Lys Ala Phe
                 85                  90                  95

Lys Pro Val Val Phe Glu Ile Lys Ser Lys Lys Val Val Ser Met
                100                 105                 110

Leu Glu Leu Ala Ala Lys Leu Asp Lys Arg Gly Ser Asp Ser Ala Gly
            115                 120                 125

Gly Thr Val Ala Ser Glu Val Ser Lys Leu Val Arg Glu Glu Glu Ile
        130                 135                 140

Trp Leu Leu Leu Val Asn Val Lys Asn Thr Ile Gln Glu Lys Val Arg
145                 150                 155                 160

Lys Ser Ser Leu Arg Ala Glu Leu Thr Tyr Ile Leu Thr Ala Ser Phe
                165                 170                 175

Phe Asn Cys Cys Arg His Ser Asp Leu Arg Asn Ala Asp Pro Ala Thr
            180                 185                 190

Phe Glu Leu Val Pro Asn Lys Tyr Val Gly His Val Arg Val Leu
        195                 200                 205

Val Cys Glu Thr Lys Thr Arg Lys Pro Arg Phe Ile Tyr Phe Phe Pro
    210                 215                 220

Val Asn Thr Ala Ala Asp Pro Leu Val Ala Leu His Asp Leu Phe Ser
225                 230                 235                 240

Ser Thr Phe Pro Ser Lys Lys Ser Arg Thr Ser Glu Arg Lys Gln Glu
                245                 250                 255

Gln Glu Trp Gln Ile Val Arg Asp Ala Ser Ile Asn Asn Tyr Asp Arg
            260                 265                 270

Phe Val Gly Lys His Ala Thr Glu Ser Val Phe Ala Ile Leu His Gly
        275                 280                 285

Pro Lys Ser His Leu Gly Arg His Leu Met Ser Ser Tyr Leu Ala Tyr
    290                 295                 300

Thr His His Gly Glu Trp Val Ser Pro Tyr Gly Asn Trp Ser Ala Gly
305                 310                 315                 320

Lys Gly Thr Ile Glu Ser Ser Val Ala Arg Ala Lys Tyr Ala His Val
                325                 330                 335

Gln Ala Glu Ile Pro Ser Asp Leu Phe Ala Phe Leu Ser Gln Tyr Tyr
            340                 345                 350

Gln Glu Ser Lys Ser Gly Asp Phe Glu Leu Asn Asp Thr Ser Lys Asp
        355                 360                 365

Pro Thr Lys Leu Val Arg His Ser Ala Ser Gln Leu Glu Ile Asn Arg
    370                 375                 380

Thr Tyr Gly Pro Trp Ser Arg Leu Val Asn Lys Asp Val Leu Gly Phe
385                 390                 395                 400

Val His Ser Tyr Ala Met Ala Lys Arg Tyr Glu Gly Lys
                405                 410

<210> SEQ ID NO 9
<211> LENGTH: 490
<212> TYPE: PRT
<213> ORGANISM: Zygosaccharomyces rouxii

<400> SEQUENCE: 9

```
Met Gln Leu Thr Lys Asp Thr Glu Ile Ser Thr Ile Asn Arg Gln Met
1               5                   10                  15

Ser Asp Phe Ser Glu Leu Ser Gln Ile Leu Pro Leu His Gln Ile Ser
            20                  25                  30

Lys Ile Lys Asp Ile Leu Glu Asn Gly Asn Pro Leu Pro Lys Glu Lys
        35                  40                  45

Leu Ala Ser His Leu Thr Met Ile Ile Leu Met Ala Asn Leu Ala Ser
    50                  55                  60

Gln Lys Arg Lys Asp Val Pro Val Lys Arg Ser Thr Phe Leu Lys Tyr
65              70                  75                  80

Gln Arg Ser Ile Ser Lys Thr Leu Gln Tyr Asp Ser Ser Thr Lys Thr
                85                  90                  95

Val Ser Phe Glu Tyr His Leu Lys Asp Pro Ser Lys Leu Ile Lys Gly
                100                 105                 110

Leu Glu Asp Val Val Ser Pro Tyr Arg Phe Val Val Gly Val His Glu
        115                 120                 125

Lys Pro Asp Asp Val Met Ser His Leu Ser Ala Val His Met Arg Lys
    130                 135                 140

Glu Ala Gly Arg Lys Arg Asp Leu Gly Asn Lys Ile Asn Asp Glu Ile
145                 150                 155                 160

Thr Lys Ile Ala Glu Thr Gln Glu Thr Ile Trp Gly Phe Val Gly Lys
                165                 170                 175

Thr Met Asp Leu Ile Glu Ala Arg Thr Thr Arg Pro Thr Thr Lys Ala
            180                 185                 190

Ala Tyr Asn Leu Leu Leu Gln Ala Thr Phe Met Asn Cys Cys Arg Ala
        195                 200                 205

Asp Asp Leu Lys Asn Thr Asp Ile Lys Thr Phe Glu Val Ile Pro Asp
210                 215                 220

Lys His Leu Gly Arg Met Leu Arg Ala Phe Val Pro Glu Thr Lys Thr
225                 230                 235                 240

Gly Thr Arg Phe Val Tyr Phe Phe Pro Cys Lys Gly Arg Cys Asp Pro
                245                 250                 255

Leu Leu Ala Leu Asp Ser Tyr Leu Gln Trp Thr Asp Pro Ile Pro Lys
            260                 265                 270

Thr Arg Thr Thr Asp Glu Asp Ala Arg Tyr Asp Tyr Gln Leu Leu Arg
        275                 280                 285

Asn Ser Leu Leu Gly Ser Tyr Asp Gly Phe Ile Ser Lys Gln Ser Asp
    290                 295                 300

Glu Ser Ile Phe Lys Ile Pro Asn Gly Pro Lys Ala His Leu Gly Arg
305                 310                 315                 320

His Val Thr Ala Ser Tyr Leu Ser Asn Asn Glu Met Asp Lys Glu Ala
                325                 330                 335

Thr Leu Tyr Gly Asn Trp Ser Ala Ala Arg Glu Glu Gly Val Ser Arg
            340                 345                 350

Val Ala Lys Ala Arg Tyr Met His Thr Ile Glu Lys Ser Pro Pro Ser
        355                 360                 365

Tyr Leu Phe Ala Phe Leu Ser Gly Phe Tyr Asn Ile Thr Ala Glu Arg
    370                 375                 380

Ala Cys Glu Leu Val Asp Pro Asn Ser Asn Pro Cys Glu Gln Asp Lys
385                 390                 395                 400

Asn Ile Pro Met Ile Ser Asp Ile Glu Thr Leu Met Ala Arg Tyr Gly
                405                 410                 415
```

```
Lys Asn Ala Glu Ile Ile Pro Met Asp Val Leu Val Phe Leu Ser Ser
                420                 425                 430

Tyr Ala Arg Phe Lys Asn Asn Glu Gly Lys Glu Tyr Lys Leu Gln Ala
            435                 440                 445

Arg Ser Ser Arg Gly Val Pro Asp Phe Pro Asp Asn Gly Arg Thr Ala
        450                 455                 460

Leu Tyr Asn Ala Leu Thr Ala Ala His Val Lys Arg Lys Ile Ser
465                 470                 475                 480

Ile Val Val Gly Arg Ser Ile Asp Thr Ser
                485                 490

<210> SEQ ID NO 10
<211> LENGTH: 414
<212> TYPE: PRT
<213> ORGANISM: Zygosaccharomyces fermentati

<400> SEQUENCE: 10

Met Ser Leu Phe Glu Glu Leu Val Ser Arg Asn Ile Thr Ser Leu Val
1               5                   10                  15

Asn Glu Leu Lys Glu Met Leu Asn Ser Glu His Lys Leu Pro Ser Glu
                20                  25                  30

Lys Phe Ala Ser Leu Leu Ala Tyr Val Ile Met Ala Thr Phe Ser Lys
            35                  40                  45

Leu Ser Glu Arg Lys Arg Ser Thr Phe Ile Lys Tyr Ser Arg Glu Ile
        50                  55                  60

Arg Gln Ser Val Gln Tyr Asp Arg Glu Ala Gln Ile Val Lys Phe Asn
65                  70                  75                  80

Tyr His Leu Lys Arg Pro His Glu Leu Lys Asp Val Leu Asp Lys Thr
                85                  90                  95

Phe Ala Pro Ile Val Phe Glu Val Ser Ser Thr Lys Lys Val Glu Ser
            100                 105                 110

Met Val Glu Leu Ala Ala Lys Met Asp Lys Val Glu Gly Lys Gly Gly
        115                 120                 125

His Asn Ala Val Ala Glu Glu Ile Thr Lys Ile Val Arg Ala Asp Asp
    130                 135                 140

Ile Trp Thr Leu Leu Ser Gly Val Glu Val Thr Ile Gln Lys Arg Ala
145                 150                 155                 160

Phe Lys Arg Ser Leu Arg Ala Glu Leu Lys Tyr Val Leu Ile Thr Ser
                165                 170                 175

Phe Phe Asn Cys Ser Arg His Ser Asp Leu Lys Asn Ala Asp Pro Thr
            180                 185                 190

Lys Phe Glu Leu Val Lys Asn Arg Tyr Leu Asn Arg Val Leu Arg Val
        195                 200                 205

Leu Val Cys Glu Thr Lys Thr Arg Lys Pro Arg Tyr Ile Tyr Phe Phe
    210                 215                 220

Pro Val Asn Lys Lys Thr Asp Pro Leu Ile Ala Leu His Asp Leu Phe
225                 230                 235                 240

Ser Glu Ala Glu Pro Val Pro Lys Ser Arg Ala Ser His Gln Lys Thr
                245                 250                 255

Asp Gln Glu Trp Gln Met Leu Arg Asp Ser Leu Leu Thr Asn Tyr Asp
            260                 265                 270

Arg Phe Ile Ala Thr His Ala Lys Gln Ala Val Phe Gly Ile Lys His
        275                 280                 285

Gly Pro Lys Ser His Leu Gly Arg His Leu Met Ser Ser Tyr Leu Ser
    290                 295                 300
```

```
His Thr Asn His Gly Gln Trp Val Ser Pro Phe Gly Asn Trp Ser Ala
305                 310                 315                 320

Gly Lys Asp Thr Val Glu Ser Asn Val Ala Arg Ala Lys Tyr Val His
            325                 330                 335

Ile Gln Ala Asp Ile Pro Asp Glu Leu Phe Ala Phe Leu Ser Gln Tyr
            340                 345                 350

Tyr Ile Gln Thr Pro Ser Gly Asp Phe Glu Leu Ile Asp Ser Ser Glu
        355                 360                 365

Gln Pro Thr Thr Phe Ile Asn Asn Leu Ser Thr Gln Glu Asp Ile Ser
    370                 375                 380

Lys Ser Tyr Gly Thr Trp Thr Gln Val Val Gly Gln Asp Val Leu Glu
385                 390                 395                 400

Tyr Val His Ser Tyr Ala Met Gly Lys Leu Gly Ile Arg Lys
                405                 410
```

<210> SEQ ID NO 11
<211> LENGTH: 427
<212> TYPE: PRT
<213> ORGANISM: Torulaspora delbrueckii

<400> SEQUENCE: 11

```
Met Ser Glu Phe Arg Lys Leu Leu Glu Thr Asn Ile Glu Val Thr Lys
1               5                   10                  15

Gln Lys Ile Leu Glu Ile Leu Cys Ser Gly Ser Leu Pro Gln His Lys
            20                  25                  30

Asp Gln Phe Gly Ala Tyr Met Ala Met Thr Ile Leu Lys Tyr Asn Ala
        35                  40                  45

Leu Asn Gly Arg Ser Met Glu Glu Ala Arg Glu Ile Lys Ile Asn Thr
    50                  55                  60

Phe Lys Lys Tyr Arg Ser Leu Ile Ala Asn Thr Val Thr Phe Arg Ala
65                  70                  75                  80

Asp Asp Asn Val Val Ser Phe Lys Tyr His Thr Gly Arg Met Gln Asp
                85                  90                  95

Leu Asn Glu Gln Leu Ser Ala Tyr Phe Lys Asp Ile Asn Phe Asp Ile
            100                 105                 110

Gln Ser Val Arg Lys Thr Ser Met Asp Thr Val Phe Ser Gly Lys Glu
        115                 120                 125

Ile Lys Ile Val Lys Arg Ser Thr Lys Leu Glu Gly Ser Lys Leu Ile
    130                 135                 140

Asn Glu Ala Phe Ser Lys Leu Val Thr Leu Asn Met Arg Leu Gly His
145                 150                 155                 160

Asp Ile Val Val Pro Val Met Lys Ser Ile Thr Asp Tyr Thr Lys Ser
                165                 170                 175

Ala Ser Thr Asn Ala Glu Tyr Ser Phe Met Phe Leu Leu Thr Val Tyr
            180                 185                 190

Asn Cys Cys Arg Gln Ser Asp Leu Lys Asn Leu Asp Pro Glu Thr Phe
        195                 200                 205

Glu Ile Ile His Asn Thr Phe Leu Gly Arg Met Ile Arg Ala Leu Val
    210                 215                 220

Thr Asp Thr Lys Thr Arg Lys Ala Arg Phe Ile Tyr Phe Tyr Pro Val
225                 230                 235                 240

Ala Gly Pro His Asp Pro Ile Leu Ala Leu His Tyr Leu Leu Cys Glu
                245                 250                 255

Thr Lys Pro Lys Met Lys Ser Leu Thr Ser Asn Ile Glu Ser Asp Gln
```

```
                    260                 265                 270
Gln Tyr Gln Leu Leu Arg Glu Asn Leu Val Thr Gln Tyr Asp Arg Phe
                275                 280                 285
Leu Ala Lys Arg Arg Pro Leu Gly Leu Phe Gly Ile Thr His Gly Pro
            290                 295                 300
Lys Ser His Phe Gly Arg His Leu Met Thr Thr Tyr Leu Ser Thr His
305                 310                 315                 320
Asn Leu Gly Glu Leu Val Thr Pro Phe Gly Asn Trp Cys Ala Thr Asp
                325                 330                 335
Asp Leu Ile Ser Ser Lys Thr Ala Arg Ser Asn Tyr Gly His Arg Thr
            340                 345                 350
Gln Glu Ile Pro Asp His Leu Phe Gly Phe Leu Ser Asp Phe Tyr Arg
        355                 360                 365
Leu Glu Asp Gly Lys Tyr Val Leu Val Asp Gln Arg Asp Pro Lys
    370                 375                 380
Met Ala Asp Arg Gln Leu Glu Cys Ser Thr Thr Tyr Glu Thr Pro Tyr
385                 390                 395                 400
Gly Ser Trp Gln Glu Leu Ile Lys Ala Glu Val Leu Ser Phe Val Trp
                405                 410                 415
Tyr Tyr Ser Gln Arg Arg Leu Gln Gln Ala Ala
            420                 425

<210> SEQ ID NO 12
<211> LENGTH: 34
<212> TYPE: DNA
<213> ORGANISM: Artificial Sequence
<220> FEATURE:
<223> OTHER INFORMATION: Consensus recongition sequence for the
      wild-type recombinase Flp.

<400> SEQUENCE: 12
gaagttccta tactttctag agaataggaa cttc                               34

<210> SEQ ID NO 13
<211> LENGTH: 34
<212> TYPE: DNA
<213> ORGANISM: Bacteriophage P1

<400> SEQUENCE: 13
ataacttcgt ataatgtatg ctatacgaag ttat                               34

<210> SEQ ID NO 14
<211> LENGTH: 34
<212> TYPE: PRT
<213> ORGANISM: Artificial Sequence
<220> FEATURE:
<223> OTHER INFORMATION: Consensus sequence of TAL DBD repeat.

<400> SEQUENCE: 14

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 15
<211> LENGTH: 830
<212> TYPE: PRT
<213> ORGANISM: Artificial Sequence
<220> FEATURE:
```

<223> OTHER INFORMATION: TAL-18 is a representative sequence of a TAL DBD.

<400> SEQUENCE: 15

Met Val Asp Leu Arg Thr Leu Gly Tyr Ser Gln Gln Gln Gln Glu Lys
1               5                   10                  15

Ile Lys Pro Lys Val Arg Ser Thr Val Ala Gln His His Glu Ala Leu
            20                  25                  30

Val Gly His Gly Phe Thr His Ala His Ile Val Ala Leu Ser Gln His
        35                  40                  45

Pro Ala Ala Leu Gly Thr Val Ala Val Thr Tyr Gln His Ile Ile Thr
    50                  55                  60

Ala Leu Pro Glu Ala Thr His Glu Asp Ile Val Gly Val Gly Lys Gln
65                  70                  75                  80

Trp Ser Gly Ala Arg Ala Leu Glu Ala Leu Leu Thr Asp Ala Gly Glu
                85                  90                  95

Leu Arg Gly Pro Pro Leu Gln Leu Asp Thr Gly Gln Leu Val Lys Ile
            100                 105                 110

Ala Lys Arg Gly Gly Val Thr Ala Met Glu Ala Val His Ala Ser Arg
        115                 120                 125

Asn Ala Leu Thr Gly Ala Pro Leu Asn Leu Thr Pro Asp Gln Val Val
    130                 135                 140

Ala Ile Ala Ser Asn Asn Gly Gly Lys Gln Ala Leu Glu Thr Val Gln
145                 150                 155                 160

Arg Leu Leu Pro Val Leu Cys Gln Asp His Gly Leu Thr Pro Asp Gln
                165                 170                 175

Val Val Ala Ile Ala Ser His Asp Gly Gly Lys Gln Ala Leu Glu Thr
            180                 185                 190

Val Gln Arg Leu Leu Pro Val Leu Cys Gln Asp His Gly Leu Thr Pro
        195                 200                 205

Asp Gln Val Val Ala Ile Ala Ser Asn Ile Gly Gly Lys Gln Ala Leu
    210                 215                 220

Glu Thr Val Gln Arg Leu Leu Pro Val Leu Cys Gln Asp His Gly Leu
225                 230                 235                 240

Thr Pro Asp Gln Val Val Ala Ile Ala Ser Asn Gly Gly Lys Gln
                245                 250                 255

Ala Leu Glu Thr Val Gln Arg Leu Leu Pro Val Leu Cys Gln Asp His
            260                 265                 270

Gly Leu Thr Pro Asp Gln Val Val Ala Ile Ala Ser Asn Ile Gly Gly
        275                 280                 285

Lys Gln Ala Leu Glu Thr Val Gln Arg Leu Leu Pro Val Leu Cys Gln
    290                 295                 300

Asp His Gly Leu Thr Pro Asp Gln Val Val Ala Ile Ala Ser Asn Gly
305                 310                 315                 320

Gly Gly Lys Gln Ala Leu Glu Thr Val Gln Arg Leu Leu Pro Val Leu
                325                 330                 335

Cys Gln Asp His Gly Leu Thr Pro Asp Gln Val Val Ala Ile Ala Ser
            340                 345                 350

Asn Gly Gly Gly Lys Gln Ala Leu Glu Thr Val Gln Arg Leu Leu Pro
        355                 360                 365

Val Leu Cys Gln Asp His Gly Leu Thr Pro Asp Gln Val Val Ala Ile
    370                 375                 380

Ala Ser His Asp Gly Gly Lys Gln Ala Leu Glu Thr Val Gln Arg Leu
385                 390                 395                 400

-continued

```
Leu Pro Val Leu Cys Gln Asp His Gly Leu Thr Pro Asp Gln Val Val
            405                 410                 415

Ala Ile Ala Ser Asn Ile Gly Gly Lys Gln Ala Leu Glu Thr Val Gln
            420                 425                 430

Arg Leu Leu Pro Val Leu Cys Gln Asp His Gly Leu Thr Pro Asp Gln
            435                 440                 445

Val Val Ala Ile Ala Ser Asn Gly Gly Lys Gln Ala Leu Glu Thr
450                 455                 460

Val Gln Arg Leu Leu Pro Val Leu Cys Gln Asp His Gly Leu Thr Pro
465                 470                 475                 480

Asp Gln Val Val Ala Ile Ala Ser Asn Ile Gly Gly Lys Gln Ala Leu
            485                 490                 495

Glu Thr Val Gln Arg Leu Leu Pro Val Leu Cys Gln Asp His Gly Leu
            500                 505                 510

Thr Pro Asp Gln Val Val Ala Ile Ala Ser Asn Ile Gly Gly Lys Gln
            515                 520                 525

Ala Leu Glu Thr Val Gln Arg Leu Leu Pro Val Leu Cys Gln Asp His
            530                 535                 540

Gly Leu Thr Pro Asp Gln Val Val Ala Ile Ala Ser Asn Gly Gly Gly
545                 550                 555                 560

Lys Gln Ala Leu Glu Thr Val Gln Arg Leu Leu Pro Val Leu Cys Gln
            565                 570                 575

Asp His Gly Leu Thr Pro Asp Gln Val Val Ala Ile Ala Ser His Asp
            580                 585                 590

Gly Gly Lys Gln Ala Leu Glu Thr Val Gln Arg Leu Leu Pro Val Leu
            595                 600                 605

Cys Gln Asp His Gly Leu Thr Pro Asp Gln Val Val Ala Ile Ala Ser
            610                 615                 620

Asn Gly Gly Lys Gln Ala Leu Glu Thr Val Gln Arg Leu Leu Pro
625                 630                 635                 640

Val Leu Cys Gln Asp His Gly Leu Thr Pro Asp Gln Val Val Ala Ile
            645                 650                 655

Ala Ser His Asp Gly Gly Lys Gln Ala Leu Glu Thr Val Gln Arg Leu
            660                 665                 670

Leu Pro Val Leu Cys Gln Asp His Gly Leu Thr Pro Asp Gln Val Val
            675                 680                 685

Ala Ile Ala Ser His Asp Gly Gly Lys Gln Ala Leu Glu Thr Val Gln
            690                 695                 700

Arg Leu Leu Pro Val Leu Cys Gln Asp His Gly Leu Thr Pro Asp Gln
705                 710                 715                 720

Val Val Ala Ile Ala Ser His Asp Gly Gly Lys Gln Ala Leu Glu Ser
            725                 730                 735

Ile Val Ala Gln Leu Ser Arg Pro Asp Pro Ala Leu Ala Ala Leu Thr
            740                 745                 750

Asn Asp His Leu Val Ala Leu Ala Cys Leu Gly Gly Arg Pro Ala Met
            755                 760                 765

Asp Ala Val Lys Lys Gly Leu Pro His Ala Pro Glu Leu Ile Arg Arg
            770                 775                 780

Val Asn Arg Arg Ile Gly Glu Arg Thr Ser His Arg Val Ala Asp Tyr
785                 790                 795                 800

Ala Gln Val Val Arg Val Leu Glu Phe Phe Gln Cys His Ser His Pro
            805                 810                 815
```

```
Ala Tyr Ala Phe Asp Glu Ala Met Thr Gln Phe Gly Met Ser
        820                 825                 830
```

<210> SEQ ID NO 16
<211> LENGTH: 34
<212> TYPE: DNA
<213> ORGANISM: Artificial Sequence
<220> FEATURE:
<223> OTHER INFORMATION: sequence of the genomic FRT-like sequence FL61.
      Sequence arranced as Flp binding element-spacer-Flp binding
      element.

<400> SEQUENCE: 16
catggtccaa gtctgataat agaaatggca ttgt                          34

<210> SEQ ID NO 17
<211> LENGTH: 34
<212> TYPE: DNA
<213> ORGANISM: Artificial Sequence
<220> FEATURE:
<223> OTHER INFORMATION: Sequence of the genomic FRT-like sequence FL63.
      Sequence is arranged as Flp binding element-spacer-Flp binding
      element.

<400> SEQUENCE: 17
cacctgctaa ttctgcactt agaataatcc tttt                          34

<210> SEQ ID NO 18
<211> LENGTH: 34
<212> TYPE: DNA
<213> ORGANISM: Artificial Sequence
<220> FEATURE:
<223> OTHER INFORMATION: Sequence of the geneomic FRT-like sequence
      FL71. The sequence is arranged as Flp binding element-spacer-Flp
      binding element.

<400> SEQUENCE: 18
cctagtacat tactatttgg aatatatgtg tgct                          34

<210> SEQ ID NO 19
<211> LENGTH: 75
<212> TYPE: DNA
<213> ORGANISM: Artificial Sequence
<220> FEATURE:
<223> OTHER INFORMATION: FL-61 and flanking TAL-targeted sequences

<400> SEQUENCE: 19
ttcacgactg acatcaccgt catggtccaa gtctgataat agaaatggca ttgtcacttt    60
cttccctact gcaac                                                    75

<210> SEQ ID NO 20
<211> LENGTH: 76
<212> TYPE: DNA
<213> ORGANISM: Artificial Sequence
<220> FEATURE:
<223> OTHER INFORMATION: FL-63 and flanking TAL-targeted sequences

<400> SEQUENCE: 20
caaattatgc ataccagctc tcacctgcta attctgcact tagaataatc cttttgtctc    60
tccacatggg tatggg                                                   76

<210> SEQ ID NO 21
<211> LENGTH: 84
<212> TYPE: DNA
<213> ORGANISM: Artificial Sequence
<220> FEATURE:

```
<223> OTHER INFORMATION: FL-71 and flanking TAL-target sequences;
      (TAL/L24-TAL/R15)

<400> SEQUENCE: 21
gtaacttaaa aaaaaacttt acacagtctg cctagtacat tactatttgg aatatatgtg    60
tgcttatttg catattcata atct                                          84

<210> SEQ ID NO 22
<211> LENGTH: 15
<212> TYPE: DNA
<213> ORGANISM: Artificial Sequence
<220> FEATURE:
<223> OTHER INFORMATION: FL-61_TAL(L) TAL DBD target sequence

<400> SEQUENCE: 22
gatgtcagtc gtgaa                                                    15

<210> SEQ ID NO 23
<211> LENGTH: 15
<212> TYPE: DNA
<213> ORGANISM: Artificial Sequence
<220> FEATURE:
<223> OTHER INFORMATION: Sequence targeted by FL-61_TAL(R) TAL DBD.

<400> SEQUENCE: 23
cttccctact gcaac                                                    15

<210> SEQ ID NO 24
<211> LENGTH: 15
<212> TYPE: DNA
<213> ORGANISM: Artificial Sequence
<220> FEATURE:
<223> OTHER INFORMATION: Sequence targeted by the FL-63_TAL(L) DBD.

<400> SEQUENCE: 24
ggtatgcata atttg                                                    15

<210> SEQ ID NO 25
<211> LENGTH: 15
<212> TYPE: DNA
<213> ORGANISM: Artificial Sequence
<220> FEATURE:
<223> OTHER INFORMATION: Target sequence of the FL-63_TAL(R) TAL DBD

<400> SEQUENCE: 25
ccacatgggt atggg                                                    15

<210> SEQ ID NO 26
<211> LENGTH: 24
<212> TYPE: DNA
<213> ORGANISM: Artificial Sequence
<220> FEATURE:
<223> OTHER INFORMATION: Target sequence of FL-71_TAL(L) TAL DBD

<400> SEQUENCE: 26
gtgtaaagtt ttttttaag ttac                                           24

<210> SEQ ID NO 27
<211> LENGTH: 15
<212> TYPE: DNA
<213> ORGANISM: Artificial Sequence
<220> FEATURE:
<223> OTHER INFORMATION: Target sequence for FL-71_TAL(R)

<400> SEQUENCE: 27
```

-continued gcatattcat aatct 15

<210> SEQ ID NO 28
<211> LENGTH: 496
<212> TYPE: PRT
<213> ORGANISM: Artificial Sequence
<220> FEATURE:
<223> OTHER INFORMATION: Tandem repeats within the TAL DBD to bind to
      GATGTCAGTCGTGAA.

<400> SEQUENCE: 28

```
Leu Thr Pro Asp Gln Val Val Ala Ile Ala Ser Asn Asn Gly Gly Lys
1               5                   10                  15

Gln Ala Leu Glu Thr Val Gln Arg Leu Leu Pro Val Leu Cys Gln Asp
            20                  25                  30

His Gly Leu Thr Pro Asp Gln Val Val Ala Ile Ala Ser Asn Ile Gly
        35                  40                  45

Gly Lys Gln Ala Leu Glu Thr Val Gln Arg Leu Leu Pro Val Leu Cys
    50                  55                  60

Gln Asp His Gly Leu Thr Pro Asp Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Asp His Gly Leu Thr Pro Asp Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Asp His Gly Leu Thr Pro Asp Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Asp His Gly Leu Thr Pro Asp Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Asp His Gly Leu Thr Pro Asp
        195                 200                 205

Gln Val Val Ala Ile Ala Ser Asn Ile Gly Gly Lys Gln Ala Leu Glu
    210                 215                 220

Thr Val Gln Arg Leu Leu Pro Val Leu Cys Gln Asp His Gly Leu Thr
225                 230                 235                 240

Pro Asp Gln Val Val Ala Ile Ala Ser Asn Asn Gly Gly Lys Gln Ala
                245                 250                 255

Leu Glu Thr Val Gln Arg Leu Leu Pro Val Leu Cys Gln Asp His Gly
            260                 265                 270

Leu Thr Pro Asp Gln Val Val Ala Ile Ala Ser Asn Gly Gly Gly Lys
        275                 280                 285

Gln Ala Leu Glu Thr Val Gln Arg Leu Leu Pro Val Leu Cys Gln Asp
    290                 295                 300

His Gly Leu Thr Pro Asp Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Asp His Gly Leu Thr Pro Asp Gln Val Val Ala Ile Ala Ser Asn
            340                 345                 350
```

```
Asn Gly Gly Lys Gln Ala Leu Glu Thr Val Gln Arg Leu Leu Pro Val
            355                 360                 365

Leu Cys Gln Asp His Gly Leu Thr Pro Asp Gln Val Val Ala Ile Ala
370                 375                 380

Ser Asn Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
                405                 410                 415

Ile Ala Ser Asn Gly Gly Lys Gln Ala Leu Glu Thr Val Gln Arg
            420                 425                 430

Leu Leu Pro Val Leu Cys Gln Asp His Gly Leu Thr Pro Asp Gln Val
435                 440                 445

Val Ala Ile Ala Ser Asn Ile Gly Gly Lys Gln Ala Leu Glu Thr Val
            450                 455                 460

Gln Arg Leu Leu Pro Val Leu Cys Gln Asp His Gly Leu Thr Pro Asp
465                 470                 475                 480

Gln Val Val Ala Ile Ala Ser Asn Ile Gly Gly Lys Gln Ala Leu Glu
                485                 490                 495
```

<210> SEQ ID NO 29
<211> LENGTH: 496
<212> TYPE: PRT
<213> ORGANISM: Artificial Sequence
<220> FEATURE:
<223> OTHER INFORMATION: Tandem repeats within the FL-61_TAL(R) TAL DBD
      to bind to CTTCCCTACTGCAAC

<400> SEQUENCE: 29

```
Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly Leu Thr Pro Asp Gln Val Val Ala Ile Ala Ser Asn Gly Gly
        35                  40                  45

Gly Lys Gln Ala Leu Glu Thr Val Gln Arg Leu Leu Pro Val Leu Cys
50                  55                  60

Gln Asp His Gly Leu Thr Pro Asp Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Asp His Gly Leu Thr Pro Asp Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Asp His Gly Leu Thr Pro Asp Gln Val Val Ala
130                 135                 140

Ile Ala Ser His Asp Gly Gly Lys Gln Ala Leu Glu Thr Val Gln Arg
145                 150                 155                 160

Leu Leu Pro Val Leu Cys Gln Asp His Gly Leu Thr Pro Asp Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Asp His Gly Leu Thr Pro Asp
        195                 200                 205

Gln Val Val Ala Ile Ala Ser Asn Gly Gly Gly Lys Gln Ala Leu Glu
210                 215                 220
```

Thr Val Gln Arg Leu Leu Pro Val Leu Cys Gln Asp His Gly Leu Thr
225                 230                 235                 240

Pro Asp Gln Val Val Ala Ile Ala Ser Asn Ile Gly Gly Lys Gln Ala
            245                 250                 255

Leu Glu Thr Val Gln Arg Leu Leu Pro Val Leu Cys Gln Asp His Gly
        260                 265                 270

Leu Thr Pro Asp Gln Val Val Ala Ile Ala Ser His Asp Gly Gly Lys
    275                 280                 285

Gln Ala Leu Glu Thr Val Gln Arg Leu Leu Pro Val Leu Cys Gln Asp
290                 295                 300

His Gly Leu Thr Pro Asp Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Asp His Gly Leu Thr Pro Asp Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Asp His Gly Leu Thr Pro Asp Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
                405                 410                 415

Ile Ala Ser Asn Ile Gly Gly Lys Gln Ala Leu Glu Thr Val Gln Arg
            420                 425                 430

Leu Leu Pro Val Leu Cys Gln Asp His Gly Leu Thr Pro Asp Gln Val
        435                 440                 445

Val Ala Ile Ala Ser Asn Ile Gly Gly Lys Gln Ala Leu Glu Thr Val
    450                 455                 460

Gln Arg Leu Leu Pro Val Leu Cys Gln Asp His Gly Leu Thr Pro Asp
465                 470                 475                 480

Gln Val Val Ala Ile Ala Ser His Asp Gly Gly Lys Gln Ala Leu Glu
                485                 490                 495

<210> SEQ ID NO 30
<211> LENGTH: 496
<212> TYPE: PRT
<213> ORGANISM: Artificial Sequence
<220> FEATURE:
<223> OTHER INFORMATION: Tandem repeats within the FL-63(TAL)(L) TAL DBD
      to bind to GGTATGCATAATTTG

<400> SEQUENCE: 30

Leu Thr Pro Asp Gln Val Val Ala Ile Ala Ser Asn Asn Gly Gly Lys
1               5                   10                  15

Gln Ala Leu Glu Thr Val Gln Arg Leu Leu Pro Val Leu Cys Gln Asp
            20                  25                  30

His Gly Leu Thr Pro Asp Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Asp His Gly Leu Thr Pro Asp Gln Val Val Ala Ile Ala Ser Asn
65                  70                  75                  80

Gly Gly Gly Lys Gln Ala Leu Glu Thr Val Gln Arg Leu Leu Pro Val

```
                        85                  90                  95
Leu Cys Gln Asp His Gly Leu Thr Pro Asp Gln Val Val Ala Ile Ala
                    100                 105                 110

Ser Asn Ile Gly Gly Lys Gln Ala Leu Glu Thr Val Gln Arg Leu Leu
                    115                 120                 125

Pro Val Leu Cys Gln Asp His Gly Leu Thr Pro Asp Gln Val Val Ala
                130                 135                 140

Ile Ala Ser Asn Gly Gly Gly Lys Gln Ala Leu Glu Thr Val Gln Arg
145                 150                 155                 160

Leu Leu Pro Val Leu Cys Gln Asp His Gly Leu Thr Pro Asp Gln Val
                    165                 170                 175

Val Ala Ile Ala Ser Asn Asn Gly Gly Lys Gln Ala Leu Glu Thr Val
                180                 185                 190

Gln Arg Leu Leu Pro Val Leu Cys Gln Asp His Gly Leu Thr Pro Asp
                    195                 200                 205

Gln Val Val Ala Ile Ala Ser His Asp Gly Gly Lys Gln Ala Leu Glu
                210                 215                 220

Thr Val Gln Arg Leu Leu Pro Val Leu Cys Gln Asp His Gly Leu Thr
225                 230                 235                 240

Pro Asp Gln Val Val Ala Ile Ala Ser Asn Ile Gly Gly Lys Gln Ala
                    245                 250                 255

Leu Glu Thr Val Gln Arg Leu Leu Pro Val Leu Cys Gln Asp His Gly
                260                 265                 270

Leu Thr Pro Asp Gln Val Val Ala Ile Ala Ser Asn Gly Gly Gly Lys
                275                 280                 285

Gln Ala Leu Glu Thr Val Gln Arg Leu Leu Pro Val Leu Cys Gln Asp
                290                 295                 300

His Gly Leu Thr Pro Asp Gln Val Val Ala Ile Ala Ser Asn Ile Gly
305                 310                 315                 320

Gly Lys Gln Ala Leu Glu Thr Val Gln Arg Leu Leu Pro Val Leu Cys
                    325                 330                 335

Gln Asp His Gly Leu Thr Pro Asp Gln Val Val Ala Ile Ala Ser Asn
                340                 345                 350

Ile Gly Gly Lys Gln Ala Leu Glu Thr Val Gln Arg Leu Leu Pro Val
                355                 360                 365

Leu Cys Gln Asp His Gly Leu Thr Pro Asp Gln Val Val Ala Ile Ala
                370                 375                 380

Ser Asn Gly Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
                    405                 410                 415

Ile Ala Ser Asn Gly Gly Lys Gln Ala Leu Glu Thr Val Gln Arg
                420                 425                 430

Leu Leu Pro Val Leu Cys Gln Asp His Gly Leu Thr Pro Asp Gln Val
                    435                 440                 445

Val Ala Ile Ala Ser Asn Gly Gly Lys Gln Ala Leu Glu Thr Val
                450                 455                 460

Gln Arg Leu Leu Pro Val Leu Cys Gln Asp His Gly Leu Thr Pro Asp
465                 470                 475                 480

Gln Val Val Ala Ile Ala Ser Asn Asn Gly Gly Lys Gln Ala Leu Glu
                    485                 490                 495

<210> SEQ ID NO 31
```

<211> LENGTH: 496
<212> TYPE: PRT
<213> ORGANISM: Artificial Sequence
<220> FEATURE:
<223> OTHER INFORMATION: Tandem repeats within the FL-63_TAL(R) TAL DBD to bind to CCACATGGGTATGGG

<400> SEQUENCE: 31

```
Leu Thr Pro Asp Gln Val Val Ala Ile Ala Ser His Asp Gly Gly Lys
1               5                   10                  15
Gln Ala Leu Glu Thr Val Gln Arg Leu Leu Pro Val Leu Cys Gln Asp
            20                  25                  30
His Gly Leu Thr Pro Asp Gln Val Val Ala Ile Ala Ser His Asp Gly
        35                  40                  45
Gly Lys Gln Ala Leu Glu Thr Val Gln Arg Leu Leu Pro Val Leu Cys
    50                  55                  60
Gln Asp His Gly Leu Thr Pro Asp Gln Val Val Ala Ile Ala Ser Asn
65                  70                  75                  80
Ile Gly Gly Lys Gln Ala Leu Glu Thr Val Gln Arg Leu Leu Pro Val
                85                  90                  95
Leu Cys Gln Asp His Gly Leu Thr Pro Asp Gln Val Val Ala Ile Ala
            100                 105                 110
Ser His Asp Gly Gly Lys Gln Ala Leu Glu Thr Val Gln Arg Leu Leu
        115                 120                 125
Pro Val Leu Cys Gln Asp His Gly Leu Thr Pro Asp Gln Val Val Ala
    130                 135                 140
Ile Ala Ser Asn Ile Gly Gly Lys Gln Ala Leu Glu Thr Val Gln Arg
145                 150                 155                 160
Leu Leu Pro Val Leu Cys Gln Asp His Gly Leu Thr Pro Asp Gln Val
                165                 170                 175
Val Ala Ile Ala Ser Asn Gly Gly Lys Gln Ala Leu Glu Thr Val
            180                 185                 190
Gln Arg Leu Leu Pro Val Leu Cys Gln Asp His Gly Leu Thr Pro Asp
        195                 200                 205
Gln Val Val Ala Ile Ala Ser Asn Asn Gly Gly Lys Gln Ala Leu Glu
    210                 215                 220
Thr Val Gln Arg Leu Leu Pro Val Leu Cys Gln Asp His Gly Leu Thr
225                 230                 235                 240
Pro Asp Gln Val Val Ala Ile Ala Ser Asn Asn Gly Gly Lys Gln Ala
                245                 250                 255
Leu Glu Thr Val Gln Arg Leu Leu Pro Val Leu Cys Gln Asp His Gly
            260                 265                 270
Leu Thr Pro Asp Gln Val Val Ala Ile Ala Ser Asn Asn Gly Gly Lys
        275                 280                 285
Gln Ala Leu Glu Thr Val Gln Arg Leu Leu Pro Val Leu Cys Gln Asp
    290                 295                 300
His Gly Leu Thr Pro Asp Gln Val Val Ala Ile Ala Ser Asn Gly Gly
305                 310                 315                 320
Gly Lys Gln Ala Leu Glu Thr Val Gln Arg Leu Leu Pro Val Leu Cys
                325                 330                 335
Gln Asp His Gly Leu Thr Pro Asp Gln Val Val Ala Ile Ala Ser Asn
            340                 345                 350
Ile Gly Gly Lys Gln Ala Leu Glu Thr Val Gln Arg Leu Leu Pro Val
        355                 360                 365
Leu Cys Gln Asp His Gly Leu Thr Pro Asp Gln Val Val Ala Ile Ala
```

```
                370               375               380
Ser Asn Gly Gly Gly Lys Gln Ala Leu Glu Thr Val Gln Arg Leu Leu
385                 390               395                 400

Pro Val Leu Cys Gln Asp His Gly Leu Thr Pro Asp Gln Val Val Ala
                405               410               415

Ile Ala Ser Asn Asn Gly Gly Lys Gln Ala Leu Glu Thr Val Gln Arg
                420               425               430

Leu Leu Pro Val Leu Cys Gln Asp His Gly Leu Thr Pro Asp Gln Val
                435               440               445

Val Ala Ile Ala Ser Asn Asn Gly Gly Lys Gln Ala Leu Glu Thr Val
                450               455               460

Gln Arg Leu Leu Pro Val Leu Cys Gln Asp His Gly Leu Thr Pro Asp
465                 470               475               480

Gln Val Val Ala Ile Ala Ser Asn Asn Gly Gly Lys Gln Ala Leu Glu
                485               490               495

<210> SEQ ID NO 32
<211> LENGTH: 802
<212> TYPE: PRT
<213> ORGANISM: Artificial Sequence
<220> FEATURE:
<223> OTHER INFORMATION: Tandem repeats within the FL-71_TAL(L) TAL DBD
      to bind to GTGTAAAGTTTTTTTTTAAGTTAC

<400> SEQUENCE: 32

Leu Thr Pro Asp Gln Val Val Ala Ile Ala Ser Asn Asn Gly Gly Lys
1                   5                  10                  15

Gln Ala Leu Glu Thr Val Gln Arg Leu Leu Pro Val Leu Cys Gln Asp
                20                  25                  30

His Gly Leu Thr Pro Asp Gln Val Val Ala Ile Ala Ser Asn Gly Gly
            35                  40                  45

Gly Lys Gln Ala Leu Glu Thr Val Gln Arg Leu Leu Pro Val Leu Cys
        50                  55                  60

Gln Asp His Gly Leu Thr Pro Asp Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Asp His Gly Leu Thr Pro Asp Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Asp His Gly Leu Thr Pro Asp Gln Val Val Ala
    130                 135                 140

Ile Ala Ser Asn Ile Gly Gly Lys Gln Ala Leu Glu Thr Val Gln Arg
145                 150                 155                 160

Leu Leu Pro Val Leu Cys Gln Asp His Gly Leu Thr Pro Asp Gln Val
                165                 170                 175

Val Ala Ile Ala Ser Asn Ile Gly Gly Lys Gln Ala Leu Glu Thr Val
            180                 185                 190

Gln Arg Leu Leu Pro Val Leu Cys Gln Asp His Gly Leu Thr Pro Asp
        195                 200                 205

Gln Val Val Ala Ile Ala Ser Asn Ile Gly Gly Lys Gln Ala Leu Glu
    210                 215                 220

Thr Val Gln Arg Leu Leu Pro Val Leu Cys Gln Asp His Gly Leu Thr
225                 230                 235                 240
```

```
Pro Asp Gln Val Val Ala Ile Ala Ser Asn Gly Gly Lys Gln Ala
            245                 250                 255

Leu Glu Thr Val Gln Arg Leu Leu Pro Val Leu Cys Gln Asp His Gly
        260                 265                 270

Leu Thr Pro Asp Gln Val Val Ala Ile Ala Ser Asn Gly Gly Gly Lys
    275                 280                 285

Gln Ala Leu Glu Thr Val Gln Arg Leu Leu Pro Val Leu Cys Gln Asp
290                 295                 300

His Gly Leu Thr Pro Asp Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Asp His Gly Leu Thr Pro Asp Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Asp His Gly Leu Thr Pro Asp Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Asp His Gly Leu Thr Pro Asp Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Asp His Gly Leu Thr Pro Asp
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Asp His Gly Leu Thr
            500                 505                 510

Pro Asp Gln Val Val Ala Ile Ala Ser Asn Gly Gly Gly Lys Gln Ala
        515                 520                 525

Leu Glu Thr Val Gln Arg Leu Leu Pro Val Leu Cys Gln Asp His Gly
    530                 535                 540

Leu Thr Pro Asp Gln Val Val Ala Ile Ala Ser Asn Gly Gly Gly Lys
545                 550                 555                 560

Gln Ala Leu Glu Thr Val Gln Arg Leu Leu Pro Val Leu Cys Gln Asp
                565                 570                 575

His Gly Leu Thr Pro Asp Gln Val Val Ala Ile Ala Ser Asn Ile Gly
            580                 585                 590

Gly Lys Gln Ala Leu Glu Thr Val Gln Arg Leu Leu Pro Val Leu Cys
        595                 600                 605

Gln Asp His Gly Leu Thr Pro Asp Gln Val Val Ala Ile Ala Ser Asn
    610                 615                 620

Ile Gly Gly Lys Gln Ala Leu Glu Thr Val Gln Arg Leu Leu Pro Val
625                 630                 635                 640

Leu Cys Gln Asp His Gly Leu Thr Pro Asp Gln Val Val Ala Ile Ala
                645                 650                 655

Ser Asn Asn Gly Gly Lys Gln Ala Leu Glu Thr Val Gln Arg Leu Leu
```

```
                        660                 665                 670
Pro Val Leu Cys Gln Asp His Gly Leu Thr Pro Asp Gln Val Val Ala
                675                 680                 685

Ile Ala Ser Asn Gly Gly Gly Lys Gln Ala Leu Glu Thr Val Gln Arg
            690                 695                 700

Leu Leu Pro Val Leu Cys Gln Asp His Gly Leu Thr Pro Asp Gln Val
705                 710                 715                 720

Val Ala Ile Ala Ser Asn Gly Gly Gly Lys Gln Ala Leu Glu Thr Val
                725                 730                 735

Gln Arg Leu Leu Pro Val Leu Cys Gln Asp His Gly Leu Thr Pro Asp
            740                 745                 750

Gln Val Val Ala Ile Ala Ser Asn Ile Gly Gly Lys Gln Ala Leu Glu
        755                 760                 765

Thr Val Gln Arg Leu Leu Pro Val Leu Cys Gln Asp His Gly Leu Thr
770                 775                 780

Pro Asp Gln Val Val Ala Ile Ala Ser His Asp Gly Gly Lys Gln Ala
785                 790                 795                 800

Leu Glu

<210> SEQ ID NO 33
<211> LENGTH: 496
<212> TYPE: PRT
<213> ORGANISM: Artificial Sequence
<220> FEATURE:
<223> OTHER INFORMATION: Tandem repeats within the FL71_TAL(R) TAL DBD
      to bind to GCATATTCATAATCT

<400> SEQUENCE: 33

Leu Thr Pro Asp Gln Val Val Ala Ile Ala Ser Asn Asn Gly Gly Lys
1               5                   10                  15

Gln Ala Leu Glu Thr Val Gln Arg Leu Leu Pro Val Leu Cys Gln Asp
            20                  25                  30

His Gly Leu Thr Pro Asp Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Asp His Gly Leu Thr Pro Asp Gln Val Val Ala Ile Ala Ser Asn
65                  70                  75                  80

Ile Gly Gly Lys Gln Ala Leu Glu Thr Val Gln Arg Leu Leu Pro Val
                85                  90                  95

Leu Cys Gln Asp His Gly Leu Thr Pro Asp Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Asp His Gly Leu Thr Pro Asp Gln Val Val Ala
    130                 135                 140

Ile Ala Ser Asn Ile Gly Gly Lys Gln Ala Leu Glu Thr Val Gln Arg
145                 150                 155                 160

Leu Leu Pro Val Leu Cys Gln Asp His Gly Leu Thr Pro Asp Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Asp His Gly Leu Thr Pro Asp
        195                 200                 205

Gln Val Val Ala Ile Ala Ser Asn Gly Gly Gly Lys Gln Ala Leu Glu
```

```
            210                 215                 220
Thr Val Gln Arg Leu Leu Pro Val Leu Cys Gln Asp His Gly Leu Thr
225                 230                 235                 240

Pro Asp Gln Val Val Ala Ile Ala Ser His Asp Gly Gly Lys Gln Ala
            245                 250                 255

Leu Glu Thr Val Gln Arg Leu Leu Pro Val Leu Cys Gln Asp His Gly
            260                 265                 270

Leu Thr Pro Asp Gln Val Val Ala Ile Ala Ser Asn Ile Gly Gly Lys
        275                 280                 285

Gln Ala Leu Glu Thr Val Gln Arg Leu Leu Pro Val Leu Cys Gln Asp
    290                 295                 300

His Gly Leu Thr Pro Asp Gln Val Val Ala Ile Ala Ser Asn Gly Gly
305                 310                 315                 320

Gly Lys Gln Ala Leu Glu Thr Val Gln Arg Leu Leu Pro Val Leu Cys
            325                 330                 335

Gln Asp His Gly Leu Thr Pro Asp Gln Val Val Ala Ile Ala Ser Asn
        340                 345                 350

Ile Gly Gly Lys Gln Ala Leu Glu Thr Val Gln Arg Leu Leu Pro Val
    355                 360                 365

Leu Cys Gln Asp His Gly Leu Thr Pro Asp Gln Val Val Ala Ile Ala
370                 375                 380

Ser Asn Ile Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
            405                 410                 415

Ile Ala Ser Asn Gly Gly Gly Lys Gln Ala Leu Glu Thr Val Gln Arg
        420                 425                 430

Leu Leu Pro Val Leu Cys Gln Asp His Gly Leu Thr Pro Asp Gln Val
    435                 440                 445

Val Ala Ile Ala Ser His Asp Gly Gly Lys Gln Ala Leu Glu Thr Val
        450                 455                 460

Gln Arg Leu Leu Pro Val Leu Cys Gln Asp His Gly Leu Thr Pro Asp
465                 470                 475                 480

Gln Val Val Ala Ile Ala Ser Asn Gly Gly Gly Lys Gln Ala Leu Glu
            485                 490                 495
```

<210> SEQ ID NO 34
<211> LENGTH: 191
<212> TYPE: DNA
<213> ORGANISM: Artificial Sequence
<220> FEATURE:
<223> OTHER INFORMATION: Outer FRT; the EM-7 promoter is located before the recombination site.

<400> SEQUENCE: 34
catcggcata gtatatcggc atagtataat acgacaaggt gaggaactaa acccctattc      60
ttgtgttcac gactgacatc accgtgaagt tcctatactg ataatagaaa tggcattgtc     120
actttcttcc ctactgcaac agaagcccag ctcttccctt tgaaaaacac gatgataata     180
tggccacaac c                                                         191

<210> SEQ ID NO 35
<211> LENGTH: 180
<212> TYPE: DNA
<213> ORGANISM: Artificial Sequence
<220> FEATURE:
<223> OTHER INFORMATION: Outer FRT; the EM-7 promoter is located before the recombination site.

<400> SEQUENCE: 35

```
catcggcata gtatatcggc atagtataat acgacaaggt gaggaactaa accacaactc    60
aaattatgca taccagctct gaagttccta tactgcactt agaataatcc ttttgtctct   120
ccacatgggt atgggagagg ccttcccttt gaaaaacacg atgataatat ggccacaacc   180
```

<210> SEQ ID NO 36
<211> LENGTH: 201
<212> TYPE: DNA
<213> ORGANISM: Artificial Sequence
<220> FEATURE:
<223> OTHER INFORMATION: Outer FRT site; the lacIQ promoter is located
      before the recombination site.

<400> SEQUENCE: 36

```
gactcactat agggagaccc aagctggcta ggtggtgcaa aacctttcgc ggtatggcat    60
gatagcgccc ggaagagagt caattcaggg agatacatta agtaacttaa aaaaaaactt   120
tacacagtct gcctagtaca ttactatttg gagtatagga acttctattt gcatattcat   180
aatctcccta ctttatttc t                                              201
```

<210> SEQ ID NO 37
<211> LENGTH: 1277
<212> TYPE: PRT
<213> ORGANISM: Artificial Sequence
<220> FEATURE:
<223> OTHER INFORMATION: 71-18_TLA is an aa sequence of a representative
      chimeric Fl-TAL recombinase.

<400> SEQUENCE: 37

```
Met Ser Gln Phe Asp Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
                20                  25                  30

Ser Cys Thr Ala Glu Leu Thr Tyr Leu Cys Trp Val Thr His Asn
            35                  40                  45

Gly Ala Ala Ile Lys Arg Ser Thr Phe Val Asn Tyr Asn Ser Ile Ile
        50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Asn Gly Gln Lys His
                100                 105                 110

Gln Pro Asp Ile Thr Asp Ile Val Ser Ser Leu Gln Leu Gln Phe Glu
            115                 120                 125

Ser Pro Glu Glu Ala Asp Lys Gly Asn Ser His Ser Lys Lys Met Leu
        130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Ser Thr Lys Thr Lys Ala
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205
```

```
Lys Tyr Leu Gly Glu Ile Ile Gln Cys Leu Val Thr Glu Thr Lys Thr
    210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Asn Lys Gln Glu Tyr
            260                 265                 270

Gln Leu Leu Lys Asp Asn Leu Val Arg Ser Tyr Asn Lys Ala Leu Lys
            275                 280                 285

Lys Ser Ala Pro Tyr Pro Phe Phe Ala Ile Lys Asn Gly Pro Lys Ser
290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
            340                 345                 350

His Tyr Phe Ala Leu Val Ser Arg Tyr Tyr Glu Tyr Asp Pro Ile Ser
            355                 360                 365

Lys Glu Met Ile Ala Leu Lys Asp Glu Thr Asn Pro Ile Glu Glu Trp
    370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile Gly Thr Gly Ser Gly Gly Ser Gly Gly
            420                 425                 430

Ser Gly Gly Ser Gly Thr Ser Val Asp Leu Arg Thr Leu Gly Tyr Ser
        435                 440                 445

Gln Gln Gln Gln Glu Lys Ile Lys Pro Lys Val Arg Ser Thr Val Ala
    450                 455                 460

Gln His His Glu Ala Leu Val Gly His Gly Phe Thr His Ala His Ile
465                 470                 475                 480

Val Ala Leu Ser Gln His Pro Ala Ala Leu Gly Thr Val Ala Val Thr
                485                 490                 495

Tyr Gln His Ile Ile Thr Ala Leu Pro Glu Ala Thr His Glu Asp Ile
            500                 505                 510

Val Gly Val Gly Lys Gln Trp Ser Gly Ala Arg Ala Leu Glu Ala Leu
    515                 520                 525

Leu Thr Asp Ala Gly Glu Leu Arg Gly Pro Pro Leu Gln Leu Asp Thr
530                 535                 540

Gly Gln Leu Val Lys Ile Ala Lys Arg Gly Gly Val Thr Ala Met Glu
545                 550                 555                 560

Ala Val His Ala Ser Arg Asn Ala Leu Thr Gly Ala Pro Leu Asn Leu
                565                 570                 575

Thr Pro Asp Gln Val Val Ala Ile Ala Ser Asn Asn Gly Gly Lys Gln
            580                 585                 590

Ala Leu Glu Thr Val Gln Arg Leu Leu Pro Val Leu Cys Gln Asp His
            595                 600                 605

Gly Leu Thr Pro Asp Gln Val Val Ala Ile Ala Ser His Asp Gly Gly
    610                 615                 620

Lys Gln Ala Leu Glu Thr Val Gln Arg Leu Leu Pro Val Leu Cys Gln
```

-continued

```
            625                 630                 635                 640
Asp His Gly Leu Thr Pro Asp Gln Val Val Ala Ile Ala Ser Asn Ile
                    645                 650                 655
Gly Gly Lys Gln Ala Leu Glu Thr Val Gln Arg Leu Leu Pro Val Leu
                    660                 665                 670
Cys Gln Asp His Gly Leu Thr Pro Asp Gln Val Val Ala Ile Ala Ser
                    675                 680                 685
Asn Gly Gly Gly Lys Gln Ala Leu Glu Thr Val Gln Arg Leu Leu Pro
                    690                 695                 700
Val Leu Cys Gln Asp His Gly Leu Thr Pro Asp Gln Val Val Ala Ile
705                 710                 715                 720
Ala Ser Asn Ile Gly Gly Lys Gln Ala Leu Glu Thr Val Gln Arg Leu
                    725                 730                 735
Leu Pro Val Leu Cys Gln Asp His Gly Leu Thr Pro Asp Gln Val Val
                    740                 745                 750
Ala Ile Ala Ser Asn Gly Gly Gly Lys Gln Ala Leu Glu Thr Val Gln
                    755                 760                 765
Arg Leu Leu Pro Val Leu Cys Gln Asp His Gly Leu Thr Pro Asp Gln
                    770                 775                 780
Val Val Ala Ile Ala Ser Asn Gly Gly Gly Lys Gln Ala Leu Glu Thr
785                 790                 795                 800
Val Gln Arg Leu Leu Pro Val Leu Cys Gln Asp His Gly Leu Thr Pro
                    805                 810                 815
Asp Gln Val Val Ala Ile Ala Ser His Asp Gly Gly Lys Gln Ala Leu
                    820                 825                 830
Glu Thr Val Gln Arg Leu Leu Pro Val Leu Cys Gln Asp His Gly Leu
                    835                 840                 845
Thr Pro Asp Gln Val Val Ala Ile Ala Ser Asn Ile Gly Gly Lys Gln
                    850                 855                 860
Ala Leu Glu Thr Val Gln Arg Leu Leu Pro Val Leu Cys Gln Asp His
865                 870                 875                 880
Gly Leu Thr Pro Asp Gln Val Val Ala Ile Ala Ser Asn Gly Gly Gly
                    885                 890                 895
Lys Gln Ala Leu Glu Thr Val Gln Arg Leu Leu Pro Val Leu Cys Gln
                    900                 905                 910
Asp His Gly Leu Thr Pro Asp Gln Val Val Ala Ile Ala Ser Asn Ile
                    915                 920                 925
Gly Gly Lys Gln Ala Leu Glu Thr Val Gln Arg Leu Leu Pro Val Leu
                    930                 935                 940
Cys Gln Asp His Gly Leu Thr Pro Asp Gln Val Val Ala Ile Ala Ser
945                 950                 955                 960
Asn Ile Gly Gly Lys Gln Ala Leu Glu Thr Val Gln Arg Leu Leu Pro
                    965                 970                 975
Val Leu Cys Gln Asp His Gly Leu Thr Pro Asp Gln Val Val Ala Ile
                    980                 985                 990
Ala Ser Asn Gly Gly Gly Lys Gln Ala Leu Glu Thr Val Gln Arg Leu
                    995                1000                1005
Leu Pro Val Leu Cys Gln Asp His Gly Leu Thr Pro Asp Gln Val
                   1010                1015                1020
Val Ala Ile Ala Ser His Asp Gly Gly Lys Gln Ala Leu Glu Thr
                   1025                1030                1035
Val Gln Arg Leu Leu Pro Val Leu Cys Gln Asp His Gly Leu Thr
                   1040                1045                1050
```

Pro Asp Gln Val Val Ala Ile Ala Ser Asn Gly Gly Gly Lys Gln
    1055                1060                1065

Ala Leu Glu Thr Val Gln Arg Leu Leu Pro Val Leu Cys Gln Asp
    1070                1075                1080

His Gly Leu Thr Pro Asp Gln Val Val Ala Ile Ala Ser His Asp
    1085                1090                1095

Gly Gly Lys Gln Ala Leu Glu Thr Val Gln Arg Leu Leu Pro Val
    1100                1105                1110

Leu Cys Gln Asp His Gly Leu Thr Pro Asp Gln Val Val Ala Ile
    1115                1120                1125

Ala Ser His Asp Gly Gly Lys Gln Ala Leu Glu Thr Val Gln Arg
    1130                1135                1140

Leu Leu Pro Val Leu Cys Gln Asp His Gly Leu Thr Pro Asp Gln
    1145                1150                1155

Val Val Ala Ile Ala Ser His Asp Gly Gly Lys Gln Ala Leu Glu
    1160                1165                1170

Ser Ile Val Ala Gln Leu Ser Arg Pro Asp Pro Ala Leu Ala Ala
    1175                1180                1185

Leu Thr Asn Asp His Leu Val Ala Leu Ala Cys Leu Gly Gly Arg
    1190                1195                1200

Pro Ala Met Asp Ala Val Lys Lys Gly Leu Pro His Ala Pro Glu
    1205                1210                1215

Leu Ile Arg Arg Val Asn Arg Arg Ile Gly Glu Arg Thr Ser His
    1220                1225                1230

Arg Val Ala Asp Tyr Ala Gln Val Val Arg Val Leu Glu Phe Phe
    1235                1240                1245

Gln Cys His Ser His Pro Ala Tyr Ala Phe Asp Glu Ala Met Thr
    1250                1255                1260

Gln Phe Gly Met Ser Gly Pro Pro Lys Lys Lys Arg Lys Val
    1265                1270                1275

<210> SEQ ID NO 38
<211> LENGTH: 1056
<212> TYPE: DNA
<213> ORGANISM: Artificial Sequence
<220> FEATURE:
<223> OTHER INFORMATION: Coding sequence of iCreM24.

<400> SEQUENCE: 38
atggtgccca agaagaagag gaaagtctcc aacctgctga ctgtgcacca aaacctgcct      60
gccctccctg tggatgccac ctctgatgaa gtcatgaaga acctgatgga catgttcagg     120
gacaggcagg ccttctctga acacacctgg aagatgctcc tgtctgtgtg cagatccctgg    180 gctgcctggt gcaagctgaa caacaggaaa tggttccctg ctgaacctga ggatgtgagg     240
gactacctcc tgtacctgca agccagaggc ctggctgtga agaccatcca acagcacctg     300
ggccagctca acatgctgca caggagatct ggcctgcctc gcccttctga ctccaatgct     360
gtgtccctgg tgatgaggag aatcagaaag gagaatgtgg atgctgggga gagagccaag     420
caggccctgg cctttgaacg cactgacttt gaccaagtca gatccctgat ggagaactct     480
gacagatgcc aggacatcag gaacctggcc ttcctgggca ttgcctacaa caccctgctg     540
cgcattgccg aaattgccag aatcagagtg aaggacatct cccgcaccga tggtgggaga     600
atgctgatcc acattggcag gaccaagacc ctggtgtcca cagctggtgt ggagaaggcc     660
ctgtccctgg gggttaccaa gctggtggag agatggatct ctgtgtctgg tgtggctgat     720

```
gaccccaaca actacctgtt ctgccgggtc agaaagaatg gtgtggctgc cccttctgcc      780
acctcccaac tgtccacccg ggccctggaa gggatcttcg aggccaccca ccgcctgatc      840
tatggtgcca aggatgactc tgggcagaga tacctggcct ggtctggcca ctctgccaga      900
gtgggtgctg ccaggacat ggccagggct ggtgtgtcca tccctgaaat catgcaggct       960
ggtggctgga ccaatgtgaa cattgtgatg aactacatca gaaacctgga ctctgagact      1020
ggggccatgg tgaggctgct cgaggatggg gactga                                1056
```

<210> SEQ ID NO 39
<211> LENGTH: 351
<212> TYPE: PRT
<213> ORGANISM: Artificial Sequence
<220> FEATURE:
<223> OTHER INFORMATION: aa sequence of iCreM24.

<400> SEQUENCE: 39

```
Met Val Pro Lys Lys Arg Lys Val Ser Asn Leu Leu Thr Val His
1               5                   10                  15

Gln Asn Leu Pro Ala Leu Pro Val Asp Ala Thr Ser Asp Glu Val Met
                20                  25                  30

Lys Asn Leu Met Asp Met Phe Arg Asp Arg Gln Ala Phe Ser Glu His
            35                  40                  45

Thr Trp Lys Met Leu Leu Ser Val Cys Arg Ser Trp Ala Ala Trp Cys
    50                  55                  60

Lys Leu Asn Asn Arg Lys Trp Phe Pro Ala Glu Pro Glu Asp Val Arg
65                  70                  75                  80

Asp Tyr Leu Leu Tyr Leu Gln Ala Arg Gly Leu Ala Val Lys Thr Ile
                85                  90                  95

Gln Gln His Leu Gly Gln Leu Asn Met Leu His Arg Arg Ser Gly Leu
            100                 105                 110

Pro Arg Pro Ser Asp Ser Asn Ala Val Ser Leu Val Met Arg Arg Ile
        115                 120                 125

Arg Lys Glu Asn Val Asp Ala Gly Glu Arg Ala Lys Gln Ala Leu Ala
    130                 135                 140

Phe Glu Arg Thr Asp Phe Asp Gln Val Arg Ser Leu Met Glu Asn Ser
145                 150                 155                 160

Asp Arg Cys Gln Asp Ile Arg Asn Leu Ala Phe Leu Gly Ile Ala Tyr
                165                 170                 175

Asn Thr Leu Leu Arg Ile Ala Glu Ile Ala Arg Ile Arg Val Lys Asp
            180                 185                 190

Ile Ser Arg Thr Asp Gly Gly Arg Met Leu Ile His Ile Gly Arg Thr
        195                 200                 205

Lys Thr Leu Val Ser Thr Ala Gly Val Glu Lys Ala Leu Ser Leu Gly
    210                 215                 220

Val Thr Lys Leu Val Glu Arg Trp Ile Ser Val Ser Gly Val Ala Asp
225                 230                 235                 240

Asp Pro Asn Asn Tyr Leu Phe Cys Arg Val Arg Lys Asn Gly Val Ala
                245                 250                 255

Ala Pro Ser Ala Thr Ser Gln Leu Ser Thr Arg Ala Leu Glu Gly Ile
            260                 265                 270

Phe Glu Ala Thr His Arg Leu Ile Tyr Gly Ala Lys Asp Asp Ser Gly
        275                 280                 285

Gln Arg Tyr Leu Ala Trp Ser Gly His Ser Ala Arg Val Gly Ala Ala
    290                 295                 300
```

Arg Asp Met Ala Arg Ala Gly Val Ser Ile Pro Glu Ile Met Gln Ala
305                 310                 315                 320

Gly Gly Trp Thr Asn Val Asn Ile Val Met Asn Tyr Ile Arg Asn Leu
                325                 330                 335

Asp Ser Glu Thr Gly Ala Met Val Arg Leu Leu Glu Asp Gly Asp
                340                 345                 350

<210> SEQ ID NO 40
<211> LENGTH: 1385
<212> TYPE: DNA
<213> ORGANISM: Artificial Sequence
<220> FEATURE:
<223> OTHER INFORMATION: iCreM24-TAL partial coding sequence

<400> SEQUENCE: 40

```
atggtgccca agaagaagag gaaagtctcc aacctgctga ctgtgcacca aaacctgcct      60
gccctccctg tggatgccac ctctgatgaa gtcatgaaga acctgatgga catgttcagg     120
gacaggcagg ccttctctga acacacctgg aagatgctcc tgtctgtgtg cagatcctgg     180
gctgcctggt gcaagctgaa caacaggaaa tggttccctg ctgaacctga ggatgtgagg     240
gactacctcc tgtacctgca agccagaggc ctggctgtga agaccatcca acagcacctg     300
ggccagctca acatgctgca caggagatct ggcctgcctc gcccttctga ctccaatgct     360
gtgtccctgg tgatgaggag aatcagaaag agaatgtgg atgctgggga gagagccaag     420
caggccctgg cctttgaacg cactgacttt gaccaagtca gatccctgat ggagaactct     480
gacagatgcc aggacatcag gaacctggcc ttcctgggca ttgcctacaa caccctgctg     540
cgcattgccg aaattgccag aatcagagtg aaggacatct cccgcaccga tggtgggaga     600
atgctgatcc acattggcag gaccaagacc ctggtgtcca gctggtgt ggagaaggcc       660 ctgtccctgg gggttaccaa gctggtggag agatggatct ctgtgtctgg tgtggctgat     720
gaccccaaca actacctgtt ctgccgggtc agaaagaatg gtgtggctgc cccttctgcc     780
acctcccaac tgtccaccccg ggccctggaa gggatcttcg aggccaccca ccgcctgatc     840
tatggtgcca aggatgactc tgggcagaga tacctggcct ggtctggcca ctctgccaga     900
gtgggtgctg ccagggacat ggccagggct ggtgtgtcca tccctgaaat catgcaggct     960
ggtggctgga ccaatgtgaa cattgtgatg aactacatca gaaacctgga ctctgagact    1020
ggggccatgg tgaggctgct cgaggatggg gacggtaccg gatcaggcgg aagcggaccg    1080
catacagcgg ctgccccagc agagtgggat gaggcgcaat cggctctgcg tgcagccgat    1140
gacccgccac ccaccgtgcg tgtcgctgtc actgccgcgc ggccgccgcg cgccaagccg    1200
gccccgcgac ggcgtgctgc gcaaccctcc gacgcttcgc cggccgcgca ggtggatcta    1260
cgcacgctcg gctacagtca gcagcagcaa gagaagatca aaccgaaagg tgcgttcgac    1320
agtggcgcag caccacgagg cactggtggg ccatgggttt acacacgcgc acatcgttgc    1380
gctca                                                               1385
```

<210> SEQ ID NO 41
<211> LENGTH: 71
<212> TYPE: DNA
<213> ORGANISM: Artificial Sequence
<220> FEATURE:
<223> OTHER INFORMATION: loxP-like sequence 69058 (LL-69) with flanking
      sequences for TAL binding

<400> SEQUENCE: 41

-continued

```
aaataagaaa tttgtaaatt tccttctgat aactagaaat agaggatcca gtttcttttg    60
gttaacctaa a                                                         71

<210> SEQ ID NO 42
<211> LENGTH: 80
<212> TYPE: DNA
<213> ORGANISM: Artificial Sequence
<220> FEATURE:
<223> OTHER INFORMATION: loxP-like sequence 69058 (LL-69) with flanking
      sequences for TAL binding

<400> SEQUENCE: 42
caatggaaat aagaaatttg taaatttcct tctgataact agaaatagag gatccagttt    60
cttttggtta acctaaattt                                                80

<210> SEQ ID NO 43
<211> LENGTH: 77
<212> TYPE: DNA
<213> ORGANISM: Artificial Sequence
<220> FEATURE:
<223> OTHER INFORMATION: loxP-like sequence 69058 (LL-69) with flanking
      sequences for TAL binding

<400> SEQUENCE: 43
caatggaaat aagaaatttg taaatttcct tctgataact agaaatagag gatccagttt    60
cttttggtta acctaaa                                                   77

<210> SEQ ID NO 44
<211> LENGTH: 78
<212> TYPE: DNA
<213> ORGANISM: Artificial Sequence
<220> FEATURE:
<223> OTHER INFORMATION: FL-71, left TAL sequences of different lengths
      (TAL/L18-TAL/R15)

<400> SEQUENCE: 44
taaaaaaaaa ctttacacag tctgcctagt acattactat ttggagtata ggaacttcta    60
tttgcatatt cataatct                                                  78

<210> SEQ ID NO 45
<211> LENGTH: 75
<212> TYPE: DNA
<213> ORGANISM: Artificial Sequence
<220> FEATURE:
<223> OTHER INFORMATION: FL-71, left TAL seqences of different lengths
      (TAL/L15-TAL/R15)

<400> SEQUENCE: 45
aaaaaaactt tacacagtct gcctagtaca ttactatttg gagtatagga acttctattt    60
gcatattcat aatct                                                     75

<210> SEQ ID NO 46
<211> LENGTH: 34
<212> TYPE: DNA
<213> ORGANISM: Artificial Sequence
<220> FEATURE:
<223> OTHER INFORMATION: Lox-like sequence 69058 (LL-69)

<400> SEQUENCE: 46
tttccttctg ataactagaa atagaggatc cagt                                34

<210> SEQ ID NO 47
<211> LENGTH: 34
```

```
<212> TYPE: DNA
<213> ORGANISM: Artificial Sequence
<220> FEATURE:
<223> OTHER INFORMATION: Consensus FRT sequence

<400> SEQUENCE: 47
gaagttccta twctttctag agwataggaa cttc                               34

<210> SEQ ID NO 48
<211> LENGTH: 46
<212> TYPE: DNA
<213> ORGANISM: Artificial Sequence
<220> FEATURE:
<223> OTHER INFORMATION: Sequencing of integration-specific PCR product
      LJ of pTarget integrated into FL-61

<400> SEQUENCE: 48
caccgtcatg gtccaagtct gataatagaa atggcattgt cacttt                  46

<210> SEQ ID NO 49
<211> LENGTH: 46
<212> TYPE: DNA
<213> ORGANISM: Artificial Sequence
<220> FEATURE:
<223> OTHER INFORMATION: Sequencing of integration-specific PCR product
      RJ of pTarget integrated into FL-61

<400> SEQUENCE: 49
caccgtgaag ttcctatact gataatagaa atggcattgt cacttt                  46

<210> SEQ ID NO 50
<211> LENGTH: 46
<212> TYPE: DNA
<213> ORGANISM: Artificial Sequence
<220> FEATURE:
<223> OTHER INFORMATION: Sequencing of integration-specific PCR product
      LJ of pTarget integrated into FL-63

<400> SEQUENCE: 50
agctctcacc tgctaattct gcacttagaa taatccttt gtctct                   46

<210> SEQ ID NO 51
<211> LENGTH: 46
<212> TYPE: DNA
<213> ORGANISM: Artificial Sequence
<220> FEATURE:
<223> OTHER INFORMATION: Sequencing of integration-specific PCR product
      RJ of pTarget integrated into FL-63

<400> SEQUENCE: 51
agctctgaag ttcctatact gcacttagaa taatccttt gtctct                   46

<210> SEQ ID NO 52
<211> LENGTH: 46
<212> TYPE: DNA
<213> ORGANISM: Artificial Sequence
<220> FEATURE:
<223> OTHER INFORMATION: Sequencing of integration-specific PCR product
      LJ of pTarget integrated into FL-71

<400> SEQUENCE: 52
agtctgccta gtacattact atttggagta taggaacttc tatttg                  46

<210> SEQ ID NO 53
<211> LENGTH: 46
<212> TYPE: DNA
<213> ORGANISM: Artificial Sequence
```

```
<220> FEATURE:
<223> OTHER INFORMATION: Sequencing of integration-specific PCR product
      RJ of pTarget integrated into FL-71

<400> SEQUENCE: 53
agtctgccta gtacattact atttggaata tatgtgtgct tatttg                       46

<210> SEQ ID NO 54
<211> LENGTH: 37
<212> TYPE: DNA
<213> ORGANISM: Artificial Sequence
<220> FEATURE:
<223> OTHER INFORMATION: Genome scanner sequence file

<400> SEQUENCE: 54
gatgcattcc tgttttgtaa tgattttcgg aaatttc                                 37

<210> SEQ ID NO 55
<211> LENGTH: 37
<212> TYPE: DNA
<213> ORGANISM: Artificial Sequence
<220> FEATURE:
<223> OTHER INFORMATION: Genome Scanner sequence

<400> SEQUENCE: 55
atgcattcct gttttgtaat gattttcgga aatttcg                                 37

<210> SEQ ID NO 56
<211> LENGTH: 37
<212> TYPE: DNA
<213> ORGANISM: Artificial Sequence
<220> FEATURE:
<223> OTHER INFORMATION: Genome Scanner sequence

<400> SEQUENCE: 56
tgcattcctg ttttgtaatg attttcggaa atttcgt                                 37

<210> SEQ ID NO 57
<211> LENGTH: 34
<212> TYPE: DNA
<213> ORGANISM: Artificial Sequence
<220> FEATURE:
<223> OTHER INFORMATION: Genome Scanner sequence

<400> SEQUENCE: 57
attgtttctt ttattcgtac agtaaatgat tatt                                    34

<210> SEQ ID NO 58
<211> LENGTH: 34
<212> TYPE: DNA
<213> ORGANISM: Artificial Sequence
<220> FEATURE:
<223> OTHER INFORMATION: Genome Scanner sequence

<400> SEQUENCE: 58
tgcattcctg ttttgtaatg attttcggaa attt                                    34

<210> SEQ ID NO 59
<211> LENGTH: 34
<212> TYPE: DNA
<213> ORGANISM: Artificial Sequence
<220> FEATURE:
<223> OTHER INFORMATION: Genome Scanner sequence

<400> SEQUENCE: 59
atagtttctt tgttgagaag actatatgag gaac                                    34
```

<210> SEQ ID NO 60
<211> LENGTH: 34
<212> TYPE: DNA
<213> ORGANISM: Artificial Sequence
<220> FEATURE:
<223> OTHER INFORMATION: Genome Scanner sequence

<400> SEQUENCE: 60
attttattta ttttaattttt aaaatttggt ttta                                34

<210> SEQ ID NO 61
<211> LENGTH: 34
<212> TYPE: DNA
<213> ORGANISM: Artificial Sequence
<220> FEATURE:
<223> OTHER INFORMATION: SpacerSorter sequence

<400> SEQUENCE: 61
gatttacata tattagcaat aaaagcagag caaa                                 34

<210> SEQ ID NO 62
<211> LENGTH: 34
<212> TYPE: DNA
<213> ORGANISM: Artificial Sequence
<220> FEATURE:
<223> OTHER INFORMATION: SpacerSorter sequence

<400> SEQUENCE: 62
cagtggccca tattagcaat aaaagttgag ttag                                 34

<210> SEQ ID NO 63
<211> LENGTH: 34
<212> TYPE: DNA
<213> ORGANISM: Artificial Sequence
<220> FEATURE:
<223> OTHER INFORMATION: SpacerSorter sequence

<400> SEQUENCE: 63
attttacatc ttttagcaat aatataaaac attg                                 34

<210> SEQ ID NO 64
<211> LENGTH: 34
<212> TYPE: DNA
<213> ORGANISM: Artificial Sequence
<220> FEATURE:
<223> OTHER INFORMATION: SpacerSorter sequence

<400> SEQUENCE: 64
tatagatctc ttttattgct aatatatgtt tcct                                 34

<210> SEQ ID NO 65
<211> LENGTH: 34
<212> TYPE: DNA
<213> ORGANISM: Artificial Sequence
<220> FEATURE:
<223> OTHER INFORMATION: SpacerSorter sequence

<400> SEQUENCE: 65
gtgtcacctc ttttattgct aatattggta attt                                 34

<210> SEQ ID NO 66
<211> LENGTH: 34
<212> TYPE: DNA
<213> ORGANISM: Artificial Sequence
<220> FEATURE:

<223> OTHER INFORMATION: SpacerSorter sequence

<400> SEQUENCE: 66
ttcaaaccca tattgaagcc aaaagattaa gggt                                34

<210> SEQ ID NO 67
<211> LENGTH: 34
<212> TYPE: DNA
<213> ORGANISM: Artificial Sequence
<220> FEATURE:
<223> OTHER INFORMATION: SpacerSorter sequence

<400> SEQUENCE: 67
cttgtggctc ttttggcttc aatattcgct tggc                                34

<210> SEQ ID NO 68
<211> LENGTH: 34
<212> TYPE: DNA
<213> ORGANISM: Artificial Sequence
<220> FEATURE:
<223> OTHER INFORMATION: SpacerSorter sequence

<400> SEQUENCE: 68
tgccttctta tattaataag aaaagtaaaa caaa                                34

<210> SEQ ID NO 69
<211> LENGTH: 34
<212> TYPE: DNA
<213> ORGANISM: Artificial Sequence
<220> FEATURE:
<223> OTHER INFORMATION: SpacerSorter sequence

<400> SEQUENCE: 69
ttttctattc ttttaataag aatatttgac ttaa                                34

<210> SEQ ID NO 70
<211> LENGTH: 34
<212> TYPE: DNA
<213> ORGANISM: Artificial Sequence
<220> FEATURE:
<223> OTHER INFORMATION: SpacerSorter sequence

<400> SEQUENCE: 70
tctggttttc ttttactggg aatatcagga attt                                34

<210> SEQ ID NO 71
<211> LENGTH: 34
<212> TYPE: DNA
<213> ORGANISM: Artificial Sequence
<220> FEATURE:
<223> OTHER INFORMATION: SpacerSorter sequence

<400> SEQUENCE: 71
catttccttc ttttatctgc aatataagaa ggaa                                34

<210> SEQ ID NO 72
<211> LENGTH: 34
<212> TYPE: DNA
<213> ORGANISM: Artificial Sequence
<220> FEATURE:
<223> OTHER INFORMATION: SpacerSorter sequence

<400> SEQUENCE: 72
catgtcagga tatttcctat aaaaggagag acaa                                34

```
<210> SEQ ID NO 73
<211> LENGTH: 34
<212> TYPE: DNA
<213> ORGANISM: Artificial Sequence
<220> FEATURE:
<223> OTHER INFORMATION: SpacerSorter sequence

<400> SEQUENCE: 73
cttaatccac ttttaactgc aatatagcat tctg                                34
```